(12) United States Patent
LaRochelle et al.

(10) Patent No.: US 6,368,828 B1
(45) Date of Patent: Apr. 9, 2002

(54) ATTENUATED AND DOMINANT NEGATIVE VARIANT CDNAS OF STAT6: STAT6B AND STAT6C

(75) Inventors: William LaRochelle, Madison, CT (US); Bharvin K. R. Patel, Westfield, IN (US); Jacalyn H. Pierce, Kula, HI (US)

(73) Assignee: The United States of America as represented by the Department of Health and Human Services, Rockville, MD (US)

(*) Notice: Subject to any disclaimer, the term of this patent is extended or adjusted under 35 U.S.C. 154(b) by 0 days.

(21) Appl. No.: 09/511,625

(22) Filed: Feb. 23, 2000

Related U.S. Application Data

(63) Continuation of application No. PCT/US98/17821, filed on Aug. 27, 1998.
(60) Provisional application No. 60/070,397, filed on Jan. 5, 1998, and provisional application No. 60/056,975, filed on Aug. 27, 1997.

(51) Int. Cl.$^7$ .......................... C12P 21/06; C17H 17/00; C07K 14/00

(52) U.S. Cl. ................ 435/69.1; 435/320.1; 435/252.3; 435/325; 536/23.1; 536/23.5; 530/350

(58) Field of Search .............................. 435/69.1, 320.1, 435/252.3, 325; 536/23.1, 23.5; 530/350

(56) References Cited

U.S. PATENT DOCUMENTS 5,591,825 A 1/1997 McKnight et al.

FOREIGN PATENT DOCUMENTS

WO WO 97/02023 1/1997 .......... A61K/31/00

OTHER PUBLICATIONS

Patel et al. "Localization of the human Stat6 gene to chromosome 12q13.3–q14.1, a region implicated in multiple solid tumors." *Genomics* 52(2):192–200, Sep. 1, 1998.
Mikita et al. "Mutational analysis of the STAT6 SH2 domain." *J. Biol Chem.* 273(28):17634–42, Jul. 10, 1998.
Patel et al. "Regulation of interleukin 4–mediated signaling by naturally occuring dominant negative and attenuated forms of human Stat6." *Proc. Natl. Acad. Sci. USA* 95:172–177, Jan., 1998.
Chen et al. "Jak1 expression is required for mediating interleukin–4–induced tyrosine phosphorylation of insulin receptor substrate and Stat6 signaling molecules." *J. Biol. Chem.* 272(10):6556–60, Mar. 7, 1997.
Patel et al. (Abstract) "Regulation of IL–4–mediated signalling by the naturally occuring dominant negative and attenuated forms of human Stat6." *FASEB J*. Jul. 31, 1997. 11(9):A769–1458. 17$^{th}$ International Congress of Biochemistry and Molecular Biology in conjuction with 1997 meeting of the American Society for Biochemistry and Molecular Biology. San Francisco, California, Aug. 24–29, 1997.
Takeda et al. STAT6: its role in interleukin–4–mediated biological functions. *J. Mol. Med.* 75(5)317–326, 1997.
Kaplan et al. "Stat6 is required for mediating responses to IL–4 and for development of Th2 cells." *Immunity* 4:313–319, Mar. 1996.
Takeda et al. "Essential role of Stat6 in IL–4 signalling." *Nature* 380:627–630, Apr. 18, 1996.
Mikita et al. "Requirements for interleukin–4–induced gene expression and functional characterization of Stat6." *Mol. Cell Biol.* 16(10):5811–5820, Oct. 1996.
Kaptein et al. "Dominant negative Stat3 mutant inhibits interleukin–6–induced Jak–STAT signal transduction." *J. Biol. Chem.* 271(11):5961–5964, Mar. 15, 1996.
Patel et al. "Stat6 and Jak1 are common elements in platelet–derived growth factor and interleukin–4 signal transduction pathways in NIH 3T3 fibroblasts." *J. Biol. Chem.* 271(36):22175–82, Sep. 6, 1996.
Wang et al. "Naturally occuring dominant negative variants of Stat5." *Mol. Cell Biol.* 16(11):6141–6148, Nov. 1996.
Kotanides and Reich. "Interleukin–4–induced STAT6 recognizes and activates a target site in the promoter of the interleukin–4 receptor gene." *J. Biol. Chem.* 271(41):25555–61, Oct. 11, 1996.
Xu et al. "Cooperative DNA binding and sequence–selective recognition conferred by the STAT amino–terminal domain." *Science* 273: 794–797, Aug. 9, 1996.
Leung et al. "STATs find that hanging together can be stimulating." *Science* 273:750–751, Aug. 9, 1996.

(List continued on next page.)

Primary Examiner—Karen Cochrane Carlson
(74) Attorney, Agent, or Firm—Needle & Rosenberg, P.C.

(57) ABSTRACT

The present invention provides an isolated nucleic acid encoding the polypeptide Stat6b, having an amino acid sequence of Stat6 wherein a deletion in the nucleic acid is present, encompassing the last base pair of codon 39 of Stat6 and continuing through to and including codon 86 of Stat6 and an isolated polypeptide, Stat6b, having an amino acid sequence of Stat6 wherein amino acids 39–86 are deleted at the amino terminus. Also provided is an isolated nucleic acid encoding the polypeptide Stat6c, having an amino acid sequence of Stat6 wherein amino acids 537–564 are deleted and an isolated polypeptide, Stat6c, having an amino acid sequence of Stat6 wherein amino acids 537–564 are deleted. Methods of producing the polypeptide Stat6b and polypeptide Stat6c are also provided, comprising culturing cells comprising nucleic acid encoding the polypeptide Stat6b or the polypeptide Stat6c under conditions whereby the polypeptide Stat6b or the polypeptide Stat6c is produced.

35 Claims, No Drawings

OTHER PUBLICATIONS

Palmer–Crocker et al. "IL–4 and IL–13 activate the JAK2 tyrosine kinase and Stat6 in cultured human vascular endothelial cells through a common pathway that does not involve the $\gamma_c$ chain." *J. Clin. Invest.* 98(3):604–609, Aug., 1996.

Quelle et al. "Cloning of murine Stat6 and human Stat6, Stat proteins that are tyrosine phosphorylated in responses to IL–4 and IL–3 but are not required for mitogenesis." *Mol. Cell Biol.* 15(6):3336–43, Jun. 1995.

Hou et al. "An interleukin–4–induced transcription factor: IL–4." *Science* 265:1701–03, Sep. 16, 1994.

US 6,368,828 B1

ATTENUATED AND DOMINANT NEGATIVE VARIANT CDNAS OF STAT6: STAT6B AND STAT6C

This application is a continuation of international patent application PCT/US98/17821, filed Aug. 27, 1998, which claims priority from provisional patent applications Ser. No. 60/070,397, filed Jan. 5, 1998 and Ser. No. 60/056,975, filed Aug. 27, 1997, the contents of which are incorporated herein in their entirety.

BACKGROUND OF THE INVENTION

1. Field of the Invention

The present invention relates to isoforms of the family of transcription factors known as Stat (signal transducers and activators of transcription). In particular, the present invention provides attenuated and dominant negative variants of human Stat6, which are designated Stat6b and Stat6c and which have differential effects on the modulation of Stat6 activity in cells.

2. Background Art

The Stats have been evolutionarily conserved from Drosophila to humans. Physiologically, Stat signaling pathways have been correlated with pleiotropic and mitogenic functional responses induced by a variety of growth factors, cytokines and interferons. In particular, Stat6 activation correlates with functional responses induced by interleukin-4 (IL-4) (22), interleukin-13 (IL-13) (25) and platelet-derived growth factor (PDGF) (26).

IL-4 is a pleiotropic cytokine that plays a prominent role in the regulation of inflammatory and cell-mediated immune responses (1). IL-4 treatment induces tyrosine phosphorylation of the IL-4 receptor, designated IL-4Rα (11, 12), a member of the hematopoietin receptor superfamily (13, 14). Unlike several members of the hematopoietin receptor superfamily, IL-4Rα is ubiquitously expressed on cells of hematopoietic and nonhematopoietic origin. IL-4Rα activation results in tyrosine phosphorylation of multiple substrates including Jak1, Jak3 (15, 16), IRS-1 (17), IRS-2/4PS (18) and Stat6 (13, 14, 19, 20). Phosphorylation of specific tyrosine residues within the two GYKXF motifs present in the IL-4Rα has been proposed to be crucial for binding to and activation of Stat6 (13, 22).

Selective activation of the Stats results in dimerization and translocation to the nucleus, where each interacts with unique DNA response elements and activates transcription (23, 24). Although phenotypic analysis of Stat6-/- mice have elegantly demonstrated a role for Stat6 in IL-4-induced lymphocyte proliferation, Th2 helper T cell differentiation, immunoglobulin class switching, and cell surface antigen expression (27–29), the mechanism(s) by which Stat6 induces these effects remain incompletely understood.

The present invention provides two previously unknown human Stat6 variants, Stat6b and Stat6c, that are a naturally occurring, attenuated variant and a naturally occurring dominant negative variant, respectively, of Stat6. Also provided is the entire genomic sequence of the human Stat6 gene, including chromosomal mapping and genetic linkage analysis.

SUMMARY OF THE INVENTION

The present invention provides an isolated nucleic acid encoding the polypeptide Stat6b, having an amino acid sequence of Stat6 wherein at least 110 amino acids are deleted at the amino terminus, as well as an isolated nucleic acid encoding the polypeptide Stat6b, having the nucleotide sequence of SEQ ID NO:1.

Further provided is an isolated polypeptide, Stat6b, having an amino acid sequence of Stat6 wherein at least 110 amino acids are deleted from the amino terminus, an isolated polypeptide, Stat6b, having an amino acid sequence of Stat6 wherein amino acids 39–86 are deleted at the amino terminus and an isolated polypeptide, Stat6b, having the amino acid sequence of SEQ ID NO:2.

In addition, the present invention provides an isolated nucleic acid encoding the polypeptide Stat6c, having an amino acid sequence of Stat6 wherein amino acids 537–564 are deleted and an isolated nucleic acid encoding the polypeptide Stat6c, having the nucleotide sequence of SEQ ID NO:3.

Also provided is an isolated polypeptide, Stat6c, having an amino acid sequence of Stat6 wherein amino acids 537–564 are deleted and an isolated polypeptide, Stat6c, having the amino acid sequence of SEQ ID NO:4.

A method of producing the polypeptide Stat6b or the polypeptide Stat6c is also provided, comprising culturing cells containing a vector comprising nucleic acid encoding Stat6b or nucleic acid encoding Stat6c under conditions whereby the polypeptide Stat6b or the polypeptide Stat6c is produced.

DETAILED DESCRIPTION OF THE PREFERRED EMBODIMENTS

As used herein, "a" can include multiples.

The present invention provides the discovery of previously unknown isoforms of the human Stat6 gene, produced by differential splicing of the Stat6 gene, which have been identified as having distinct modulating functions within cells in which they are expressed. Specifically, a family of proteins termed signal transducers and activators of transcription (Stat) is known. Among the members of the Stat family is the protein Stat6 which has been isolated and cloned (See, ref 39 or U.S. Pat. No. 5,591,825 (McKnight, et al., issued Jan. 7, 1997)). Stat6 has been shown to play a role in interleukin-4 (IL-4) mediated signaling and may play a role in lymphoid cell proliferation and transcription. In studying the role of Stat6, two previously unknown, naturally occurring isoforms of Stat6 of the present invention, Stat6b and Stat6c, have been isolated and cloned. Any reference below to particular codons or base pairs of human Stat6 in describing the sequence of Stat6b or Stat6c are derived from the publicly available cDNA sequence of Stat6 as provided in SEQ ID NO:1 of U.S. Pat. No. 5,591,825 issued Jan. 7, 1997 or from the genomic sequence of human Stat6 provided herein as SEQ ID NO:5 and the cDNA sequence of wild type human Stat6 provided herein as SEQ ID NO:67.

The present invention provides an isolated nucleic acid encoding the polypeptide Stat6b, having an amino acid sequence of Stat6 wherein at least 110 amino acids are deleted at the amino terminus. For example, the nucleic acid can have a deletion encompassing the last base pair of codon 39 of Stat6 and continuing through to and including codon 86 of Stat6. Additionally, the nucleic acid of this invention can be an isolated nucleic acid encoding the polypeptide Stat6b, having the nucleotide sequence of SEQ ID NO:1.

In addition, the present invention provides an isolated nucleic acid encoding the polypeptide Stat6c, having an amino acid sequence of Stat6 wherein amino acids 537–564 are deleted. For example, the nucleic acid encoding the polypeptide Stat6c can have a deletion encompassing the last base pair of codon 536 of Stat6 and continuing through to and including the first two base pairs of codon 564 of Stat6. In addition, the present invention provides an isolated nucleic acid encoding the polypeptide Stat6c, having the nucleotide sequence of SEQ ID NO:3.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence (39). Furthermore, nucleic acids may include codons which represent conservative substitutions of amino acids as described in Table I.

As used herein, the term "isolated" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (30). The nucleic acids of this invention can be isolated from cells according to methods well known in the art for isolating nucleic acids. Alternatively, the nucleic acids of the present invention can be synthesized according to standard protocols well described in the literature for synthesizing nucleic acids.

The nucleic acid of this invention can be used as a probe or primer to identify the presence of a nucleic acid encoding the Stat6b or Stat6c polypeptide in a sample.

The nucleic acid of this invention can also be used as a probe or primer to distinguish nucleic acid encoding Stat6 from nucleic acid encoding Stat6b and/or Stat6c. Thus, the present invention also provides a nucleic acid having sufficient complementarity to the Stat6b and/or Stat6c nucleic acid of this invention to selectively hybridize with the Stat6b and/or Stat6c nucleic acid of this invention under stringent conditions as described herein and which does not hybridize with Stat6 nucleic acid under stringent conditions.

"Stringent conditions" refers to the hybridization conditions used in a hybridization protocol or in the primer/template hybridization in a PCR reaction. In general, these conditions should be a combination of temperature and salt concentration for washing chosen so that the denaturation temperature is approximately 5–20° C. below the calculated $T_m$ (melting/denaturation temperature) of the hybrid under study. The temperature and salt conditions are readily determined empirically in preliminary experiments in which samples of reference nucleic acid are hybridized to the primer nucleic acid of interest and then amplified under conditions of different stringencies. The stringency conditions are readily tested and the parameters altered are readily apparent to one skilled in the art. For example, $MgCl_2$ concentrations used in PCR buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5–10° C. below the estimated $T_m$ in 6×SSPE, then washed at the same temperature in 2×SSPE (40). The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C. and a starting salt concentration of about 150 mM and modified accordingly by preliminary experiments. $T_m$ values can also be calculated for a variety of conditions utilizing commercially available computer software (e.g., OLIGO®).

Modifications to the nucleic acids of the invention are also contemplated as long as the essential structure and function of the polypeptide encoded by the nucleic acids is maintained. Likewise, fragments used as primers can have substitutions so long as enough complementary bases exist for selective amplification (44) and fragments used as probes can have substitutions so long as enough complementary bases exist for hybridization with the reference sequence to be distinguished from hybridization with other sequences.

Probes of this invention can be used, for example, to screen genomic or cDNA libraries or to identify complementary sequences by Northern and Southern blotting. Primers of this invention can be used, for example, to transcribe cDNA from RNA and to amplify DNA according to standard amplification protocols, such as PCR, which are well known in the art.

Thus, the present invention further provides a method of detecting the expression of Stat6 and/or a Stat6b and/or Stat6c isoform in cells in a biological sample by detecting mRNA for Stat6 and/or Stat6b and/or Stat6c in the cells comprising the steps of: contacting the cells with a detectably labeled nucleic acid probe that hybridizes, under stringent conditions, with mRNA for Stat6b and not with mRNA for Stat6 or Stat6c and/or contacting the cells with a detectably labeled nucleic acid probe that hybridizes, under stringent conditions, with mRNA for Stat6c and not with mRNA for Stat6 or Stat6c: and detecting the presence of mRNA and/or contacting the cells with a detectably labeled nucleic acid probe that hybridizes, under stringent conditions, with mRNA for Stat6 and not with mRNA for Stat6b or Stat6c. The mRNA of the cells in the biological sample can be contacted with the probe and detected according to protocols standard in the art for detecting mRNA, such as Northern blotting and PCR amplification. The detection and/or quantitation of DNA or mRNA encoding Stat6 and/or Stat6b and/or Stat6c can be used to detect differential expression of Stat6 isoforms in a wide variety of diseases, including, for example, but not limited to, myeloid cancer, asthma, sarcoma, scleroderma, bone marrow fibrosis, fibrotic diseases and acquired immune deficiency syndrome.

The nucleic acid encoding the polypeptide Stat6b or the polypeptide Stat6c of this invention as described herein can be part of a recombinant nucleic acid comprising any combination of restriction sites and/or functional elements as are well known in the art which facilitate molecular cloning and other recombinant DNA manipulations. Thus, the present invention further provides a recombinant nucleic acid comprising the nucleic acid encoding Stat6b or Stat6c of the present invention. In particular, the isolated nucleic acid encoding Stat6b or Stat6c and/or the recombinant nucleic acid comprising a nucleic acid encoding Stat6b can be present in a vector and vector can be present in a cell, which can be a cell cultured in vitro or a cell in a transgenic animal.

Thus, the present invention further provides a composition comprising a vector comprising a nucleic acid encoding Stat6b and a vector comprising a nucleic acid encoding Stat6c and a vector comprising nucleic acid encoding both Stat6b and Stat6c. The composition can be in a pharmaceutically acceptable carrier. The vector can be an expression vector which contains all of the genetic components required for expression of the nucleic acid encoding Stat6b and/or the nucleic acid encoding Stat6c in cells into which the vector has been introduced, as are well known in the art. The expression vector can be a commercial expression vector or it can be constructed in the laboratory according to standard molecular biology protocols. The expression vector can comprise viral nucleic acid including, but not limited to, adenovirus, retrovirus vaccinia virus and/or adeno-associated virus nucleic acid. The nucleic acid or vector of this invention can also be in a liposome or a delivery vehicle which can be taken up by a cell via receptor-mediated or other type of endocytosis.

The present invention further provides the entire genomic sequence of the human Stat6 gene as SEQ ID NO:5. The genomic sequence of the Stat6 gene can be used for producing probes for identifying introns and exons and intron/exon junctions by hybridization and for producing sequencing primers. In particular, the 5' end of the genomic sequence contains the Stat6 promoter which can be employed in assays to determine the therapeutic value of cis/trans regulation of the promoter by various growth factors, cytokines, lymphokines and chemokines which can be analyzed for this type of regulatory effect on the Stat6 promoter. In addition, identification of the intron sequences which regulate Stat6 splicing could provide a unique approach to regulating the expression levels of Stat6 isoforms.

In addition, the present invention provides the genetic locus of the human Stat6 gene as chromosome 12q bands 13.3–14.1. The identification of the Stat6 locus thus provides for detection of chromosomal aberrations and translocations involving the Stat6 gene. In particular, the 12q13 amplicon is dubbed the tumor specific amplicon (12q13), due to the high numbers of chromosomal aberrations/translocations affecting this locus that have been reported in a wide variety of tumors. The localization of the Stat6 gene to this region indicates that translocations/amplification/break points affecting the Stat6 gene can be found in a wide variety of tumors as well.

The present invention also provides an isolated polypeptide, Stat6b, having an amino acid sequence of Stat6 wherein at least 110 amino acids are deleted from the amino terminus, an isolated polypeptide, Stat6b, having an amino acid sequence of Stat6 wherein amino acids 39–86 are deleted at the amino terminus and an isolated polypeptide, Stat6b, having the amino acid sequence of SEQ ID NO:2.

Further provided is an isolated polypeptide, Stat6c, having an amino acid sequence of Stat6 wherein amino acids 537–564 are deleted and an isolated polypeptide, Stat6c, having the amino acid sequence of SEQ ID NO:4.

The present invention further provides a method of producing the polypeptide Stat6b or the polypeptide Stat6c, comprising culturing the cells of the present invention which contain a nucleic acid encoding the polypeptide Stat6b or nucleic acid encoding the polypeptide Stat6c under conditions whereby the polypeptide Stat6b or the polypeptide Stat6c is produced. Conditions whereby the polypeptide Stat6b or Stat6c is produced can include the standard conditions of any expression system, either in vitro or in vivo, in which the polypeptides of this invention are produced in functional form. For example, protocols describing the conditions whereby nucleic acids encoding the Stat6b or Stat6c proteins of this invention are expressed are provided in the Examples section herein. The polypeptide Stat6b or Stat6c can be isolated and purified from the cells according to methods standard in the art.

Specifically a method of producing the polypeptide Stat6b is provided, comprising culturing cells comprising vectors comprising a nucleic acid selected from the group consisting of: a) an isolated nucleic acid encoding the polypeptide Stat6b, having an amino acid sequence of Stat6 wherein at least 110 amino acids are deleted at the amino terminus, b) an isolated nucleic acid encoding the polypeptide Stat6b, having an amino acid sequence of Stat6 wherein a deletion in the nucleic acid is present, encompassing the last base pair of codon 39 of Stat6 and continuing through codon 86 of Stat6, inclusive, and an isolated nucleic acid encoding the polypeptide Stat6b, having the nucleotide sequence of SEQ ID NO:1, under conditions whereby the polypeptide Stat6b is produced.

Also provided is a method of producing the polypeptide Stat6c, comprising culturing cells comprising vectors comprising a nucleic acid selected from the group consisting of: a) an isolated nucleic acid encoding the polypeptide Stat6c, having an amino acid sequence of Stat6 wherein amino acids 537–564 are deleted, b) an isolated nucleic acid encoding the polypeptide Stat6c, having an amino acid sequence of Stat6 wherein a deletion in the nucleic acid is present, encompassing the last base pair of codon 536 of Stat6 and continuing through the first two base pairs of codon 564 of Stat6, inclusive, and an isolated nucleic acid encoding the polypeptide Stat6c, having the nucleotide sequence of SEQ ID NO:3, under conditions whereby the polypeptide Stat6c is produced.

In addition, the present invention provides peptides present in the wild type Stat6 sequence which are not present in the isoforms Stat6b or Stat6c. Specifically, the first 110 amino acids at the amino terminus of the wild type Stat6 polypeptide and/or amino acids 39–85 of wild type Stat6, as shown in SEQ ID NO:68 herein can be used to distinguish the presence of Stat6 and Stat6b on the basis that these amino acid sequences, which are present in Stat6, are not present in Stat6b. Thus, the peptides representing the 110 amino acids at the amino terminus of the wild type Stat6 polypeptide and/or amino acids 39–85 of wild type Stat6 can be used to produce antibodies which specifically bind Stat6 but do not bind Stat6b. Additionally, the nucleic acid sequence, encoding peptides representing the 110 amino acids at the amino terminus of the wild type Stat6 polypeptide and/or encoding amino acids 39–85 of wild type Stat6, as shown in SEQ ID NO:67 herein, can be used as probes and/or primers to distinguish a nucleic acid encoding a Stat6 polypeptide from a nucleic acid encoding a Stat6b polypeptide.

Similarly, amino acids 537–564 of the wild type Stat6 polypeptide as shown in SEQ ID NO:68 herein can be used to distinguish the presence of Stat6 and Stat6c on the basis that these amino acid sequences, which are present in Stat6, are not present in Stat6c. Thus, a peptide having amino acids 537–564 of wild type Stat6 can be used to produce antibodies which specifically bind Stat6 but do not bind Stat6c. Additionally, the nucleic acid sequence, encoding peptides representing amino acids 537–564 of wild type Stat6, as shown in SEQ ID NO:67 herein, can be used as probes and/or primers to distinguish a nucleic acid encoding a Stat6 polypeptide from a nucleic acid encoding a Stat6c polypeptide.

As used herein, "isolated" and/or "purified" means a polypeptide which is substantially free from the naturally occurring materials with which the polypeptide is normally associated in nature. Also as used herein, "polypeptide" refers to a molecule comprised of amino acids which correspond to those encoded by a nucleic acid. The polypeptides of this invention can consist of the entire amino acid sequence of the Stat6b or Stat6c protein or portions thereof that are distinguishable from portions of the wild type Stat6 polypeptide. The polypeptides or portions thereof of the present invention can be obtained by isolation and purification of the polypeptides from cells where they are produced naturally or by expression of exogenous DNA encoding the Stat6b or Stat6c polypeptide. Portions of the Stat6b or Stat6c polypeptides can be obtained by chemical synthesis of peptides, by proteolytic cleavage of the polypeptides and by synthesis from nucleic acid encoding the portion of interest The polypeptide may include conservative substitutions where a naturally occurring amino acid is replaced by one having similar properties. Such conservative substitutions do not alter the function of the polypeptide and would be understood to include at least those listed in Table 1. (41).

Thus, it is understood that, where desired, modifications and changes may be made in the nucleic acid and/or amino acid sequence of the Stat6b and Stat6c polypeptides of the present invention and still obtain a protein having like or otherwise desirable characteristics. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a Stat6b or Stat6c polypeptide without appreciable loss of functional activity. Since it is the interactive capacity and nature of a protein that defines that protein's biological functional activity, certain amino acid sequence substitutions can be made in a Stat6b or Stat6c amino acid sequence (or, of course, the underlying nucleic acid sequence) and nevertheless obtain a Stat6b or Stat6c polypeptide with like properties. It is thus contemplated that various changes may be made in the amino acid sequence of the Stat6b or Stat6c polypeptide (or underlying nucleic acid sequence) without appreciable loss of biological utility or activity and possibly with an increase in such utility or activity.

The present invention further provides antibodies which specifically bind the Stat6 isoforms Stat6b or Stat6c and do not bind Stat6. For example, antibodies which specifically bind Stat6c but do not bind Stat6b or Stat6 are made according to standard protocols from a peptide synthesized by standard protocols having the amino acid sequence LRSYWSDRDSEIGGIT (SEQ ID NO:66). In addition, antibodies which specifically bind Stat6 but do not bind Stat6b or Stat6c, as well as antibodies which specifically bind Stat6b but do not bind Stat6 or Stat6c, can be produced by well known methods for polyclonal and monoclonal antibody production according to the teachings provided herein.

The antibodies of the present invention include both polyclonal and monoclonal antibodies. Such antibodies may be murine, fully human, chimeric or humanized. These antibodies also include Fab or F(ab')$_2$ fragments. The antibodies can be of any isotype IgG, IgA, IgD, IgE and IgM. Such antibodies can be produced by techniques well known in the art which include those described in Kohler et al. (42) or U.S. Pat. Nos. 5,545,806, 5,569,825 and 5,625,126, incorporated herein by reference.

The antibodies of this invention can be used to detect the presence of Stat6 and/or Stat6b and/or Stat6c in a sample.

For example, a method is provided for detecting a Stat6b protein or antigen in a sample, which can be a biological sample, comprising contacting the sample with an antibody which specifically binds Stat6b and which does not bind Stat6c or Stat6, under conditions whereby an antigen/antibody complex can form and detecting the presence of the complex, whereby the presence of the antigen/antibody complex indicates the presence of a Stat6b protein or antigen in the sample.

In addition, a method is provided for detecting a Stat6c protein or antigen in a sample, which can be a biological sample, comprising contacting the sample with an antibody which specifically binds Stat6c and which does not bind Stat6b or Stat6, under conditions whereby an antigen/antibody complex can form and detecting the presence of the complex, whereby the presence of the antigen/antibody complex indicates the presence of a Stat6c protein or antigen in the sample.

Furthermore, a method is provided for detecting a Stat6 protein or antigen in a sample, which can be a biological sample, comprising contacting the sample with an antibody which specifically binds Stat6 and which does not bind Stat6b or Stat6c, under conditions whereby an antigen/antibody complex can form and detecting the presence of the complex, whereby the presence of the antigen/antibody complex indicates the presence of a Stat6 protein or antigen in the sample.

The conditions whereby an antigen/antibody complex can form and be detected can be standard conditions well known in the art for protocols such as immunoprecipitation, agglutination, Western blotting etc. Examples of protocols for producing and detecting antigen/antibody complexes are provided in the Examples section herein.

The present invention further contemplates a method for detecting the presence of Stat6 or Stat6b or Stat6c polypeptide in a biological sample comprising: contacting a biological sample with an antibody which specifically binds Stat6, Stat6b and Stat6c under conditions whereby an antibody/protein complex can form; isolating the protein in the antibody/protein complex; contacting a first portion of the isolated protein with an antibody which binds Stat6 and Stat6c but does not bind Stat6b under conditions whereby a protein/antibody complex can form and detecting the presence of complex formation; and contacting a second portion of the isolated protein with an antibody which binds Stat6 and Stat6b but does not bind Stat6c under conditions whereby a protein/antibody complex can form and detecting the presence of complex formation, whereby the absence of complex formation with the first portion of the isolated protein and the presence of complex formation with the second portion indicates the presence of Stat6b in the sample and the presence of complex formation with the first portion of the isolated protein and the absence of complex formation with the second portion of the isolated protein indicates the presence of Stat6c in the sample and the presence of complex formation in both the first and second portions indicates the presence of Stat6 in the sample.

For example, to produce an antibody which specifically binds Stat6 and Stat6b, but does not bind Stat6c, a peptide can be synthesized which consists of some or all of the 28 amino acids which are present in Stat6 and Stat6b but are deleted from Stat6c, such as, for example, LIIG-FISKQYVTSLLLNEPDGTFLLRFS (SEQ ID NO: 62) or FISKQYVTSLLLNEPDGT (SEQ ID NO:63). Such peptides can then be used to generate polyclonal or monoclonal antibodies according to standard protocols. To produce an antibody that specifically binds Stat6 and Stat6c but does not bind Stat6b, a peptide can be synthesized which consists of some or all of the amino acids which are present in Stat6 and Stat6c but are deleted from Stat6b, which are the first 110 amino acids at the amino terminus of Stat6. For example, peptides having the sequence MPPEKVQRLYVDFPQH (SEQ ID NO:64) or SDTVQHLQASVGEQGEGST (SEQ ID NO:65) can be used to generate polyclonal or monoclonal antibodies according to standard protocols.

As demonstrated by the data provided herein, Stat6b, when compared to Stat6, is an attenuated regulator of gene transcription. Stat6c is a dominant negative regulator of gene transcription. Due to the role of these variants in regulating gene transcription, the isolated and purified nucleic acids or amino acid sequences which encode Stat6b and Stat6c of the present invention can be used to study gene regulation and in screening assays for identifying drug candidates which may be agonists or antagonists of Stat6b and or Stat6c or of other molecular targets in the signaling pathways in which these molecules are involved.

Thus, the present invention additionally provides a bioassay for identifying agonists or antagonists of activity mediated by Stat6b and Stat6c, comprising contacting cells which express Stat6b or Stat6c with a substance to be identified as an agonist or antagonist of Stat6 isoform activity (e.g., growth factors, cytokines, chemokines, etc.) and assaying the cells for induction of Stat6b or Stat6c by various assays, such as, for example, RNase protection assay, RT-PCR amplification or immunodetection as are described herein and in the literature.

The present invention also contemplates the use of the Stat6b and Stat6c polypeptides of this invention in gene therapy protocols. In particular, Stat6b and/or Stat6c can therapeutically modulate the development and differentiation of B and T cells and can enhance IL-4 immunological function in immunocompromised individuals through B cell, T cell, mast cell and/or macrophage gene therapy. For example, Stat6b and/or Stat6c gene therapy can enhance the growth of CD4+ T lymphocytes killed during human immunodeficiency virus (HIV) infection. Likewise, targeted Stat6c dominant negative expression can reduce proliferation and inflammation associated with IL-4 functional response. Reduction of IL-4 responsiveness can help increase interferon-related immune responses. Furthermore, modulation of Stat6 activity can control the proliferation and differentiation of cell types involved in fibrotic disease such as arthritis, scleroderma, bone marrow fibrosis and lung fibrosis and in inflammatory responses associated with asthma. In addition, Stat6 has been demonstrated to be activated by PDGF which has been implicated in arthritis, atherosclerosis, fibrotic diseases and neoplasia. Stat6 agonists and/or antagonists can be screened as described herein for therapeutic potential for these molecules in controlling Stat6 function in these diseases and inflammatory responses, as well as in neoplasia and arteriosclerosis. For example, Stat6c gene therapy would be useful in treating any disease where Stat6 is involved in the disease process as well as to inhibit undesirable proliferative, inflammatory and differentiation effects mediated by Stat6.

Thus, the present invention also provides a method for delivering Stat6b and/or Stat6c to a cell comprising administering to the cell a nucleic acid encoding Stat6b and/or Stat6c under conditions whereby the nucleic acid is expressed, thereby delivering Stat6b and/or Stat6c to the cell. The nucleic acid can be delivered as naked DNA or in a vector (which can be a viral vector) or other delivery vehicles and can be delivered to the subject's cells by a variety of mechanisms well known in the art (e.g., uptake of naked DNA, viral infection, liposome fusion, endocytosis and the like). The cell can be any cell which can take up and express exogenous DNA and in particular can include, but is not limited to a lung tissue cell, myeloid cell, epithelial cell, B cell, T cell, mammary gland cell, mast cell, pancreas cell, kidney cell prostate cell and ovary cell.

The nucleic acid encoding Stat6b or Stat6c can be administered to the cells of the subject either in vivo and/or ex vivo. If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acid or vector of the present invention can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

In the methods described above which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the Stat6b and/or Stat6c protein. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g.,50,51). The recombinant retrovirus can then be used to infect and thereby deliver to the infected cells nucleic acid encoding Stat6b and/or Stat6c. The exact method of introducing the altered nucleic acid into mammalian cells is, of course, not limited to the use of retroviral vectors. Other techniques are widely available for this procedure including the use of adenoviral vectors (45), adeno-associated viral (AAV) vectors (46), lentiviral vectors (47) vaccinia viral vectors (57) and pseudotyped retroviral vectors (48). Physical transduction techniques can also be used, such as liposome delivery and receptor-mediated and other endocytosis mechanisms (see, for example, 49). This invention can be used in conjunction with any of these or other commonly used gene transfer methods.

The nucleic acid or vector may be administered orally, parenterally (e.g., intravenously), by intramuscular injection, by intraperitoneal injection, transdermally, extracorporeally, topically or the like, although intravenous administration is typically preferred. The exact amount of the nucleic acid or vector required will vary from subject to subject, depending on the species, age, weight and general condition of the subject, the severity of the disease being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (see, e.g., Remington's Pharmaceutical Sciences; ref 52).

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

As one example, if the nucleic acid of this invention is delivered to the cells of a subject in an adenovirus vector, the dosage for administration of adenovirus to humans can range from about $10^7$ to $10^9$ plaque forming unit (pfu) per injection but can be as high as $10^{12}$ pfu per injection (53,54). Ideally, a subject will receive a single injection. If additional injections are necessary, they can be repeated at six month intervals for an indefinite period and/or until the efficacy of the treatment has been established.

In the methods of the present invention for the treatment of, for example, a fibrotic disorder, the efficacy of the treatment can be monitored according to clinical protocols well known in the art for monitoring the treatment of fibrotic disorders. For example, such clinical parameters as histopathological examination, which can entail immunohistochemical analysis for various markers such as extracellular matrix production, viementin, collagen and the presence of mesenchymal cells, can be monitored according to methods standard in the art. Ideally, these parameters would be measured at about ten days after gene delivery.

The present invention is more particularly described in the following examples which are intended as illustrative only since numerous modifications and variations therein will be apparent to those skilled in the art.

EXAMPLES

Example I

Cloning and Characterization of Stat6 Variants

Materials. Anti-Stat6 peptide sera used for immunoprecipitation or immunoblot analysis were raised against amino acid residues 689 to 711 (NH2-VPQVYPPHSHSIPPYQGLSPEES-COOH) (SEQ ID NO:6) or 787 to 804 (NH2-GEDIFPPLLPPTEQDLTK-COOH) (SEQ ID NO:7), respectively. Anti-phosphotyrosine monoclonal antibody (mAb) was purchased from Upstate Biotechnology Inc. (Lake Placid, N.Y.). Murine IL-4 was obtained from Peprotech (Rocky Hill, N.J.). Antibodies to CD16/CD32 or I-Ad MHC class II conjugated to FITC were obtained from PharMingen (San Diego, Calif.). The sequences of one strand of the double stranded Iε and FcγR1 probes used for EMSA were 5'-GATCTAACTTCCCAAGAACAG-3' (SEQ ID NO:8) and 5'-GTATTTCCCAGAAAAGGAAC-3' (SEQ ID NO:9), respectively.

Stat6 cDNA cloning and transfection. Human Stat6 cDNA was cloned (26) and used for Stat6 variant screening. A cDNA library was constructed using oligo (dT) primed human M426 fibroblast cDNAs packaged into λpCEV29. For library screening, the bacterial strain Y1088 was infected with phage ($2 \times 10^4$ plaques per 150 nun plate). Nitrocellulose filters were hybridized with $^{32}$P-labeled fall length human Stat6 cDNA in Hybrisol-I (Oncor) at 42° C. for 20 hrs, washed under low stringency conditions (3×SSC, 0.1% SDS; once at 25° C. for 30 min, three times at 40° C. for 30 min) and exposed to X-ray film. The cDNA inserts from plaque-purified clones were sequenced by the dideoxy chain termination method using T7 polymerase (U.S. Biochemical).

pCEV29-Stat6 variant or control pCEV29 cDNAs containing the neomycin gene were electroporated into FDC-P2 cells overexpressing the erythropoietin (EPO) receptor. Stable transfectants were generated by selection in geneticin (750 μg/ml) and clonal transfectants were established by single cell dilution. Transfectants were maintained in RPMI media containing EPO (1 U/ml)/geneticin (750 μg/ml) and used throughout this study unless otherwise stated.

Polymerase chain reaction analysis of Stat6 variant expression. Reverse transcription-polymerase chain reaction (RT-PCR) was performed according to the manufacturer's protocol using the EZ rTth RNA PCR kit (Perkin-Elmer), 2 μg of total RNA and the following primer pairs: P1: 5'-CTGGGATCCTATGGGGCCTGGAAGTGCCGC-3' (SEQ ID NO:10) and P2: 5'-ATGAATTCGTGGCCACCAGCTTCAGGGGGTC-3' (SEQ ID NO:11) for the amplification of cDNA encoding the NH2-terminal region of Stat6 and P3: 5'-CTGGGATCCGGAGCTACTGGTCTG-3' (SEQ ID NO:12) and P4: 5'-ATGAATTCTTGGGATAGAGATTTT-3' (SEQ ID NO:13) for the amplification of cDNA encoding the SH2 domain of Stat6. RT-PCR conditions were: one cycle each at 70° C. for 10 min, 4° C. for 2 min, and reverse transcription at 62° C. for 60 min. The initial melting was performed at 95° C. for 2 min, followed by 50 cycles each of denaturation (95° C. for 45 sec), annealing and extension (60° C. for 2 min), and one cycle of final extension (72° C. for 10 min).

RNASE protection assay. Total RNA was isolated from a variety of human tissues or obtained from CLONTECH (Palo Alto, Calif.). A 344 bp fragment from the 5' end of the human Stat6c cDNA was amplified by PCR and cloned in the pBluescriptII KS(+) vector. The identity of the insert was confirmed by sequencing. The plasmid was linearized at the Eco RI site and a $^{32}$P-UTP labeled 395 bp antisense RNA was synthesized with T7 polymerase. The probe was designed such that Stat6, Stat6b and Stat6c transcripts would result in 276, 140 and 344 bp protected products, respectively. A 125 bp riboprobe synthesized from the human GAPDH cDNA (PharMingen, San Diego, Calif.) was mixed with the Stat6 probe and added as an internal standard to each sample. The size of the protected GAPDH transcript was 97 bp. The RNASE protection assay was performed as recommended by the manufacturer (Ambion, Austin, Tex.). Briefly, the riboprobes were coprecipitated with 50 μg of total RNA from each tissue sample, resuspended in the 20 μl hybridization solution and incubated at 42° C. for 18–20 hours. The RNA hybrid digested with RNASE A (10 μg) and RNASE T1 (100 Units) for 30 minutes at 37° C. Protected products were analyzed on a 6% acrylamide-urea gel and visualized by autoradiography.

Mitogenic Assay. [$^3$H]thymidine incorporation into FDC-P2 cells was performed as previously described (12) with the following modifications. FDC-P2 cells or FDC-P2 transfectants stably expressing each Stat6 variant ($2 \times 10^5$ cells/ml) were washed and resuspended in RPMI 1640 medium with 15% fetal bovine serum (FBS) containing either IL-3 (5% WEHI) or IL-4 (0.0001–10 ng/ml). After 48 hours of stimulation with either cytokine, cells were incubated with [$^3$H] thymidine (2 μCi/ml) for five hours, washed and harvested onto glass filters with an automatic harvester (Skatron, Norway). [$^3$H]-thymidine incorporation was measured using a Beckman 5500 scintillation counter. FDC-P2 cells treated with FBS alone incorporated less than 0.1% of the counts incorporated in the presence of IL-3. EPO (1 U/ml) standardization of mitogenic assays showed <5% variation among transfectants.

Fluorescence activated cell sorting (FACS) analysis of cell surface antigen expression. FDC-P2 or FDC-P2 transfectants were untreated or treated with IL-4 (100 ng/ml) for 72 hrs. $1 \times 10^6$ cells were incubated for 60 min on ice with 2 μg anti-I-A$^d$, anti-CD23 or anti-CD16/CD32 conjugated to FITC (PharMingen, San Diego, Calif.). Cells were washed with 5 ml of ice-cold phosphate buffered saline (PBS) containing 0.1% sodium azide and resuspended in 100 μl PBS, 0.1% sodium azide. Flow cytometry was performed and quantitated using a FACScan (Becton-Dickinson).

Phosphotyrosine analysis. FDC-P2-Stat6 variant transfectants were starved in Dulbecco's modified eagles medium (DMEM), 25 μM sodium orthovanadate for 3 hr, stimulated with IL-4 (500 ng/ml) for 20 min and washed once with cold PBS, 100 μM sodium orthovanadate. Whole cell lysates were prepared by solubilization in RIPA buffer [50 mM Tris pH 7.4, 50 mM NaCl, 1.0% Triton X-100, 5 mM EDTA, 10 mM sodium pyrophosphate, 50 mM sodium fluoride, 1 mM sodium orthovanadate, 1 mM phenylmethylsulfonylfluoride, leupeptin (10 μg/ml), pepstatin (10 μg/ml) and aprotinin (1 μg/ml)] and incubated on ice for 30 min. After centrifugation at 14,000 rpm for 15 min, supernatants containing equivalent amounts of total protein, as determined by the method of Bradford, were incubated with anti-Stat6 serum for 1 hr. Next, protein A Sepharose CL4B (1:1 slurry) was added and samples were rotated at 4° C. for 3–4 hours. Immunocomplexes were washed three times with RIPA buffer. Sodium dodecyl sulfate-polyacrylamide gel electrophoresis (SDS-PAGE) sample buffer containing 100 mM dithiothreitol was added and samples were heat denatured at 100° C. for 10 min and fractionated on 7.5% SDS-polyacrylamide gels. After electrophoretic transfer to Immobilon-P membranes, filters were blocked in TTBS (10 mM Tris pH 8.0, 150 mM NaCl, 0.05% Tween 20), 3% nonfat milk. Membranes were then incubated with anti-Stat6 serum (1:1000) or anti-phosphotyrosine (1:1000) for 1–2 hours in TTBS, 1% BSA and washed four times with TTBS. Bound antibody was detected by incubation with anti-rabbit antibody (1:10,000) or anti-mouse antibody (1:10,000) conjugated to horseradish peroxidase (Amersham, Arlington Heights, Ill.), for 30 min and subsequently washed four times with TTBS. Enhanced chemiluminescence (Amersham) was performed according to the manufacturer's protocol.

Electrophoretic mobility shift and supershift analysis (EMSA). Briefly, FDC-P2 cells or FDC-P2-Stat6 transfectants were starved for 3 hrs as described. Cells were treated for the indicated time period with 500 ng/ml IL-4, washed once with cold PBS, 100 μM sodium orthovanadate and solubilized in gel shift lysis buffer (26) by incubation on ice for 60 min and vortexing. Lysates were cleared by centrifugation. For EMSA, 5 μg of whole cell lysate was incubated with the [$^{32}$P]-oligonucleotide ([$^{32}$P]Iε) probe in 20 mM HEPES (N-2-Hydroxyethylpiperazine-N'-2-Ethanesulfonic Acid), pH 7.9, 40 mM KCl, 1 mM MgCl$_2$, 100 μM EDTA, 500 μM dithiothreitol (DTT), 6.0% glycerol, 1 mg/ml BSA and 100 μg/ml poly(dIdC) for 15 min and then fractionated on 0.22×TBE (100 mM Tris borate, pH 8.0, 2 mM EDTA), 4.5% acrylamide gels.

Luciferase reporter analysis. Luciferase reporter plasmids were constructed using a 4×FcγRI site (5'-GTATTTCCCAGAAAAGGAAC-3') (SEQ ID NO:14) cloned into the Nhe I to Bgl II sites of pGL2-Basic (Promega) containing a TATA-box and minimal c-fos promoter (30). NIH 3T3 cells ($1 \times 10^6$ cells/plate) overexpressing IL-4Rα were transiently transfected by calcium phosphate precipitation with 1.0–10.0 μg of each Stat6 variant and 5 μg of reporter plasmid. After 24 hrs, cells were starved overnight in serum free DMEM and treated with or without IL-4 (500 ng/ml) for 6 hrs. Cells lysates were prepared and luciferase activity was measured using a Lumat-LB luminometer (Berthold, Nashua, N.H.). Relative light units (RLU) for each sample were normalized to protein concentration as measured by the method of Bradford.

Isolation of human Stat6 variant cDNAs and comparison of deduced amino acid sequences. To investigate IL-4Rα-mediated signal transduction and transcriptional activation, wild type human Stat6 and three Stat6 variant cDNAs; Stat6a, Stat6b, and Stat6c were cloned from a human M426 embryonic lung fibroblast cDNA library. In comparison to Stat6 cDNA, Stat6a possessed a dramatically shorter 3' noncoding region and a polyadenylation sequence juxtaposed to the termination codon. Differences among the Stat6, Stat6b and Stat6c cDNA noncoding regions were noted primarily near the polyadenylation sequences. Stat6c also contained a 68 bp insertion upstream of the initiation codon. The Stat6 and Stat6a cDNA coding regions were identical while Stat6b possessed a 139 bp deletion encompassing the last bp of codon 39 up to and including the codon 86, resulting in the introduction of a stop codon. Stat6c contained an 84 bp deletion comprised of the last bp of codon 536 up to and including the first two bp of codon 564.

The deduced amino acid sequence of each Stat6 variant was compared. The encoded gene products of Stat6 and Stat6a were identical and because no significant biologic differences were observed when these cDNAs were expressed in FDC-P2 or NIH 3T3 cells, Stat6a herein will be referred to as Stat6. Stat6b possessed an NH$_2$-terminal truncation of at least 110 amino acids due to the introduction of a stop codon and utilization of an internal initiation site, presumably Met$_{111}$. The deduced Stat6c amino acid sequence was identical to that of Stat6 except for a deletion of amino acid residues 537 to 564 within the SH2 domain of the molecule.

Detection and quantitative expression of Stat6 variant mRNA in human tissues. To determine whether the Stat6b and Stat6c cDNAs were authentic copies of mRNAs, RT-PCR analysis utilizing oligonucleotide primers designed to detect each variant was performed on RNA isolated from various human tissues (kidney, skeletal muscle, liver, ling, brain, adrenal, small intestine, testis, prostate, thymus, spleen, mammary gland and ovary). Primers proximal but upstream of the Stat6c noncoding insertion and adjacent but downstream of the Stat6b deletion amplified Stat6, Stat6b or Stat6c as unique amplicons in multiple tissue samples. A second RT-PCR analysis using primers flanking the SH2 domain further verified the existence of the Stat6c SH2 domain deletion. The identity of each amplicon was confirmed by cDNA sequencing.

To investigate quantitative differences in the expression of each Stat6 variant transcript among the various human tissues, a ribonuclease (RNASE) protection assay was performed. Individual Stat6 variant mRNAs were normalized to GAPDH mRNA for each tissue sample. Transcripts encoding Stat6, Stat6b, or Stat6c were detected at varying levels in all tissues studied. Stat6b and Stat6c transcripts were expressed to the greatest extent in spleen and lung, respectively. Among the variants, Stat6 mRNA was consistently quantitated at two to four times the level of Stat6b mRNA, depending on the tissue analyzed. Interestingly, the Stat6 transcript was expressed at 2.7 to 13.8 times the amount of the Stat6c transcript in the various tissues. Thus, Stat6 variant mRNAs were shown to be differentially expressed in a variety of human tissues.

Effect of Stat6 isoform expression on IL-4-induced [$^3$H]-thymidine uptake and cell surface antigen expression in FDC-P2 cells. The effect of each Stat6 isoform on IL-4-mediated proliferation was investigated by expressing each gene product in FDC-P2 cells and examining IL-4-induced DNA synthesis. IL-4 (10 ng/ml) induced 25% greater [$^3$H]-thymidine incorporation in FDC-P2 cells overexpressing Stat6 (FDC-P2-Stat6) than similarly treated FDC-P2 empty vector transfectants. DNA synthesis induced by IL-4 in FDC-P2 cells overexpressing Stat6b (FDC-P2-Stat6b) was similar to that observed in control FDC-P2 cells. In contrast, treatment with saturating concentrations of IL-4 (10 ng/ml) resulted in reduced [$^3$H]-thymidine incorporation by at least 30% in FDC-P2-Stat6c. Expression of Stat6c inhibited IL-4-mediated [$^3$H]-thymidine incorporation by 50–70% at lower IL-4 concentrations when compared to empty vector transfected cells. Thus, expression of Stat6 enhances, whereas Stat6c inhibits IL-4-induced DNA synthesis in FDC-P2 transfectants.

IL-4 has pronounced effects on the cell surface expression of I-A$^d$ (MHC Class II) molecules and Fc receptors (4, 5). In human monocytes, IL-4 has been shown to induce Stat6 binding to the FcγRI promoter (13, 14). Therefore, whether expression of the different Stat6 isoforms had any effect on the levels of IL-4-inducible cell surface antigens in FDC-P2 cells was analyzed by flow cytometry. As expected, I-A$^d$ and CD16/CD32 cell surface staining was increased in IL-4-treated FDC-P2 cells. Enhanced I-A$^d$ and CD16/CD32 staining was observed in FDC-P2-Stat6 transfectants. FDC-P2-Stat6b transfectants also showed up-regulation of IL-4-induced I-A$^d$ and CD16/CD32 expression but to a much lesser extent. In contrast, the ability of IL-4 to induce I-A$^d$ and CD16/CD32 molecules was abolished in FDC-P2-Stat6c transfectants. Similar effects on CD23 molecules were also observed. These results indicate that Stat6 plays a significant role in mediating IL-4-induced I-A$^d$, CD16/CD32 and CD23 cell surface expression in FDC-P2 cells. Moreover, Stat6c has potent dominant inhibitory effects on the ability of IL-4 to mediate up-regulation of these cell surface antigens.

Effects of IL-4 stimulation on tyrosine phosphorylation of Stat6 isoforms expressed in FDC-P2 cells. To gain insight into the mechanistic basis by which Stat6b and Stat6c might be exerting effects on IL-4-mediated proliferation and functional responses, the expression and tyrosine phosphorylation of each Stat6 isoform was analyzed in the FDC-P2 transfectants. Expression was first examined using anti-human Stat6 serum that does not recognizes murine Stat6. Whole cell lysates from untreated or IL-4-treated FDC-P2 or FDC-P2-Stat6 isoform transfectants were immunoprecipitated with the anti-human Stat6 serum, subjected to SDS-PAGE and resolved proteins were subsequently immunoblotted with anti-human Stat6 serum. A 100 kDa species was readily observed in immunoprecipitates from FDC-P2 cell lysates overexpressing human Stat6. Stat6b and Stat6c were detected as 95 and 102 kDa species in FDC-P2-Stat6b or FDC-P2-Stat6c immunoprecipitates, respectively. Stat6 and Stat6b were expressed at similar levels, while Stat6c was expressed at levels three-fold lower than that of either of the other isoforms. No human Stat6 was detected in immunoprecipitates from FDC-P2 cells transfected with the pCEV29 vector alone.

To determine whether each Stat6 isoform could be activated by IL-4, whether these Stat6 species became tyrosine phosphorylated in response to IL-4 treatment was examined. Whole cell lysates from untreated or IL-4-treated FDC-P2-Stat6 transfectants were immunoprecipitated with anti-human Stat6 serum, subjected to SDS-PAGE and resolved proteins were immunoblotted with anti-phosphotyrosine antibody. 100 kDa and 95 kDa tyrosine-phosphorylated species were readily detected in IL-4-treated FDC-P2-Stat6 and FDC-P2-Stat6b transfectants, respectively. Stat6 tyrosine phosphorylation was greater than that of Stat6b and no Stat6c tyrosine phosphorylation was detected.

Experiments were then conducted to determine whether Stat6 isoform overexpression would affect endogenous murine Stat6 phosphorylation. To assay endogenous Stat6 activation, lysates were immunoprecipitated with an anti-Stat6 serum that recognizes both murine and human Stat6. Similar levels of murine Stat6 were observed in FDC-P2 cells and FDC-P2 isoform transfectants. Human Stat6 isoform expression was detected in a manner consistent with that observed utilizing anti-human Stat6 serum. Similar levels of endogenous murine Stat6 tyrosine phosphorylation were detected in native FDC-P2 cells as well as in Stat6 and Stat6b isoform transfectants in response to IL-4 treatment. However, Stat6c expression slightly, but consistently, diminished (14.7±2.1%) IL-4-induced endogenous murine Stat6 tyrosine phosphorylation. Human Stat6 and Stat6b, but not Stat6c, tyrosine phosphorylation was also detected utilizing this antiserum, confirming our previous results. These results indicate that Stat6 and Stat6b, but not Stat6c, are tyrosine phosphorylated in response to IL-4 and that IL-4-mediated tyrosine phosphorylation of endogenous murine Stat6 is only partially reduced by the expression of the human Stat6c isoform.

Differential DNA binding activity and transcriptional activation of Stat6 isoforms. Stat6 has been shown to bind with high affinity to a region within the FcγRI promoter (13, 14). Its DNA binding capacity can be readily distinguished from that of the other Stats by its ability to bind a GAS-like element found in the Ig germ line ε promoter of the IL-4-responsive human Cε gene (Iε). To determine whether expression of the three human Stat6 isoforms affected IL-4-induced FcγRI and Iε promoter binding activity, FDC-P2 transfectants were stimulated for 20 min. Whole cell extracts were prepared and assayed for the induction of [$^{32}$P]-FcγRI or [$^{32}$P]-Iε DNA binding activity by EMSA. Although extracts from untreated FDC-P2 did not contain any FcγRI or Iε binding activity, IL-4 treatment led to rapid induction of FcγRI and Iε binding. DNA binding activity was confirmed by promoter competition studies and supershift analysis utilizing two independent Stat6 antisera. IL-4-induced [$^{32}$P]-FcγRI or [$^{32}$P]-Iε binding activity observed in lysates from FDC-P2 transfectants overexpressing human Stat6 was identical to that detected in lysates from IL-4-stimulated parental FDC-P2 cells, albeit at greatly increased levels. Overexpression of Stat6b also led to enhanced DNA binding but to a lesser extent than that observed in FDC-P2-Stat6 lysates. Stat6c did not possess detectable DNA binding activity. In contrast, it inhibited IL-4-induced endogenous murine Stat6 FcγRI and Iε DNA binding activity by greater than 80%.

To gain further insights concerning the role of each Stat6 variant in mediating IL-4-induced transcriptional activation, the FcγRI promoter was coupled to a luciferase reporter containing the minimal fos promoter. IL-4 treatment of NIH 3T3-Stat6 transfectants resulted in a 220-fold induction of the FcγRI luciferase reporter compared to a 5-fold induction observed in IL-4-treated control NIH 3T3-pCEV29 empty vector transfectants. NIH 3T3-Stat6b transfectants exhibited a 20-fold induction.

The mechanism by which Stat6c exerted inhibitory effects was also investigated en using the FcγRI-luciferase reporter. In contrast to the enhanced transcription observed with Stat6, IL-4-induced luciferase activity was completely abolished in NIH 3T3-Stat6c transfectants. Indeed, Stat6c exerted a dominant negative effect on transcriptional activation even when transfected at a concentration much less than that of Stat6. The dose dependent inhibition of Stat6-induced transcriptional activation by Stat6c further indicates that Stat6c expression levels predicate transcriptional outcome.

Effect of Stat6c on endogenous Stat6 dimerization. To elucidate the molecular mechanism of Stat6c's potent transcriptional inactivation, several possibilities were considered. Because endogenous Stat6 tyrosine phosphorylation is only partly diminished by Stat6c, inhibition of IL-4-induced endogenous Stat6 association with IL-4Rα or JAK activation appeared unlikely. Moreover, Stat6c does not directly bind FcγRI or Iε promoter elements, making competitive transcriptional inactivation improbable. Therefore, crosslinking studies were performed to investigate whether Stat6c might effect endogenous Stat6 dimerization. Whole cell lysates from IL-4-treated FDC-P2 cells or Stat6 and Stat6c transfectants were incubated with disuccinimidyl glutarate (DSG). Immunoprecipitation followed by immunoblotting with anti-Stat6 serum revealed the presence of a Stat6 dimer in IL-4-treated lysates. FDC-P2-Stat6 transfectants treated with IL-4 exhibited greatly increased levels of the Stat6 dimer when compared to the endogenous Stat6 in the FDC-P2 control cells.

Strikingly, endogenous Stat6 dimerization was reduced by greater than 60% in IL-4-treated FDC-P2-Stat6c transfectants in comparison to the FDC-P2 control cells. Thus, the molecular basis of transcriptional inactivation by Stat6c appears to be due to the suppression of endogenous Stat6 dimer formation.

Example II

Cloning, Characterization and Chromosomal Localization of Human Stat6.

Cloning and cDNA sequence analysis of the human Stat6 gene. A human placental genomic library packaged in the λ FIX-II vector (Stratagene, LaJolla, Calif.) was screened with a $^{32}$P-labeled Stat6 cDNA probe using standard recombinant DNA protocols (56). Positive plaques were isolated and purified by secondary screening. The human Stat6 genomic clone (pBP95) was also isolated from a human P1 genomic library (Genome Systems Inc., St. Louis, Mo.). Regions of the P1 clone were used to confirm and span gaps among the λ FIX-II genomic clones. DNA was purified from positive plaques and mapped by restriction enzyme digestion combined with the Southern blot analysis. Fragments that hybridized to the Stat6 cDNA probe were isolated from the λ3 clone and subcloned into pBluescript II KS+ (Stratagene) to yield the plasmids pBP2, pBP3, pBP68, and pBP74. Both cDNA strands were completely sequenced using an ABI PRISM dye terminator cycle sequencing kit and automated ABI PRISM 310 genetic analyzer, or manually by SEQUENASE kit (United States Biochemical) using human Stat6 sequence-derived primers.

Transcriptional start site determination. To determine the mRNA initiation site(s) on genomic Stat6 DNA, an oligonucleotide (5'-CTGTCCAGCGAGTTCAAGGCT-3') (SEQ ID NO:15) complementary to the Stat6 cDNA sequence 90–120 base pairs upstream of the ATG codon was labeled by T4 polynucleotide kinase and [γ$^{32}$p] ATP. The labeled primer was annealed to 70 µg of total RNA isolated from human M426 fibroblasts or yeast. The annealed primer was extended by Superscript reverse transcriptase (Life Technologies Inc., Gaithersburg, Md.) and the extended products were analyzed by electrophoresis (6% polyacrylamide/8M urea gel). In parallel, the genomic DNA sequence was read by extension from the same primer annealed to pBP3.

Promoter constructs and basal luciferase activity. The Kpn I-Nhe I fragment (5.5 kb) that contained the first exon and the upstream flanking sequence of Stat6 was isolated from pBP3 and cloned into compatible polylinker sites of the luciferase reporter pGL3 (Promega), designated pBP78. The pBP78 plasmid construct was double digested with Kpn I and either Bln I, Eco RI, Spe I, or Bss HII, blunted with Klenow polymerase and self-ligated to engineer pBP82 (−445 to +133), pBP84 (−737 to +133), pBP86 (−940 to +133) and pBP88 (−2439 to +133), respectively.

To study basal promoter activity, murine NIH 3T3 fibroblasts were cultured in 6-well plates ($3 \times 10^5$ cells per well) for 24 hours and then transfected with individual Stat6 promoter-luciferase chimeric constructs using a calcium phosphate precipitation protocol. The Renilla-luciferase reference plasmid pRL-CMV (Promega, Madison, Wis.) served as an internal standard for monitoring transfection efficiency and data normalization. For transfection, 2 µg of promoter-luciferase construct and 1 µg of pRL-CMV were used per $3 \times 10^5$ cells. After incubation of the cells with the DNA-calcium phosphate precipitates for five hours in Dulbecco's modified Eagle's medium (DMEM)/10% calf serum, the cells were washed twice with DMEM and incubated for 72 hours in DMEM/10% calf serum before harvesting. For the determination of luciferase activity, the cells were washed, extracted in lysis buffer and assayed for luciferase activity according to the manufacturer's protocol (Promega). A Lumat-LB luminometer (Berthold) equipped with a dual injector was used to measure luciferase activity.

Fluorescence in situ hybridization (FISH). An 8 kbp fragment isolated from the Stat6-P1 genomic clone was isolated and labeled with biotin-dUTP or digoxigenin-11-dUTP (Random Primed DNA Labeling Kit, Boehringer-Mannheim). The labeled probe was used for in situ hybridization of human chromosomes derived from methotrexate-synchronized normal peripheral lymphocyte cultures. The conditions of the hybridization, detection of hybridization signals, digital-image acquisition, processing and analysis as well as the procedure for direct visualization of fluorescent signals to banded chromosomes were performed as described (43,55).

Genomic structure of the human Stat6 gene. Two non-overlapping lambda DNA clones designated λ3 and λ4, of the human Stat6 gene were isolated from a λFIX-II human genomic DNA library using full length human Stat6 cDNA as a probe. A major portion of the λ3 clone contained the 5' flanking region of the Stat6 gene, while its downstream region covered exons 1 through 11. The λ4 clone consisted of exons 15 through 23 and the 3' flanking region downstream of the Stat6 gene. To map exon 12 through 14, an additional genomic clone was isolated by screening a human P1 library with the full length Stat6 cDNA. The P1-Stat6 plasmid clone contained the entire human Stat6 gene, including both the 5' and 3' flanking regions of the gene as determined by restriction endonuclease and DNA sequence analysis.

Comparison of the genomic clones with the longest Stat6 variant cDNA sequence revealed that the human Stat6 gene is approximately 18 kb in length and consists of 23 exons interrupted by 22 introns. The exon/intron junction sequences as well as the sizes of the human Stat6 gene's exons and introns are summarized in Table II. The first two exons of the Stat6 gene are noncoding. Most exons are relatively small in size and ranged from 53 bp (exon 7) to 205 bp (exon 14) with the exception of exon 23. Although exon 23 is the largest in size (1346 bp), it encodes only the carboxy terminal 62 amino acids of Stat6. Intron sizes vary from 88 bp (intron 22) to approximately 4150 bp (intron 14). While sizes of most introns were determined by sequencing, the length of the intron 12 and 14 was determined by PCR amplification using two sets of Stat6 specific primers that flanked these introns. Of note, all introns are flanked by the classical GT/AG sequence that conformed well to the consensus for 5' splice donor and 3' splice acceptor sites found in other human genes (Table II). As set forth in the sequence listing, "N" as used in SEQ ID NO:39 and SEQ ID NO:43 represents a region of nucleotides that have not been sequenced. Thus, as shown in Table II, it is believed that the intron represented in SEQ ID NO:39 comprises approximately 1450 bases and the intron represented in SEQ ID NO:43 comprises approximately 4150 bases.

Analysis of the distribution of the various motifs encoded by the human Stat6 gene showed that the AUG translation initiation codon encoding the first amino acid is located within exon 3. Most of the SH2 domain, except the first four and last three codons, is contained within exon 16 and 17. The DNA binding domain and the putative SH2-like domain are transcribed from exons 10–14 and 14–15 respectively. The phosphorylated tyrosine residue of Stat6 (Y641) is encoded within exon 17. Two regions of maximal amino acid conservation between the Stats are distributed within exons 10 and 13. Characterization the Stat6 mRNA start site and 5' flanking sequence. The location of the human Stat6 mRNA start site was established by RNASE protection assay after performing an initial primer extension analysis. Hybridization of antisense riboprobes generated from a 260-bp Pml I-Nhe I or a 497-bp Bsu 36I-Nhe I genomic fragment with total RNA from human M426 fibroblasts that express a relatively high level of Stat6 mRNA resulted in protected bands.

Restriction mapping of the human Stat6 λ3 clone using single or double restriction endonuclease digestions combined with Southern blot hybridization identified an 8.2-kb Kpn I-Sal I fragment that contained a 5'-flanking sequence and exons 1–3. The 8.2-kb Kpn I-Sal I fragment was subcloned and sequenced. The nucleotide sequence of approximately 2.5-kb of the human Stat6 5' flanking sequence and 134 bp of 5'-untranslated sequence contained within the Stat6 cDNA clones was identified.

Transcription factor database 7.3 (IntelliGenetics, Inc., Mountain View, Calif.) was used to perform computer analysis of the Stat6 5' flanking/putative promoter sequences to identify potential transcription factor consensus binding sites. Interestingly, the Stat6 promoter did not contain TATA (SEQ ID NO:69) box or CCAAT (SEQ ID NO:70) sequence upstream and within 100 bp of the transcription start site. However, the Stat6 promoter contained a TATA box and CCAAT sequence at −2552 and −1692 respectively. The promoter contained one GC box, the proposed site for binding Sp1 transcription factor. Several transcriptional regulatory consensus sequences were also found within the putative promoter, including binding sites for p53 (−674 bp), p21 (−1573 bp) and NFκB (−2407 bp and −1035 bp). Besides one binding site each for transcription factors III-A and C/EBP-d, there are two sites for NF-IL6/C-EBP-β, seven sites for GMCSF, nine sites for γ-IRE, two sites for activator protein (AP)-1, eight sites for AP-2 and one site for AP-3.

Functional analysis of human Stat6 promoter. To confirm that the isolated Kpn I-Sal I DNA fragment indeed contained a functional promoter, reporter gene constructs were prepared by inserting the 5'-flanking region as a Nhe I-Sal I fragment (approximately −5200 bp to +134 bp, designated pBP78) upstream of the firefly luciferase gene in the pGL3-Basic vector. To identify the minimal promoter region required for the maximal reporter activity, sequential 5'-deletion constructs of pBP78 were engineered. After transient transfection into NIH 3T3 cells, a significant level of transcriptional activity was observed. Maximal luciferase activity was observed with the plasmid pBP86, indicating that this region (−1081 to +134) of the human Stat6 gene was sufficient to achieve maximal luciferase activity. Similar results were obtained when this set of constructs was transfected into HepG2 cells. The parental vector produced only trace amounts of transcriptional activity. These results established that the 5'-flanking region of the Stat6 contained a promoter that is constitutively active in fibroblast and epithelial cell types.

Chromosomal localization of the human Stat6 gene. The chromosomal location of the human Stat6 gene was investigated to determine potential linkage with disease. In two FISH experiments with lymphocytes from different individuals, the majority of the chromosomes had specific fluorescent signals at identical sites on both chromatids of chromosome 12. From a total of 100 metaphases examined, 90 had fluorescent signals on chromosome 12 and 85 had both homologues of chromosome 12 labeled. Double fluorescent labels were not observed at any other site and the five single signals also detected were randomly distributed over different chromosomes. A single specific site of hybridization for the gene unequivocally demonstrates a single locus for this gene. The location of the fluorescent signal was determined directly in 50 metaphases with DAPI enhanced G-like banding at region 12q13.3–12q14.1, where the locus of the human Stat6 gene was assigned.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Paul, W. E. (1991) *Blood* 77, 1859–1870.
4. Noelle, R., Krammer, P. H., Ohara, J., Uhr, J. W., and Vitetta, E. S. (1984) *Proc. Natl. Acad. Sci. USA* 81, 6149–6153.
5. Conrad, D. H., Waldschmidt, T., Lee, W. T., Rao, M., Keegan, A. D., Noelle, R. J., Lynch, R. G., and Kehry, M. R. (1987) *J. Immunol.* 139, 2290–2296.
11. Izuhara, K., and Harada, N. (1993) *J. Biol. Chem.* 268, 13097–13102.
12. Wang, L.-M., Keegan, A. D., Paul, W. E., Heidaran, M. A., Gutkind, J. S., and Pierce, J. H. (1992) *EMBO J.* 11, 4899–4908.
13. Hou, J., Schindler, U., Henzel, W. J., Ho, T. C., Brasseur, M., and McKnight, S. L. (1994) *Science* 165, 1701–1706.
14. Kotanides, H., and Reich, N. C. (1993) *Science* 262, 1265–1267.
15. Johnston, J. A., Kawamura, M., Kirken, R. A., Chen, Y. Q., Blake, T. B., Shibuya, K., Ortaldo, J. R., McVicar, D. W., and O'Shea, J. J. (1994) *Nature* 370, 151–153.
16. Witthuhn, B. A., Silvennoinen, O., Miura, O., Lai, K. S., Cwik, C., Liu, E. T., and Ihle, J. N. (1994) *Nature* 370, 153–157.
17. Wang, L. M., Myers, M. G., Sun, X. J., Aaronson, S. A., White, M., and Pierce, J. H. (1993) *Science* 261, 1591–1594.
18. Wang, L. M., Keegan, A. D., Li, W., Lienhard, G. E., Pacini, S., Gutkind, J. S., Myers, M. G., Sun, X. J., White, M. F., Aaronson, S. A., Paul, W. E., and Pierce, J. H. (1993) *Proc. Natl. Acad. Sci. USA* 90, 4032–4036.
19. Quelle, F. W., Shimoda, K., Thierfelder, W., Fischer, C., Kim, A., Ruben, S. M., Cleveland, J. L., Pierce, J. H., Keegan, A. D., Nelms, K., Paul, W. E., and Ihle, J. N. (1995) *Mol. and Cell. Biol.* 15, 3336–3343.
20. Schindler, C., Kashleva, H., Pernis, A., Pine, R., and Rothman, P. (1994) *EMBO J.* 13, 1350–1356.
22. Pernis, A., Witthuhn, B., Keegan, A. D., Nelms, K., Garfein, E., Ihle, J. N., Paul, W. E., Pierce, J. H., and Rothman, P. (1995) *Proc. Natl. Acad. Sci. USA* 92, 7971–7975.
25. Malabarba, M. G., Rui, H., Deutsch, H. H., Chung, J., Kalthoff, F. S., Farrar, W. L., and Kirken, R. A. (1996) *Biochem. J.* 319, 865–872.
26. Patel, B. K. R., Wang, L. M., Lee, C. C., Taylor, W. G., Pierce, J. H., and LaRochelle, W. J. (1996) *J. Biol. Chem.* 21, 22175–22182.
27. Kaplan, M. H., Schindler, U., Smiley, S. T., and Grusby, M. J. (1996) *Immunity* 4, 1–20.
28. Shimoda, K., Deursen, J., Sangster, M. Y., Sarawar, S. R., Carson, R. T., Tripp, R. A., Chu, C., Quelle, F. W., Nosaka, T., Vignali, D. A. A., Doherty, P. C., Grosveld, G., Paul, W. E., and Ihle, J. N. (1996) *Nature* 380, 630–633.
29. Takeda, K., Tanaka, T., Shi, W., Matsumoto, M., Minami, M., Kashiwamura, S., Nakanishi, K., Yoshida, N., Kishimoto, T., and Akira, S. (1996) *Nature* 380, 627–630.
30. Michieli, P., Li, W., Lorenzi, M. V., Miki, T., Zakut, R., Givol, D., and Pierce, J. H. (1996) *Oncogene* 12, 775–784.
38. Hou, et al. "An Interleukin-4 Induced Transcription Factor: IL-4 Stat" *Science* 265(5179): 1701–6 (Sep. 16, 1994).
39. Lewin, "Genes V" Oxford University Press Chapter 7, pp. 171–174 (1994).
40. Sambrook et al., *Molecular Cloning: A Laboratory Manual.* 2nd Ed., Cold Spring Harbor Laboratory, Cold Spring Harbor, N.Y. (1989).
41. Lewin, "Genes V" Oxford University Press Chapter 1, pp. 9–13 (1994).
42. Kohler, G. et al., "Continuous cultures of fused cells secreting antibody of predefined specificity." *Nature* 256: 495–497 (1975).
43. Popescu, N., Zimonjic, D., Hatch, C., and Bonner, W.: (1994) Chromosomal mapping of the human histone gene H2AZ to 4q24 by fluorescence in situ hybridization. *Genomics*, 20: 333–335.
44. Kunkel et al., *Methods Enzymol.* 154:367 (1987).
45. Mitani et al. "Transduction of human bone marrow by adenoviral vector." *Human Gene Therapy* 5:941–948 (1994).
46. Goodman et al. "Recombinant adeno-associated virus-mediated gene transfer into hematopoietic progenitor cells." *Blood* 84:1492–1500 (1994).
47. Naidini et al. "In vivo gene delivery and stable transduction of nondividing cells by a lentiviral vector." *Science* 272:263–267 (1996).
48. Agrawal et al. "Cell-cycle kinetics and VSV-G pseudotyped retrovirus mediated gene transfer in blood-derived $CD34^+$ cells." *Exp. Hematol.* 24:738–747 (1996).
49. Schwarzenberger et al. "Targeted gene transfer to human hematopoietic progenitor cell lines through the c-kit receptor." *Blood* 87:472–478 (1996).
50. Pastan et al. "A retrovirus carrying an MDR1 cDNA confers multidrug resistance and polarized expression of P-glycoprotein in MDCK cells." *Proc. Nat. Acad. Sci.* 85:4486 (1988).
51. Miller et al. "Redesign of retrovirus packaging cell lines to avoid recombination leading to helper virus production." *Mol. Cell. Biol.* 6:2895 (1986).
52. Martin, E. W. (ed.) Remington's Pharmaceutical Sciences, latest edition. Mack Publishing Co., Easton, Pa.
53. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.
54. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.
55. Zimonjic, D. B, Rezanka, L., DiPaolo, J. A., Popescu, N. C.: (1995) Refined localization of the erbB-3 proto-oncogene by direct visualization of FISH Signals on LUT-inverted and contrast-enhanced digital images of DAPI-banded chromosomes. *Cancer Genetics & Cytogenetics* 80: 100–102.
56. Beeler, J. F. et al. (1997). Cloning and characterization of the human A6 gene. *Gene* 193:31–37.
57. Moss, B. 1991. Vaccinia virus: A tool for research and vaccine development. *Science* 252:1662–1667.

TABLE I

CONSERVATIVE SUBSTITUTIONS

| Shared properties | Amino acids which are interchangeable for each other |
|---|---|
| Neutral and hydrophobic | Alanine (Ala A); Valine (Val V); Leucine (Leu L); Isoleucine (Ile I); Proline (Pro P); Tryptophan (Trp W); Phenylalanine (Phe F); Methionine (Met M) |
| Neutral and polar | Glycine (Gly G); Serine (Ser S); Threonine (Thr T); Tyrosine (Tyr Y); Cysteine (Cys C); Glutamine (Gln Q); Asparagine (Asn N) |
| Basic | Lysine (Lys K); Arginine (Arg R); Histidine (His H) |
| Acidic | Aspartic Acid (Asp D); Glutamic Acid (Glu E) |

TABLE II

| Exon Number | Exon | SEQ ID NO: | Number of Amino Acids | Intron and its size (bases) | SEQ ID NO: |
|---|---|---|---|---|---|
| 1 | 1-AGCCAC . . . GCCGAG-229 | 16 | 0 | gtgagg . . . ggctag (1021) | 17 |
| 2 | 230-AGAAAG . . . GCTGGG-297 | 18 | 0 | gtaagt . . . ctccag (1744) | 19 |
| 3 | 298-GCAACC . . . GCCCTG-434 | 20 | 38 2/3 | gtgagt . . . tgcaag (414) | 21 |
| 4 | 435-GGAGTT . . . CTTGAG-573 | 22 | 46 | gtgggg . . . ctgtag (290) | 23 |
| 5 | 574-AGCATA . . . GAACAG-657 | 24 | 28 | gtattg . . . gtgtag (399) | 25 |
| 6 | 658-TTCCGC . . . GCCAAG-796 | 26 | 46 1/3 | gtgggg . . . cctcag (112) | 27 |
| 7 | 797-TGTCTC . . . AGTGAG-849 | 28 | 17 | gtgagt . . . ccatag (187) | 29 |
| 8 | 850-GCCCTG . . . GGAGAG-998 | 30 | 49 2/3 | gttggg . . . cccag (592) | 31 |
| 9 | 999-GTGTGA . . . CACCAG-1130 | 32 | 43 2/3 | gtattc . . . tcccag (128) | 33 |
| 10 | 1131-TTGCTT . . . TGGAGC-1319 | 34 | 62 2/3 | gtaagc . . . gggcag (338) | 35 |
| 11 | 1320-AGAAAG . . . AACCTG-1407 | 36 | 29 | gtgagg . . . ccacag (139) | 37 |
| 12 | 1408-CTTCTC . . . CTCCAG-1530 | 38 | 41 | gtgaac . . . cttcag (~1450) | 39 |
| 13 | 1531-GCCCTG . . . GAGATG-1623 | 40 | 30 2/3 | gtgagg . . . cccag (334) | 41 |
| 14 | 1624-GACCGC . . . AACAAG-1830 | 42 | 69 | gttcag . . . ccctag (~4150) | 43 |
| 15 | 1831-GAGATC . . . TGACCG-1925 | 44 | 31 2/3 | gtgagt . . . ggccag (92) | 45 |
| 16 | 1926-GCTGAT . . . AGGATG-2062 | 46 | 45 1/3 | gtgagg . . . ccatag (325) | 47 |
| 17 | 2063-GCTCTC . . . ACAAGC-2209 | 48 | 48 1/3 | gtgagc . . . gaacag (227) | 49 |
| 18 | 2210-CTGAAC . . . GGAAAG-2273 | 50 | 20 2/3 | gtgagt . . . ctccag (112) | 51 |
| 19 | 2274-GGACCA . . . TATGGT-2384 | 52 | 36 2/3 | gtaagg . . . cccag (194) | 53 |
| 21 | 2385-GCCCCA . . . CCAGGA-2477 | 54 | 30 2/3 | gtaagt . . . ttccag (1375) | 55 |
| 21 | 2478-GCCTCA . . . CCCCCA-2544 | 56 | 22 | gtgaat . . . tggcag (89) | 57 |
| 22 | 2545-GGCCTG . . . CACTTG-2673 | 58 | 42 2/3 | gtgagt . . . ttgcag (88) | 59 |
| 23 | 2674-GATTGG . . . AATCTG-4018 | 60 | 62 | aaaagaaaga (>300) | 61 |

What is claimed is:

1. An isolated Stat polypeptide having an amino acid sequence of Stat6 (SEQ ID NO:68) wherein at least 110 amino acids are deleted from the amino terminus, said Stat polypeptide having the ability to enhance IL-4 induced Stat6 DNA binding activity.

2. An isolated polypeptide, Stat6b, having an amino acid sequence of Stat6 (SEQ ID NO:68) wherein amino acids 39–86 are deleted at the amino terminus.

3. An isolated polypeptide, Stat6b, having the amino acid sequence of SEQ ID NO:2.

4. An isolated nucleic acid molecule encoding a Stat polypeptide, wherein said Stat polypeptide has the amino acid sequence of Stat6 (SEQ ID NO:68) having at least 110 amino acids deleted at the amino terminus, said Stat polypeptide having the ability to enhance IL-4 induced Stat6 DNA binding activity.

5. An isolated nucleic acid molecule encoding the Stat6b polypeptide, wherein said nucleic acid molecule comprises a deletion of the last base pair of codon 39 of Stat6 and continuing through codon 86 of Stat6 (SEQ ID NO: 67), inclusive.

6. An isolated nucleic acid encoding the polypeptide Stat6b, having the nucleotide sequence of SEQ ID NO:1.

7. A vector comprising the nucleic acid of claim 4.

8. A vector comprising the nucleic acid of claim 5.

9. A vector comprising the nucleic acid of claim 6.

10. A cell comprising the vector of claim 7.

11. A cell comprising the vector of claim 8.

12. A cell comprising the vector of claim 9.

13. A method for producing a Stat polypeptide, said method comprising culturing the cells of claim 10 under conditions whereby the Stat polypeptide is produced.

14. The method of claim 13, said method further comprising the step of purifying the Stat polypeptide from the cells.

15. A method for producing a Stat6b polypeptide, said method comprising culturing the cells of claim 11 under conditions whereby the Stat6b polypeptide is produced.

16. The method of claim 15, said method further comprising the step of purifying the Stat6b polypeptide from the cells.

17. A method for producing a Stat6b polypeptide, said method comprising culturing the cells of claim 12 under conditions whereby the Stat6b polypeptide is produced.

18. The method of claim 17, said method further comprising the step of purifying the Stat6b polypeptide from the cells.

19. An isolated polypeptide, Stat6c, having an amino acid sequence of Stat6 (SEQ ID NO:68) wherein amino acids 357–564 are deleted.

20. An isolated polypeptide, Stat6c, having the amino acid sequence of SEQ ID NO:4.

21. An isolated nucleic acid encoding the polypeptide Stat6c, having an amino acid sequence of Stat6 (SEQ ID NO:68), wherein amino acids 537–564 are deleted.

22. The nucleic acid of claim 21, wherein a deletion in the nucleic acid is present, encompassing the last base pair of codon 536 of Stat6 and continuing through the first two base pairs of codon 564 of Stat6 (SEQ ID NO:67), inclusive.

23. An isolated nucleic acid encoding the polypeptide Stat6c, having the nucleotide sequence of SEQ ID NO:3.

24. A vector comprising the nucleic acid of claim 21.

25. A vector comprising the nucleic acid of claim 22.

26. A vector comprising the nucleic acid of claim 23.

27. A cell comprising the vector of claim 24.

28. A cell comprising the vector of claim 25.

29. A cell comprising the vector of claim 26.

30. A method for producing a Stat6c polypeptide, said method comprising culturing the cells of claim 27 under conditions whereby the Stat6c polypeptide is produced.

31. The method of claim 30, said method further comprising the step of purifying the Stat6c polypeptide from the cells.

32. A method for producing a Stat6c polypeptide, said method comprising culturing the cells of claim 28 under conditions whereby the Stat6c polypeptide is produced.

33. The method of claim 32, said method further comprising the step of purifying the Stat6c polypeptide from the cells.

34. A method for producing a Stat6c polypeptide, said method comprising culturing the cells of claim 29 under conditions whereby the Stat6c polypeptide is produced.

35. The method of claim 34, said method further comprising the step of purifying the Stat6c polypeptide from the cells.

* * * * *

SEQUENCE LISTING

<160> NUMBER OF SEQ ID NOS: 70

<210> SEQ ID NO 1
<211> LENGTH: 3667
<212> TYPE: DNA
<213> ORGANISM: Artificial Sequence
<220> FEATURE:
<223> OTHER INFORMATION: Description of artificial Sequence:/Note - synthetic construct
<221> NAME/KEY: CDS
<222> LOCATION: (286)...(2496)

<400> SEQUENCE: 1
gacagagcta cagacctatg gggcctggaa gtgcccgctg agaaagggag aagacagcag        60
aggggttgcc gaggcaacct ccaagtccca gatcatgtct ctgtggggtc tggtctccaa       120

```
gatgccccca gaaaaagtgc agcggctcta tgtcgacttt ccccaacacc tgcggcatct      180
tctgggtgac tggctggaga gccagccctg agcatatatc agagggaccc cctgaagctg      240
gtggccactt tcagacaaat acttcaagga gagaaaaaag ctgtt atg gaa cag ttc      297
                                                  Met Glu Gln Phe
                                                  1 cgc cac ttg cca atg cct ttc cac tgg aag cag gaa gaa ctc aag ttt        345
Arg His Leu Pro Met Pro Phe His Trp Lys Gln Glu Glu Leu Lys Phe
 5               10                  15                      20 aag aca ggc ttg cgg agg ctg cag cac cga gta ggg gag atc cac ctt        393
Lys Thr Gly Leu Arg Arg Leu Gln His Arg Val Gly Glu Ile His Leu
                 25                  30                  35 ctc cga gaa gcc ctg cag aag ggg gct gag gct ggc caa gtg tct ctg        441
Leu Arg Glu Ala Leu Gln Lys Gly Ala Glu Ala Gly Gln Val Ser Leu
             40                  45                  50 cac agc ttg ata gaa act cct gct aat ggg act ggg cca agt gag gcc        489
His Ser Leu Ile Glu Thr Pro Ala Asn Gly Thr Gly Pro Ser Glu Ala
         55                  60                  65 ctg gcc atg cta ctg cag gag acc act gga gag cta gag gca gcc aaa        537
Leu Ala Met Leu Leu Gln Glu Thr Thr Gly Glu Leu Glu Ala Ala Lys
     70                  75                  80 gcc cta gtg ctg aag agg atc cag att tgg aaa cgg cag cag cag ctg        585
Ala Leu Val Leu Lys Arg Ile Gln Ile Trp Lys Arg Gln Gln Gln Leu
 85                  90                  95                     100 gca ggg aat ggc gca ccg ttt gag gag agc ctg gcc cca ctc cag gag        633
Ala Gly Asn Gly Ala Pro Phe Glu Glu Ser Leu Ala Pro Leu Gln Glu
                105                 110                 115 agg tgt gaa agc ctg gtg gac att tat tcc cag cta cag cag gag gta        681
Arg Cys Glu Ser Leu Val Asp Ile Tyr Ser Gln Leu Gln Gln Glu Val
            120                 125                 130 ggg gcg gct ggt ggg gag ctt gag ccc aag acc cgg gca tcg ctg act        729
Gly Ala Ala Gly Gly Glu Leu Glu Pro Lys Thr Arg Ala Ser Leu Thr
        135                 140                 145 ggc cgg ctg gat gaa gtc ctg aga acc ctc gtc acc agt tgc ttc ctg        777
Gly Arg Leu Asp Glu Val Leu Arg Thr Leu Val Thr Ser Cys Phe Leu
    150                 155                 160 gtg gag aag cag ccc ccc cag gta ctg aag act cag acc aag ttc cag        825
Val Glu Lys Gln Pro Pro Gln Val Leu Lys Thr Gln Thr Lys Phe Gln
165                 170                 175                 180 gct gga gtt cga ttc ctg ttg ggc ttg agg ttc ctg ggg gcc cca gcc        873
Ala Gly Val Arg Phe Leu Leu Gly Leu Arg Phe Leu Gly Ala Pro Ala
                185                 190                 195 aag cct ccg ctg gtc agg gcc gac atg gtg aca gag aag cag gcg cgg        921
Lys Pro Pro Leu Val Arg Ala Asp Met Val Thr Glu Lys Gln Ala Arg
            200                 205                 210 gag ctg agt gtg cct cag ggt cct ggg gct gga gca gaa agc act gga        969
Glu Leu Ser Val Pro Gln Gly Pro Gly Ala Gly Ala Glu Ser Thr Gly
        215                 220                 225 gaa atc atc aac aac act gtg ccc ttg gag aac agc att cct ggg aac        1017
Glu Ile Ile Asn Asn Thr Val Pro Leu Glu Asn Ser Ile Pro Gly Asn
    230                 235                 240 tgc tgc tct gcc ctg ttc aag aac ctg ctt ctc aag aag atc aag cgg        1065
Cys Cys Ser Ala Leu Phe Lys Asn Leu Leu Leu Lys Lys Ile Lys Arg
245                 250                 255                 260 tgt gag cgg aag ggc act gag tct gtc aca gag gag aag tgc gct gtg        1113
Cys Glu Arg Lys Gly Thr Glu Ser Val Thr Glu Glu Lys Cys Ala Val
                265                 270                 275 ctc ttc tct gcc agc ttc aca ctt ggc ccc ggc aaa ctc ccc atc cag        1161
Leu Phe Ser Ala Ser Phe Thr Leu Gly Pro Gly Lys Leu Pro Ile Gln
            280                 285                 290
```

```
ctc cag gcc ctg tct ctg ccc ctg gtg gtc atc gtc cat ggc aac caa    1209
Leu Gln Ala Leu Ser Leu Pro Leu Val Val Ile Val His Gly Asn Gln
            295                 300                 305 gac aac aat gcc aaa gcc act atc ctg tgg gac aat gcc ttc tct gag    1257
Asp Asn Asn Ala Lys Ala Thr Ile Leu Trp Asp Asn Ala Phe Ser Glu
    310                 315                 320 atg gac cgc gtg ccc ttt gtg gtg gct gag cgg gtg ccc tgg gag aag    1305
Met Asp Arg Val Pro Phe Val Val Ala Glu Arg Val Pro Trp Glu Lys
325                 330                 335                 340 atg tgt gaa act ctg aac ctg aag ttc atg gct gag gtg ggg acc aac    1353
Met Cys Glu Thr Leu Asn Leu Lys Phe Met Ala Glu Val Gly Thr Asn
                345                 350                 355 cgg ggg ctg ctc cca gag cac ttc ctc ttc ctg gcc cag aag atc ttc    1401
Arg Gly Leu Leu Pro Glu His Phe Leu Phe Leu Ala Gln Lys Ile Phe
            360                 365                 370 aat gac aac agc ctc agt atg gag gcc ttc cag cac cgt tct gtg tcc    1449
Asn Asp Asn Ser Leu Ser Met Glu Ala Phe Gln His Arg Ser Val Ser
        375                 380                 385 tgg tcg cag ttc aac aag gag atc ctg ctg ggc cgt ggc ttc acc ttt    1497
Trp Ser Gln Phe Asn Lys Glu Ile Leu Leu Gly Arg Gly Phe Thr Phe
    390                 395                 400 tgg cag tgg ttt gat ggt gtc ctg gac ctc acc aaa cgc tgt ctc cgg    1545
Trp Gln Trp Phe Asp Gly Val Leu Asp Leu Thr Lys Arg Cys Leu Arg
405                 410                 415                 420 agc tac tgg tct gac cgg ctg atc att ggc ttc atc agc aaa cag tac    1593
Ser Tyr Trp Ser Asp Arg Leu Ile Ile Gly Phe Ile Ser Lys Gln Tyr
                425                 430                 435 gtt act agc ctt ctt ctc aat gag ccc gac gga acc ttt ctc ctc cgc    1641
Val Thr Ser Leu Leu Leu Asn Glu Pro Asp Gly Thr Phe Leu Leu Arg
            440                 445                 450 ttc agc gac tca gag att ggg ggc atc acc att gcc cat gtc atc cgg    1689
Phe Ser Asp Ser Glu Ile Gly Gly Ile Thr Ile Ala His Val Ile Arg
        455                 460                 465 ggc cag gat ggc tct cca cag ata gag aac atc cag cca ttc tct gcc    1737
Gly Gln Asp Gly Ser Pro Gln Ile Glu Asn Ile Gln Pro Phe Ser Ala
    470                 475                 480 aaa gac ctg tcc att cgc tca ctg ggg gac cga atc cgg gat ctt gct    1785
Lys Asp Leu Ser Ile Arg Ser Leu Gly Asp Arg Ile Arg Asp Leu Ala
485                 490                 495                 500 cag ctc aaa aat ctc tat ccc aag aag ccc aag gat gag gct ttc cgg    1833
Gln Leu Lys Asn Leu Tyr Pro Lys Lys Pro Lys Asp Glu Ala Phe Arg
                505                 510                 515 agc cac tac aag cct gaa cag atg ggt aag gat ggc agg ggt tat gtc    1881
Ser His Tyr Lys Pro Glu Gln Met Gly Lys Asp Gly Arg Gly Tyr Val
            520                 525                 530 cca gct acc atc aag atg acc gtg gaa agg gac caa cca ctt cct acc    1929
Pro Ala Thr Ile Lys Met Thr Val Glu Arg Asp Gln Pro Leu Pro Thr
        535                 540                 545 cca gag ctc cag atg cct acc atg gtg cct tct tat gac ctt gga atg    1977
Pro Glu Leu Gln Met Pro Thr Met Val Pro Ser Tyr Asp Leu Gly Met
    550                 555                 560 gcc cct gat tcc tcc atg agc atg cag ctt ggc cca gat atg gtg ccc    2025
Ala Pro Asp Ser Ser Met Ser Met Gln Leu Gly Pro Asp Met Val Pro
565                 570                 575                 580 cag gtg tac cca cca cac tct cac tcc atc ccc ccg tat caa ggc ctc    2073
Gln Val Tyr Pro Pro His Ser His Ser Ile Pro Pro Tyr Gln Gly Leu
                585                 590                 595 tcc cca gaa gaa tca gtc aac gtg ttg tca gcc ttc cag gag cct cac    2121
Ser Pro Glu Glu Ser Val Asn Val Leu Ser Ala Phe Gln Glu Pro His
```

```
                       600                  605                  610
ctg cag atg ccc ccc agc ctg ggc cag atg agc ctg ccc ttt gac cag     2169
Leu Gln Met Pro Pro Ser Leu Gly Gln Met Ser Leu Pro Phe Asp Gln
            615                  620                  625 cct cac ccc cag ggc ctg ctg ccg tgc cag cct cag gag cat gct gtg     2217
Pro His Pro Gln Gly Leu Leu Pro Cys Gln Pro Gln Glu His Ala Val
        630                  635                  640 tcc agc cct gac ccc ctg ctc tgc tca gat gtg acc atg gtg gaa gac     2265
Ser Ser Pro Asp Pro Leu Leu Cys Ser Asp Val Thr Met Val Glu Asp
645                  650                  655                  660 agc tgc ctg agc cag cca gtg aca gcg ttt cct cag ggc act tgg att     2313
Ser Cys Leu Ser Gln Pro Val Thr Ala Phe Pro Gln Gly Thr Trp Ile
                665                  670                  675 ggt gaa gac ata ttc cct cct ctg ctg cct ccc act gaa cag gac ctc     2361
Gly Glu Asp Ile Phe Pro Pro Leu Leu Pro Pro Thr Glu Gln Asp Leu
            680                  685                  690 act aag ctt ctc ctg gag ggg caa ggg gag tcg ggg gga ggg tcc ttg     2409
Thr Lys Leu Leu Leu Glu Gly Gln Gly Glu Ser Gly Gly Gly Ser Leu
        695                  700                  705 ggg gca cag ccc ctc ctg cag ccc tcc cac tat ggg caa tct ggg atc     2457
Gly Ala Gln Pro Leu Leu Gln Pro Ser His Tyr Gly Gln Ser Gly Ile
710                  715                  720 tca atg tcc cac atg gac cta agg gcc aac ccc agt tgg tgatcccagc     2506
Ser Met Ser His Met Asp Leu Arg Ala Asn Pro Ser Trp
725                  730                  735 tggagggaga acccaaagag acagctcttc tactaccccc acagacctgc tctggacact   2566
tgctcatgcc ctgccaagca gcagatgggg agggtgccct cctatcccca cctactcctg   2626
ggtcaggagg aaaagactaa caggagaatg cacagtgggt ggagccaatc cactccttcc   2686
tttctatcat tcccctgccc acctccttcc agcactgact ggaagggaag ttcaggctct   2746
gagacacgcc ccaacatgcc tgcacctgca gcgcgcacac gcacgcacac acacatacag   2806
agctctctga gggtgatggg gctgagcagg aggggggctg ggtaagagca caggttaggg   2866
catggaaggc ttctccgccc attctgaccc agggcctagg acggataggc aggaacatac   2926
agacacattt acactagagg ccagggatag aggatattgg gtctcagccc tagggggaatg  2986
ggaagcagct caagggaccc tgggtgggag cataggagga gtctggacat gtggttacta   3046
gtacaggttt tgccctgatt aaaaaatctc ccaaagcccc aaattcctgt tagccaggtg   3106
gaggcttctg atacgtgtat gagactatgc aaaagtacaa gggctgagat tcttcgtgta   3166
tagctgtgtg aacgtgtatg tacctaggat atgttaaata tatagctggc accttagttg   3226
catgaccaca tagaacatgt gtctatctgc ttttgcctac gtgacaacac aaatttggga   3286
gggtgagaca ctgcacagaa gacagcagca agtgtgctgg cctctctgac atatgctaac   3346
ccccaaatac tctgaatttg gagtctgact gtgcccaagt gggtccaagt ggctgtgaca   3406
tctacgtatg gctccacacc tccaatgctg cctgggagcc agggtgagag tctgggtcca   3466
ggcctggcca tgtggccctc cagtgtatga gagggccctg cctgctgcat cttttctgtt   3526
gccccatcca ccgccagctt cccttcactc ccctatccca ttctccctct caaggcaggg   3586
gtcatagatc ctaagccata aaataaattt tattccaaaa taaaaaaaaa aaaaaaaaa    3646
aaaaaaaaa  aaaaaaaaa a                                              3667
```

<210> SEQ ID NO 2
<211> LENGTH: 737
<212> TYPE: PRT
<213> ORGANISM: Artificial Sequence
<220> FEATURE:
<223> OTHER INFORMATION: Description of artificial Sequence:/Note - synthetic construct

<400> SEQUENCE: 2

```
Met Glu Gln Phe Arg His Leu Pro Met Pro Phe His Trp Lys Gln Glu
 1               5                  10                  15
Glu Leu Lys Phe Lys Thr Gly Leu Arg Arg Leu Gln His Arg Val Gly
            20                  25                  30
Glu Ile His Leu Leu Arg Glu Ala Leu Gln Lys Gly Ala Glu Ala Gly
        35                  40                  45
Gln Val Ser Leu His Ser Leu Ile Glu Thr Pro Ala Asn Gly Thr Gly
    50                  55                  60
Pro Ser Glu Ala Leu Ala Met Leu Leu Gln Glu Thr Thr Gly Glu Leu
65                  70                  75                  80
Glu Ala Ala Lys Ala Leu Val Leu Lys Arg Ile Gln Ile Trp Lys Arg
                85                  90                  95
Gln Gln Gln Leu Ala Gly Asn Gly Ala Pro Phe Glu Glu Ser Leu Ala
            100                 105                 110
Pro Leu Gln Glu Arg Cys Glu Ser Leu Val Asp Ile Tyr Ser Gln Leu
        115                 120                 125
Gln Gln Glu Val Gly Ala Ala Gly Gly Glu Leu Glu Pro Lys Thr Arg
    130                 135                 140
Ala Ser Leu Thr Gly Arg Leu Asp Glu Val Leu Arg Thr Leu Val Thr
145                 150                 155                 160
Ser Cys Phe Leu Val Glu Lys Gln Pro Pro Gln Val Leu Lys Thr Gln
                165                 170                 175
Thr Lys Phe Gln Ala Gly Val Arg Phe Leu Leu Gly Leu Arg Phe Leu
            180                 185                 190
Gly Ala Pro Ala Lys Pro Pro Leu Val Arg Ala Asp Met Val Thr Glu
        195                 200                 205
Lys Gln Ala Arg Glu Leu Ser Val Pro Gln Gly Pro Gly Ala Gly Ala
    210                 215                 220
Glu Ser Thr Gly Glu Ile Ile Asn Asn Thr Val Pro Leu Glu Asn Ser
225                 230                 235                 240
Ile Pro Gly Asn Cys Cys Ser Ala Leu Phe Lys Asn Leu Leu Leu Lys
                245                 250                 255
Lys Ile Lys Arg Cys Glu Arg Lys Gly Thr Glu Ser Val Thr Glu Glu
            260                 265                 270
Lys Cys Ala Val Leu Phe Ser Ala Ser Phe Thr Leu Gly Pro Gly Lys
        275                 280                 285
Leu Pro Ile Gln Leu Gln Ala Leu Ser Leu Pro Leu Val Val Ile Val
    290                 295                 300
His Gly Asn Gln Asp Asn Asn Ala Lys Ala Thr Ile Leu Trp Asp Asn
305                 310                 315                 320
Ala Phe Ser Glu Met Asp Arg Val Pro Phe Val Val Ala Glu Arg Val
                325                 330                 335
Pro Trp Glu Lys Met Cys Glu Thr Leu Asn Leu Lys Phe Met Ala Glu
            340                 345                 350
Val Gly Thr Asn Arg Gly Leu Leu Pro Glu His Phe Leu Phe Leu Ala
        355                 360                 365
Gln Lys Ile Phe Asn Asp Asn Ser Leu Ser Met Glu Ala Phe Gln His
    370                 375                 380
Arg Ser Val Ser Trp Ser Gln Phe Asn Lys Glu Ile Leu Leu Gly Arg
```

```
385                 390                 395                 400

Gly Phe Thr Phe Trp Gln Trp Phe Asp Gly Val Leu Asp Leu Thr Lys
                405                 410                 415

Arg Cys Leu Arg Ser Tyr Trp Ser Asp Arg Leu Ile Ile Gly Phe Ile
            420                 425                 430

Ser Lys Gln Tyr Val Thr Ser Leu Leu Leu Asn Glu Pro Asp Gly Thr
        435                 440                 445

Phe Leu Leu Arg Phe Ser Asp Ser Glu Ile Gly Ile Thr Ile Ala
    450                 455                 460

His Val Ile Arg Gly Gln Asp Gly Ser Pro Gln Ile Glu Asn Ile Gln
465                 470                 475                 480

Pro Phe Ser Ala Lys Asp Leu Ser Ile Arg Ser Leu Gly Asp Arg Ile
                485                 490                 495

Arg Asp Leu Ala Gln Leu Lys Asn Leu Tyr Pro Lys Lys Pro Lys Asp
            500                 505                 510

Glu Ala Phe Arg Ser His Tyr Lys Pro Glu Gln Met Gly Lys Asp Gly
        515                 520                 525

Arg Gly Tyr Val Pro Ala Thr Ile Lys Met Thr Val Glu Arg Asp Gln
    530                 535                 540

Pro Leu Pro Thr Pro Glu Leu Gln Met Pro Thr Met Val Pro Ser Tyr
545                 550                 555                 560

Asp Leu Gly Met Ala Pro Asp Ser Ser Met Ser Met Gln Leu Gly Pro
                565                 570                 575

Asp Met Val Pro Gln Val Tyr Pro Pro His Ser His Ser Ile Pro Pro
            580                 585                 590

Tyr Gln Gly Leu Ser Pro Glu Glu Ser Val Asn Val Leu Ser Ala Phe
        595                 600                 605

Gln Glu Pro His Leu Gln Met Pro Pro Ser Leu Gly Gln Met Ser Leu
    610                 615                 620

Pro Phe Asp Gln Pro His Pro Gln Gly Leu Leu Pro Cys Gln Pro Gln
625                 630                 635                 640

Glu His Ala Val Ser Ser Pro Asp Pro Leu Leu Cys Ser Asp Val Thr
                645                 650                 655

Met Val Glu Asp Ser Cys Leu Ser Gln Pro Val Thr Ala Phe Pro Gln
            660                 665                 670

Gly Thr Trp Ile Gly Glu Asp Ile Phe Pro Pro Leu Leu Pro Pro Thr
        675                 680                 685

Glu Gln Asp Leu Thr Lys Leu Leu Leu Glu Gly Gln Gly Glu Ser Gly
    690                 695                 700

Gly Gly Ser Leu Gly Ala Gln Pro Leu Leu Gln Pro Ser His Tyr Gly
705                 710                 715                 720

Gln Ser Gly Ile Ser Met Ser His Met Asp Leu Arg Ala Asn Pro Ser
                725                 730                 735

Trp

<210> SEQ ID NO 3
<211> LENGTH: 3894
<212> TYPE: DNA
<213> ORGANISM: Artificial Sequence
<220> FEATURE:
<223> OTHER INFORMATION: Description of artificial Sequence:/Note -
      synthetic construct
<221> NAME/KEY: CDS
<222> LOCATION: (231)...(2687)

<400> SEQUENCE: 3
```

```
ttattttct ttttggtggt ggtggtggaa ggggggaggt gctagcaggg ccagccttga    60
actcgctgga cagagctaca gacctatggg gcctggaagt gcccgctgag aaagggagaa  120
gacagcagag gggttgccga gagaaaggcc tattggagga acctgagcag gagggtaag   180 gattctgcct tgaggagaaa agagctgggg caacctccaa gtcccagatc atg tct    236
                                                        Met Ser
                                                         1 ctg tgg ggt ctg gtc tcc aag atg ccc cca gaa aaa gtg cag cgg ctc   284
Leu Trp Gly Leu Val Ser Lys Met Pro Pro Glu Lys Val Gln Arg Leu
     5                  10                  15 tat gtc gac ttt ccc caa cac ctg cgg cat ctt ctg ggt gac tgg ctg   332
Tyr Val Asp Phe Pro Gln His Leu Arg His Leu Leu Gly Asp Trp Leu
 20                  25                  30 gag agc cag ccc tgg gag ttc ctg gtc ggc tcc gac gcc ttc tgc tgc   380
Glu Ser Gln Pro Trp Glu Phe Leu Val Gly Ser Asp Ala Phe Cys Cys
 35                  40                  45                  50 aac ttg gct agt gcc cta ctt tca gac act gtc cag cac ctt cag gcc   428
Asn Leu Ala Ser Ala Leu Leu Ser Asp Thr Val Gln His Leu Gln Ala
                 55                  60                  65 tcg gtg gga gag cag ggg gag ggg agc acc atc ttg caa cac atc agc   476
Ser Val Gly Glu Gln Gly Glu Gly Ser Thr Ile Leu Gln His Ile Ser
         70                  75                  80 acc ctt gag agc ata tat cag agg gac ccc ctg aag ctg gtg gcc act   524
Thr Leu Glu Ser Ile Tyr Gln Arg Asp Pro Leu Lys Leu Val Ala Thr
             85                  90                  95 ttc aga caa ata ctt caa gga gag aaa aaa gct gtt atg gaa cag ttc   572
Phe Arg Gln Ile Leu Gln Gly Glu Lys Lys Ala Val Met Glu Gln Phe
100                 105                 110 cgc cac ttg cca atg cct ttc cac tgg aag cag gaa gaa ctc aag ttt   620
Arg His Leu Pro Met Pro Phe His Trp Lys Gln Glu Glu Leu Lys Phe
115                 120                 125                 130 aag aca ggc ttg cgg agg ctg cag cac cga gta ggg gag atc cac ctt   668
Lys Thr Gly Leu Arg Arg Leu Gln His Arg Val Gly Glu Ile His Leu
                135                 140                 145 ctc cga gaa gcc ctg cag aag ggg gct gag gct ggc caa gtg tct ctg   716
Leu Arg Glu Ala Leu Gln Lys Gly Ala Glu Ala Gly Gln Val Ser Leu
            150                 155                 160 cac agc ttg ata gaa act cct gct aat ggg act ggg cca agt gag gcc   764
His Ser Leu Ile Glu Thr Pro Ala Asn Gly Thr Gly Pro Ser Glu Ala
        165                 170                 175 ctg gcc atg cta ctg cag gag acc act gga gag cta gag gca gcc aaa   812
Leu Ala Met Leu Leu Gln Glu Thr Thr Gly Glu Leu Glu Ala Ala Lys
180                 185                 190 gcc cta gtg ctg aag agg atc cag att tgg aaa cgg cag cag cag ctg   860
Ala Leu Val Leu Lys Arg Ile Gln Ile Trp Lys Arg Gln Gln Gln Leu
195                 200                 205                 210 gca ggg aat ggc gca ccg ttt gag gag agc ctg gcc cca ctc cag gag   908
Ala Gly Asn Gly Ala Pro Phe Glu Glu Ser Leu Ala Pro Leu Gln Glu
                215                 220                 225 agg tgt gaa agc ctg gtg gac att tat tcc cag cta cag cag gag gta   956
Arg Cys Glu Ser Leu Val Asp Ile Tyr Ser Gln Leu Gln Gln Glu Val
            230                 235                 240 ggg gcg gct ggt ggg gag ctt gag ccc aag acc cgg gca tcg ctg act  1004
Gly Ala Ala Gly Gly Glu Leu Glu Pro Lys Thr Arg Ala Ser Leu Thr
        245                 250                 255 ggc cgg ctg gat gaa gtc ctg aga acc ctc gtc acc agt tgc ttc ctg  1052
Gly Arg Leu Asp Glu Val Leu Arg Thr Leu Val Thr Ser Cys Phe Leu
260                 265                 270
```

```
gtg gag aag cag ccc ccc cag gta ctg aag act cag acc aag ttc cag     1100
Val Glu Lys Gln Pro Pro Gln Val Leu Lys Thr Gln Thr Lys Phe Gln
275             280                 285                 290 gct gga gtt cga ttc ctg ttg ggc ttg agg ttc ctg ggg gcc cca gcc     1148
Ala Gly Val Arg Phe Leu Leu Gly Leu Arg Phe Leu Gly Ala Pro Ala
                295                 300                 305 aag cct ccg ctg gtc agg gcc gac atg gtg aca gag aag cag gcg cgg     1196
Lys Pro Pro Leu Val Arg Ala Asp Met Val Thr Glu Lys Gln Ala Arg
            310                 315                 320 gag ctg agt gtg cct cag ggt cct ggg gct gga gca gaa agc act gga     1244
Glu Leu Ser Val Pro Gln Gly Pro Gly Ala Gly Ala Glu Ser Thr Gly
        325                 330                 335 gaa atc atc aac aac act gtg ccc ttg gag aac agc att cct ggg aac     1292
Glu Ile Ile Asn Asn Thr Val Pro Leu Glu Asn Ser Ile Pro Gly Asn
340                 345                 350 tgc tgc tct gcc ctg ttc aag aac ctg ctt ctc aag aag atc aag cgg     1340
Cys Cys Ser Ala Leu Phe Lys Asn Leu Leu Leu Lys Lys Ile Lys Arg
355                 360                 365                 370 tgt gag cgg aag ggc act gag tct gtc aca gag gag aag tgc gct gtg     1388
Cys Glu Arg Lys Gly Thr Glu Ser Val Thr Glu Glu Lys Cys Ala Val
                375                 380                 385 ctc ttc tct gcc agc ttc aca ctt ggc ccc ggc aaa ctc ccc atc cag     1436
Leu Phe Ser Ala Ser Phe Thr Leu Gly Pro Gly Lys Leu Pro Ile Gln
            390                 395                 400 ctc cag gcc ctg tct ctg ccc ctg gtg gtc atc gtc cat ggc aac caa     1484
Leu Gln Ala Leu Ser Leu Pro Leu Val Val Ile Val His Gly Asn Gln
        405                 410                 415 gac aac aat gcc aaa gcc act atc ctg tgg gac aat gcc ttc tct gag     1532
Asp Asn Asn Ala Lys Ala Thr Ile Leu Trp Asp Asn Ala Phe Ser Glu
420                 425                 430 atg gac cgc gtg ccc ttt gtg gtg gct gag cgg gtg ccc tgg gag aag     1580
Met Asp Arg Val Pro Phe Val Val Ala Glu Arg Val Pro Trp Glu Lys
435                 440                 445                 450 atg tgt gaa act ctg aac ctg aag ttc atg gct gag gtg ggg acc aac     1628
Met Cys Glu Thr Leu Asn Leu Lys Phe Met Ala Glu Val Gly Thr Asn
                455                 460                 465 cgg ggg ctg ctc cca gag cac ttc ctc ttc ctg gcc cag aag atc ttc     1676
Arg Gly Leu Leu Pro Glu His Phe Leu Phe Leu Ala Gln Lys Ile Phe
            470                 475                 480 aat gac aac agc ctc agt atg gag gcc ttc cag cac cgt tct gtg tcc     1724
Asn Asp Asn Ser Leu Ser Met Glu Ala Phe Gln His Arg Ser Val Ser
        485                 490                 495 tgg tcg cag ttc aac aag gag atc ctg ctg ggc cgt ggc ttc acc ttt     1772
Trp Ser Gln Phe Asn Lys Glu Ile Leu Leu Gly Arg Gly Phe Thr Phe
500                 505                 510 tgg cag tgg ttt gat ggt gtc ctg gac ctc acc aaa cgc tgt ctc cgg     1820
Trp Gln Trp Phe Asp Gly Val Leu Asp Leu Thr Lys Arg Cys Leu Arg
515                 520                 525                 530 agc tac tgg tct gac cgc gac tca gag att ggg ggc atc acc att gcc     1868
Ser Tyr Trp Ser Asp Arg Asp Ser Glu Ile Gly Gly Ile Thr Ile Ala
                535                 540                 545 cat gtc atc cgg ggc cag gat ggc tct cca cag ata gag aac atc cag     1916
His Val Ile Arg Gly Gln Asp Gly Ser Pro Gln Ile Glu Asn Ile Gln
            550                 555                 560 cca ttc tct gcc aaa gac ctg tcc att cgc tca ctg ggg gac cga atc     1964
Pro Phe Ser Ala Lys Asp Leu Ser Ile Arg Ser Leu Gly Asp Arg Ile
        565                 570                 575 cgg gat ctt gct cag ctc aaa aat ctc tat ccc aag aag ccc aag gat     2012
Arg Asp Leu Ala Gln Leu Lys Asn Leu Tyr Pro Lys Lys Pro Lys Asp
580                 585                 590
```

```
gag gct ttc cgg agc cac tac aag cct gaa cag atg ggt aag gat ggc      2060
Glu Ala Phe Arg Ser His Tyr Lys Pro Glu Gln Met Gly Lys Asp Gly
595                 600                 605                 610 agg ggt tat gtc cca gct acc atc aag atg acc gtg gaa agg gac caa      2108
Arg Gly Tyr Val Pro Ala Thr Ile Lys Met Thr Val Glu Arg Asp Gln
            615                 620                 625 cca ctt cct acc cca gag ctc cag atg cct acc atg gtg cct tct tat      2156
Pro Leu Pro Thr Pro Glu Leu Gln Met Pro Thr Met Val Pro Ser Tyr
        630                 635                 640 gac ctt gga atg gcc cct gat tcc tcc atg agc atg cag ctt ggc cca      2204
Asp Leu Gly Met Ala Pro Asp Ser Ser Met Ser Met Gln Leu Gly Pro
    645                 650                 655 gat atg gtg ccc cag gtg tac cca cca cac tct cac tcc atc ccc ccg      2252
Asp Met Val Pro Gln Val Tyr Pro Pro His Ser His Ser Ile Pro Pro
660                 665                 670 tat caa ggc ctc tcc cca gaa gaa tca gtc aac gtg ttg tca gcc ttc      2300
Tyr Gln Gly Leu Ser Pro Glu Glu Ser Val Asn Val Leu Ser Ala Phe
675                 680                 685                 690 cag gag cct cac ctg cag atg ccc ccc agc ctg ggc cag atg agc ctg      2348
Gln Glu Pro His Leu Gln Met Pro Pro Ser Leu Gly Gln Met Ser Leu
            695                 700                 705 ccc ttt gac cag cct cac ccc cag ggc ctg ctg ccg tgc cag cct cag      2396
Pro Phe Asp Gln Pro His Pro Gln Gly Leu Leu Pro Cys Gln Pro Gln
        710                 715                 720 gag cat gct gtg tcc agc cct gac ccc ctg ctc tgc tca gat gtg acc      2444
Glu His Ala Val Ser Ser Pro Asp Pro Leu Leu Cys Ser Asp Val Thr
    725                 730                 735 atg gtg gaa gac agc tgc ctg agc cag cca gtg aca gcg ttt cct cag      2492
Met Val Glu Asp Ser Cys Leu Ser Gln Pro Val Thr Ala Phe Pro Gln
740                 745                 750 ggc act tgg att ggt gaa gac ata ttc cct cct ctg ctg cct ccc act      2540
Gly Thr Trp Ile Gly Glu Asp Ile Phe Pro Pro Leu Leu Pro Pro Thr
755                 760                 765                 770 gaa cag gac ctc act aag ctt ctc ctg gag ggg caa ggg gag tcg ggg      2588
Glu Gln Asp Leu Thr Lys Leu Leu Leu Glu Gly Gln Gly Glu Ser Gly
            775                 780                 785 gga ggg tcc ttg ggg gca cag ccc ctc ctg cag ccc tcc cac tat ggg      2636
Gly Gly Ser Leu Gly Ala Gln Pro Leu Leu Gln Pro Ser His Tyr Gly
        790                 795                 800 caa tct ggg atc tca atg tcc cac atg gac cta agg gcc aac ccc agt      2684
Gln Ser Gly Ile Ser Met Ser His Met Asp Leu Arg Ala Asn Pro Ser
    805                 810                 815 tgg tgatcccagc tggagggaga acccaaagag acagctcttc tactaccccc           2737
Trp acagacctgc tctggacact tgctcatgcc ctgccaagca gcagatgggg agggtgccct    2797
cctatcccca cctactcctg ggtcaggagg aaaagactaa caggagaatg cacagtgggt    2857
ggagccaatc cactccttcc tttctatcat tcccctgccc acctccttcc agcactgact    2917
ggaagggaag ttcaggctct gagacacgcc caacatgcc tgcacctgca gcgcgcacac     2977
gcacgcacac acacatacag agctctctga gggtgatggg gctgagcagg agggggctg     3037 ggtaagagca caggttaggg catggaaggc ttctccgccc attctgaccc agggcctagg    3097
acggataggc aggaacatac agacacattt acactagagg ccaggatag aggatattgg     3157 gtctcagccc taggggaatg ggaagcagct caagggaccc tggtgggag cataggagga     3217 gtctggacat gtggttacta gtacaggttt tgccctgatt aaaaaatctc ccaaagcccc    3277 aaattccctgt tagccaggtg gaggcttctg atacgtgtat gagactatgc aaaagtacaa   3337
```

-continued

```
gggctgagat tcttcgtgta tagctgtgtg aacgtgtatg tacctaggat atgttaaata      3397
tatagctggc accttagttg catgaccaca tagaacatgt gtctatctgc ttttgcctac      3457
gtgacaacac aaatttggga gggtgagaca ctgcacagaa gacagcagca agtgtgctgg      3517
cctctctgac atatgctaac ccccaaatac tctgaatttg gagtctgact gtgcccaagt      3577
gggtccaagt ggctgtgaca tctacgtatg ctccacacc tccaatgctg cctgggagcc       3637
agggtgagag tctgggtcca ggcctggcca tgtggccctc cagtgtatga gagggccctg      3697
cctgctgcat cttttctgtt gccccatcca ccgccagctt cccttcactc ccctatccca      3757
ttctccctct caaggcaggg gtcatagatc ctaagccata aataaattt tattccaaaa       3817 taacaaaata aataatctac tgtacacaat ctgaaaaaaa aaaaaaaaaa aaaaaaaaa       3877 aaaaaaaaaa aaaaaaa                                                     3894
```

<210> SEQ ID NO 4
<211> LENGTH: 819
<212> TYPE: PRT
<213> ORGANISM: Artificial Sequence
<220> FEATURE:
<223> OTHER INFORMATION: Description of artificial Sequence:/Note - synthetic construct

<400> SEQUENCE: 4

```
Met Ser Leu Trp Gly Leu Val Ser Lys Met Pro Pro Glu Lys Val Gln
 1               5                  10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255
```

```
Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
        290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
            355                 360                 365

Lys Arg Cys Glu Arg Lys Gly Thr Glu Ser Val Thr Glu Glu Lys Cys
            370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
                420                 425                 430

Ser Glu Met Asp Arg Val Pro Phe Val Val Ala Glu Arg Val Pro Trp
            435                 440                 445

Glu Lys Met Cys Glu Thr Leu Asn Leu Lys Phe Met Ala Glu Val Gly
            450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
            515                 520                 525

Leu Arg Ser Tyr Trp Ser Asp Arg Asp Ser Glu Ile Gly Gly Ile Thr
            530                 535                 540

Ile Ala His Val Ile Arg Gly Gln Asp Gly Ser Pro Gln Ile Glu Asn
545                 550                 555                 560

Ile Gln Pro Phe Ser Ala Lys Asp Leu Ser Ile Arg Ser Leu Gly Asp
                565                 570                 575

Arg Ile Arg Asp Leu Ala Gln Leu Lys Asn Leu Tyr Pro Lys Lys Pro
            580                 585                 590

Lys Asp Glu Ala Phe Arg Ser His Tyr Lys Pro Glu Gln Met Gly Lys
            595                 600                 605

Asp Gly Arg Gly Tyr Val Pro Ala Thr Ile Lys Met Thr Val Glu Arg
            610                 615                 620

Asp Gln Pro Leu Pro Thr Pro Glu Leu Gln Met Pro Thr Met Val Pro
625                 630                 635                 640

Ser Tyr Asp Leu Gly Met Ala Pro Asp Ser Ser Met Ser Met Gln Leu
                645                 650                 655

Gly Pro Asp Met Val Pro Gln Val Tyr Pro Pro His Ser His Ser Ile
            660                 665                 670
```

```
Pro Pro Tyr Gln Gly Leu Ser Pro Glu Glu Ser Val Asn Val Leu Ser
            675                 680                 685

Ala Phe Gln Glu Pro His Leu Gln Met Pro Pro Ser Leu Gly Gln Met
        690                 695                 700

Ser Leu Pro Phe Asp Gln Pro His Pro Gln Gly Leu Leu Pro Cys Gln
705                 710                 715                 720

Pro Gln Glu His Ala Val Ser Ser Pro Asp Pro Leu Leu Cys Ser Asp
                725                 730                 735

Val Thr Met Val Glu Asp Ser Cys Leu Ser Gln Pro Val Thr Ala Phe
            740                 745                 750

Pro Gln Gly Thr Trp Ile Gly Glu Asp Ile Phe Pro Pro Leu Leu Pro
        755                 760                 765

Pro Thr Glu Gln Asp Leu Thr Lys Leu Leu Leu Glu Gly Gln Gly Glu
    770                 775                 780

Ser Gly Gly Gly Ser Leu Gly Ala Gln Pro Leu Leu Gln Pro Ser His
785                 790                 795                 800

Tyr Gly Gln Ser Gly Ile Ser Met Ser His Met Asp Leu Arg Ala Asn
                805                 810                 815

Pro Ser Trp

<210> SEQ ID NO 5
<211> LENGTH: 17425
<212> TYPE: DNA
<213> ORGANISM: Artificial Sequence
<220> FEATURE:
<223> OTHER INFORMATION: Description of artificial Sequence:/Note -
      synthetic construct
<221> NAME/KEY: misc_feature
<222> LOCATION: (1)...(17425)
<223> OTHER INFORMATION: n = a, t, c or g

<400> SEQUENCE: 5
tgtagagatg ggatcttgct atgttgccca ggctggtctc gaactcctgg cctccagcaa      60
tcctcctgcc tcagcctccc agagtattgg gattacaggt gtgagccatt gtgcttgatc     120
aagatgctgt tatgggctga gttgtgttcc tcaaaaattc tcttgaagtc ctaatctcaa     180
gtacttcagg acgtgacctt attttgaagg accccttat aggtctttta cagaggtaat      240
taagttaaaa tgaggccatt aggatggggc ctaatgcaat atgactggta tccttgaaaa     300
aaggggaaac ttggagactg acttgcatac aaagagaaca gtgtgtgaac gtgaaaatgg     360
ccaaggaggg aggcctggaa tagagccttc cttcacatcc ctgagaagga atcaatcaat     420
cctgctcagg ttaaccttga tcttggactt ctagcctcca gcatcttgag agatttctgt     480
tgtttaagtc atgcaatatg tagtactttg ttacagcagc cctagcaaac tgatacactc     540
accaaatcga ttttgtgact cactattggg ttgtaaccag cagtacatag acataaagtt     600 atttttcct tacgctttat cttgtgcaat gctgtgtgtg tgtgtgtgtg tgtgtgtgtg      660
tgtgtgtgtg tgtgtgacgg agtcttgttc tgtcaccagg ctggagtgca gtggcttgat     720
ctcggctcac tataatcaca gccttccaga ttcaagtgat ttccctgcct cagcctcctg     780
agtagctggg actacaggcg cgcaccacca cgcccgacta tttttttgta tttttagtag     840
agacggggtt tcaccatgtt ggccaggatg gtctcaatct cctgaccttg tgatctgccc     900
gcctcagcct cccaaagtgc tgggattaca ggcgtgagcc tctcttgtgc aatctttacc     960
accactcaat gggatgtcaa ggtccagggg agggtgatac agtcaccctc acagtcatgc    1020
aggtgcagat gtcattaatg aaggtctgac agaccctgca attgtacaat ctgaagatga    1080
```

-continued

```
gtatctcctt aaatttcata ctctaggcac tttaccctag cctagactct gttgaagtag   1140
gtataactat tattctcatt tgagggattg acacctgatt gtgaacctcc taaatggagt   1200
catacccaag ccagatttgc ctctaaattc tgttttttcc ccttacatca cagtgttccc   1260
attggtatag tcagttacag agggagtaat atatactatt tttctaccag tacttgctcc   1320
tcgccttcct accccctaaa aggagccaaa gtcagagatc acatttactc ttttccctcc   1380
tcctctccaa gtctttgggg acttgtagct ctgacaccct tagatggtga aacctggctt   1440
cacctactgt ctgtggatgt ctgcaggcag agtgggcact caggagcaca tacaaagcac   1500
gtgtgccgtg aacacgtatg tgcacacacc ttgatcctag catggcttgt tggacaagcc   1560
aatggacaga gtccctgcct gccacctcca cccctgctct cccttctctt ccattcactg   1620
tcctgcagac acagcaaaca catacgcaca tacaccctca atatccttt ggcagtaaca    1680 tgacccccaa atctggggac ttctatgtag gatggagacc cttctccttt cctcatacct   1740
ggtttattat gaaccataaa aatagtgcct gacagttact gtgtgtcagg cattgttcta   1800
agccttcaga tgttttactg cattttattc tcacattatg ggttaagact tatttgctcc   1860
attttacaga tgacgagaat gaatcacaga gtaaattgct cagggttgtg tggttagcag   1920
cattagcagg atttgaaccc aagcagcctg tatccacagt ccagtctttt aactgctata   1980
ttttgctgtg ttcaaaccct ctgctgcctg gctgggtcca cacacgtgca ctcatgcaca   2040
gacctgcggg gtagcaaggg atggaggagg aggagctggt tctggaaatc aattcaggca   2100 ccaggggggca gcataggcct agctttggcc cctcagccca gcccctgcta tgggagggag   2160 gagggagta gaaacttcct cccaccgccc ctcagacacc acctcttcca cacaccgggg    2220
ctctcaggtg tccgggagta aaggcctctc tggatccctt ggtctcctcc agctcctccc   2280
ccagcaaaaa ctgcagaacc ctccactagt tatgttgatg actcagaagt tgagcaagac   2340
tgtgtgtgtg tgtgtgtgtg tgtgtgtgtg tgtgtgtgtg tgtgtggt gttgtgattg     2400 caatgggctc tgtttgtgag cctgcctgca cgtgtgtgtg tgtgtgtgtg tgtgtgtgtg   2460
tgtagtcttg tggtcaggga agttgtgcat gtgtgtgttt gtttcttggc gtgtctcagt   2520
gtttacccca gaaacatata ggaacttggc agataggaac acagcagatt cgtattcaaa   2580
cttgcccctt gtgaatctgc aggcagcagc tccggcttgt gctggttccc accacagtct   2640 caggagggt gccctgtgag gagagagcaa agaccagctt cagtccaagg gactcctaga    2700
gtcttccaga attctgagct gaggttcccc tcccccactc cctcccgtca gtggtcacga   2760
gaccgacctc taaggcgttc cctgccggaa gggaggggga cctaggagtt ggctggcatc   2820
gagctccctg gcggcttttt aggtcctccc actggaggga gcgcagagtc cagagggatt   2880 tactttttcct gaggccctgg ggagcccagt cccttgtggg tccaaacccc agcccttggc  2940
agagtttgag tttgggagcc aggcagttag gggtggcaaa tctctgtttg atattgggtg   3000
actttctgga gaaaagctga tgcttttgag ggggacagag taagtggggg tcagcctccc   3060
cccaagcctg gctccagggc ctggaccccca gtcctgatcc cccacgtgtt ccccactcg   3120 gcacaggagg cacacatatt cacccccactt tcttcctctt cctcctccag cccactttct  3180
cttctctgtg tcgtcagagc tccagggagg gacctgggta gaaggagaag ccggaaacag   3240
cgggctgggg cagccactgc ttacactgaa gagggaggac gggagaggag tgtgtgtgtg   3300
tgtgtgtgtg tgtgtgtgta tgtatgtgtg tgctttatct tatttttctt tttggtggtg   3360
gtgttggaag gggggaggtg ctagcaggc cagccttgaa ctcgctggac agagctacag    3420
acctatgggg cctggaagtg cccgctgaga aagggagaag acagcagagg ggttgccgag   3480
```

-continued

```
gtgaggggtt gcctccgagg tgggtgcggg ggcctctatg agtgcatggg ggtggattcg    3540
tgggggagc  tctcgggatc ctccctggc  tgggtggatg gtccccaang agatggtttc    3600
agctantgtt ggtggctggt ggcactgggt tttancagtt tcgaactcct ggaggaactg    3660
ggagggtcca ggcctcanta ctcccctccc ccatgggtca cgttttcaca gcctcacccc    3720
tgcacccca  agggcccatg gaaagtcagg gaaggaggg  gaaggagtgc ccctctgccc    3780
tgagtcgggg gaagtggccg cccctccctg gaaggttgat cgcagagggc agtggatcct    3840
tgttaaaccc ctatcctgcc ctccactaaa ggttcctgtt caagggtgtg gctggggcgt    3900
gagcaagccc cagatgtaga cctcatggtg gcccagacga gggggaattt cccctcaaa    3960
actgctccac gcttggctcg tgtagacgct gagatttccc agcggcggcg ccgaattaac    4020
cctcctcgtg ctgaactggc tccacctccc cgccttgccc ccaccgccac attcacgcat    4080
tgggcaactc agagaagatg ttttaacttt cgatcctgtg gtccacaatg agaggactcg    4140
ggcagatagg ggttgagata agcgagttta ggccaccaag cgggcggacg aggatcccag    4200
accttgcgct tcccttctga gtttgggagg taacactggc cccgcccctc acgccgtggc    4260
tcctcctcc  cttcccttc  aagggctga  agacaaaagg tgccctgtc  ctggtcaagc    4320
caatcgaccc agccttgtta tgggttgggg tggggaaaaa tgagtcctcc tgatggctgg    4380
ggaagaagag gggttggata tttctagcca gggccatgcc aggaggctgg tcactctgca    4440
agggatgca  gaggaaagcg gagcccactc actccagagg accttttctct tcttgggcta   4500
gagaaaggcc tattggagga acctgagcag gaggggtaag gattctgcct tgaggagaaa    4560
agagctgggg taagtgggca ctggaggaaa gaggggcatg aaggtcttgg agcagaaacg    4620
tccagagaag ggacctctcc attttccatc cctctgagag gcctgggaga ggtgagaggc    4680
tgaacgtgca acaggaggac ttgggggttac tgggtttggg gagacctggg gagttgtcat    4740
cccatcctct ccctcatctc tgggagaggg atattatgag aaacgtgaac tgagaggccc    4800
ctgggaaacc actggttacc cagtcctccc tgaacctgga aatggggatg caacccctc    4860
ttctacttcc ctgtccctc  ctctccttc  tacctgtttt cgtctctcat ctttgccttc    4920
tagccctcca gcttcctctc tcttctaggc tcttcctcc  tagcttacta aacccgcctt    4980
ttttccagtc tcttccatcc tcttccttag ttctctctac tttccttttc cacctctcct    5040
ccttcaagtc tcctcccacc ttcccccact tcttaggatg atcagatttg ccctggaag    5100
ggatcctaac aacacagtgc gatggttaat ccccactcag attcaaagcc tgctttccaa    5160
actcacttac tgagtggcct tgggcagagt agagaaactc cttaagcctc agttcttca    5220
tctataaaat gggatattat atattttaaa aagtgtcgtg aggcctgaag gagataatac    5280
actgagtgta atgcctcata cacagtaagt gcttaacaaa tagtagctgt tattactctc    5340
ccatcctctt catcatctag ccttgtggtt ttcattttta ttttatttca tttatttatt    5400
tatttatttt gagcagagtc tctctctgtc gcccaggctg gagtgcagtg gctcgatctc    5460
tgctcactgc aagctccgcc ccccaggttc acgccattct gtcacctcag cctccccagt    5520
agctgggagt acaggcgctc gccaccacgc cctgctaatt ttgttttttgt atttttagta    5580
gagatgggt  tcactgtgt  tagccaggat ggtcttgatc tcctgacctc gtgatctgcc    5640
cgcctcggcc tcccaaagcg ctgggattac aggcatgagc cactgcgcct ggccgagcct    5700
tgtggttttc aaattatctc atggagtcct agaattttga gaggttttgtc tagggatgcc    5760
tttggcgtca ggaggtgggg agagggaagt agaagcagtc gagtttcagg ctttccatgc    5820
```

-continued

| | | | | |
|---|---|---|---|---|
| ttgctttcaa | caggggcatct | tcggtttcgt | accttttatg | taattgagat tccacagatt | 5880 |
| aaaagctgac | attgcctacc | gctttaaaaa | gtttggaaag | ttttccactc atctaacact | 5940 |
| catattttat | agatgagaag | atcgaagccc | acaaagggaa | ggctctttgc ccacagaacc | 6000 |
| agagccaggt | ctagagctgc | aactaaatcc | tctgccactc | taagagagct ctcgctctac | 6060 |
| tgccctgtct | ccctttgcct | ccccatccct | ctggctacag | ctcagctctt cccacccctg | 6120 |
| tgtctatcac | tgaaggagtt | accccatct | caggcattga | ctcaggatgc cctggttta | 6180 |
| aggtggtctg | gccatgagtg | gtggtgggga | cggtccctag | gagggctatc tatgggaggt | 6240 |
| cccctggctg | ccccaggaga | taggccaagt | ttctttgggc | accctcaga gtggccttat | 6300 |
| ttttttcctc | caggcaacct | ccaagtccca | gatcatgtct | ctgtggggtc tggtctccaa | 6360 |
| gatgccccca | gaaaaagtgc | agcggctcta | tgtcgacttt | ccccaacacc tgcggcatct | 6420 |
| tctgggtgac | tggctggaga | gccagccctg | gtgagtcctg | gctgctccct gctggtcccc | 6480 |
| caagtcttcc | ctaactcatc | ttccttctcc | ttagattttt | ctcccctcac ccatggattc | 6540 |
| agaacttgag | acctgttatt | ccatgtgtag | tgacctagat | ttagcaggga gtctgtgccc | 6600 |
| catcaagacc | aggctatgaa | tgttgacaga | tggagacccc | catctcttag gaggctgagc | 6660 |
| cgaagaggag | gggggtttgg | gctgggacaa | aggcacttct | cataacagct agaagactgg | 6720 |
| gaaacaaggc | gcatgggtga | aagctacaga | gggcctagat | ggagaataag gagcgagaaa | 6780 |
| ggaatgctga | cttttggctg | tggggtaaag | gtcaggaaac | tgaagaagcc tggcctgaag | 6840 |
| tacctctcct | gatcttcctg | caaggagtt | cctggtcggc | tccgacgcct tctgctgcaa | 6900 |
| cttggctagt | gccctacttt | cagacactgt | ccagcacctt | caggcctcgg tgggagagca | 6960 |
| gggggagggg | agcaccatct | tgcaacacat | cagcacccct | gaggtgggggc aggaggggag | 7020 |
| gggacaaggc | tgggtggggc | tgaggttgaa | ctgggttgag | cattgggccc tggaagaaaa | 7080 |
| ttggttggat | gctggaagca | aattggtgtt | cctgtggtta | actgctagct agcaggcaaa | 7140 |
| ttagatttta | aaagcatgca | aatgcacaaa | aacttctgga | gtctacagtt gtgcttcctt | 7200 |
| atagtatatg | tgtgaatgca | ggcctgggga | ttggagggat | tgaaggacat gggtaagagc | 7260 |
| aaagctcact | gtttaccacc | ctcatttctg | tagagcatat | atcagaggga ccccctgaag | 7320 |
| ctggtggcca | ctttcagaca | aatacttcaa | ggagagaaaa | aagctgttat ggaacaggta | 7380 |
| ttgtgatatt | ccacctccca | ccccaactca | atccctgag | actttggcct gagccatgac | 7440 |
| aaactagaaa | gaatttgatc | ctcagaaaag | gctcagtgtt | ctaggcccag gaatgaccaa | 7500 |
| aggaggttcc | tagggtcaga | gtgaacccca | agtcaagctc | agggaatctt tctatgaggg | 7560 |
| actgaaggta | agaggccggg | gagaacagag | caagggataa | ggagctgatt ctgctaggag | 7620 |
| caaggtctta | tctccacgat | attccaaaag | gtcaggaaga | actgccaaag gggagagggg | 7680 |
| aacaagaaaa | cgctatatgc | agagcagaga | gtggaggcca | ggtatagagg gatgagcaga | 7740 |
| gtgtttgagt | tcttggcatc | tgtccttcct | gtgtagttcc | gccacttgcc aatgcctttc | 7800 |
| cactggaagc | aggaagaact | caagtttaag | acaggcttgc | ggaggctgca gcaccgagta | 7860 |
| ggggagatcc | accttctccg | acaagccctg | cagaaggggg | ctgaggctgg ccaaggtggg | 7920 |
| ggccagggtg | gttctgggga | gtgtgtaaga | gtggttgcct | cttggatctc aaccttatct | 7980 |
| gaacctctaa | tctgtctgca | cccttgattt | ctgcccccaa | ccctcagtgt ctctgcacag | 8040 |
| cttgatagaa | actcctgcta | atgggactgg | gccaagtgag | gtgagtaatg gctgacaggg | 8100 |
| tggagacctt | ggtcaaagtg | cagctggagg | gatggaagct | agacctcaga aagacacagg | 8160 |
| ctgaagtagg | gcaagggaat | gccagaggag | tgagaaaaag | accgtatccc aggagctggg | 8220 |

```
tgtggaggca gcgtgaggcc ctggctcagg cccctctctg cccataggcc ctggccatgc    8280
tactgcagga gaccactgga gagctagagg cagccaaagc cctagtgctg aagaggatcc    8340
agatttggaa acgcagcag cagctggcag ggaatggcgc accgtttgag gagagcctgg     8400
ccccactcca ggagaggttg ggctagggct gatggggaag aggggcaag ctgggggtgg     8460 gcagctgacc ctgctgaagg ccctacaggt gagagaaaga agccaggcgg gagggccttg    8520
gcagtggacc aagatgcata aaagccagtt ccagcggggc tgtgcacact gtcgttcagg    8580
tcgcatcctg tacaagtggg cctagtggag gggcacaagc ggggactcat ccaacccagg    8640
cttctctcct caagcccat gcctagagga ataggagggc ttttccattt ggtttattgg     8700
gtgggaacac ttcccaattt gccacaaagc actgtaagtg gtggcagttg ttcttgggtg    8760
caagaaccgt cggggagagg cagctgggtt tccacagggg gtgtaggcaa ctgataatga    8820
acctcccacc cacaccctag gccaacagat cacagaaccc cttcagccca ggtgccttgc    8880
agccacaccc actacccacc ccacttctcc acacatgata gccttctcc ctgggtatag     8940 gggaaggggg tctgggccgg agcaagcagc cttaatcctg tgcccctga ccactgtcct     9000 ggccccaggt gtgaaagcct ggtggacatt tattcccagc tacagcagga ggtaggggcg    9060
gctggtgggg agcttgagcc caagaccggg gcatcgctga ctggccggct ggatgaagtc    9120
ctgagaaccc tcgtcaccag gtattccccg ggagctccca gtctggccta aacagacct     9180 cgggaagaaa agaaggggc tagagctgtg ggagggcac cagcagggac ctagccccca     9240 actcccttg tgtcctcctc actcccagtt gcttcctggt ggagaagcag cccccccagg    9300
tactgaagac tcagaccaag ttccaggctg gagttcgatt cctgttgggc ttgaggttcc    9360
tgggggcccc agccaagcct ccgctggtca gggccgacat ggtgacagag aagcaggcgc    9420
gggagctgag tgtgcctcag ggtcctgggg ctggagcgta agctgggatt ggacctgggg    9480
ttggagaagg gctgttaggg tgatggaggc agcctggagg gctggcactg aaaagagcaa    9540
gggatgggga gggagggcca tgggatgtgg agaccctgaa tggtcaaggc agaggaaagg    9600
gagggaccca tttagggctg gaatgggtg ggggcatcat gatttggcca agatggggac     9660
tcctccctta agaacccaaa cagagacatg gagatttagg gctggtgaca gtgggtagtc    9720
tacactcacc catgcactcg ccacacctga cgacagtgag atgagctcgt tcacactctg    9780 acctccctg gcagagaaa gcactggaga aatcatcaac aacactgtgc ccttggagaa      9840
cagcattcct gggaactgct gctctgccct gttcaagaac ctggtgaggg gctttggggt    9900
gcagtgaggg gggcaccact aggagactgt gggactctcc ttggagagga tgtcaggaag    9960
cccaggagga gcggtctctg tcctcatgac ctcgcccttg ctctccctca ccccacccac   10020
agcttctcaa gaagatcaag cggtgtgagc ggaagggcac tgagtctgtc acagaggaga   10080
agtgcgctgt gctcttctct gccagcttca cacttggccc cggcaaactc cccatccagc   10140
tccaggtgaa ccgtggccca gccctgcccc aatctgggac cccgagtcct cctccaatgc   10200
cacgcacaag ggcctggac cctcacctct tgtgactgcc ccatacccca tgtgtctggg    10260
attcatgcac actggggccc gggtgagtgg gggtgagcaa gagcatggag tgcacagggc   10320
agggaatggt agtggatagc agcaaacact tcggaagcac ttcctataga ccaggggcac   10380
tctattaaat gatacatact gcacatgcgt gccagcacac acacgtctgg ttttcacaat   10440
aacattatga ggtaggcagt attatcagcc tcattttata gcatgaggac attgagacag   10500
agagtttaag tagtttgtcc cagtcaccca gctaagtgtt ggagctggta tctgaaacct   10560
```

```
ggaagtctgg ttccatagcg attatagtaa ccacttctct acggtgaggc cctgattgag    10620
cttcaaaacg catttaataa catggggaaa gaaagaaaga aagaaaccc tgtcctcacc    10680
ctacttcagg ccctgtctct gccctggtg gtcatcgtcc atggcaacca agacaacaat    10740
gccaaagcca ctatcctgtg ggacaatgcc ttctctgaga tggtgaggaa agtccttggt    10800
agttggaggg aacagggtgc aggtgggtt ctaacatggg cagtggtgca ggcctgctga    10860
tggggtggtg ggcatgtcgg atgggtgtga ccttaacact tcttcatggg cctgctttcg    10920
tgcttctgac ctcttttcac cccagtctta acaactatca ggccacagca ctgtaaccta    10980
caaaaaacag catgtttgtg agcgatatca ggggctgtgg aggggtaggc cacaggcatg    11040
tgggacggat gaaggccggc ccgaggaata caagacggt agcctgcagt gctctcttct    11100
tccccttct ccccaggacc gcgtgccctt tgtggtggct gagcgggtgc cctgggagaa    11160
gatgtgtgaa actctgaacc tgaagttcat ggctgaggtg gggaccaacc ggggctgct    11220
cccagagcac ttcctcttcc tggcccagaa gatcttcaat gacaacagcc tcagtatgga    11280
ggccttccag caccgttctg tgtcctggtc gcagttcaac aaggttcagt ctccgcggc    11340
cgcgagctct aatacgactc actataggc gtcgactcga tcataccact gcactcaagc    11400
ctgggtgaca gagcaagact ctgtctcaaa aaaaaaaaaa aaaaaggcc aggcatggtg    11460
gttcatgcct gtaatcccag cactttggga ggccgagacg gatagatcac ctgaggtcag    11520
gagttcgaga ccagcctggc caacatggca aaaccccgtc tctactaaaa acaaaaaat    11580
agccaggatg gtcgtttgcg tctgtaatcc cagctactcg gctgaggcag gaggtgaacc    11640
caggaggtaa aggctgcagg ggaagatgaa accattgcac tccagcctgg gcaagactct    11700
gtatcaaaaa aaaaaaaaaa aaggctaggt gtggtggctc acacctgtaa tcccagcact    11760
ttgggaggct gaggcgggcg gatcacaagg tcaagaaatc gagaccatcc tgaccaacat    11820
ggtgaaaccc cgtctctact aaaaatacaa aaattacctg gcatggtgg cgcatgcctg    11880
tattcccaac tactcgggag gctgaggcat gaaaatcact tgaacctggg aggcagaggt    11940
tgcaggcgag ccaagattgt gccactgcac tccagcctgc aacaaaaat gagattctgt    12000
cggttacctt ccctttgggc gtcaacttct gccacacctc cttagggaga gggtgtagca    12060
tagtagttaa gagggtcca gggccagaat gcctgggttt aaatcctagc tctgcctctt    12120
accagctatg tagacctggg caagtcattc gacgttttg gacttccatt tcttcatctg    12180
taagatggaa ttattataat ccctacttcc atagcctggt aaagagcaaa taatatatg    12240
gaaaggcttg aaatagtggc tggcacgtgt aagcattagg attggtcgtt gtcattgatg    12300
gagtctcagg ttcggtctga tcctcagccc tgtgattct gtcgtgaggg cactcacagc    12360
tcactgcctg ccctaaacag gctccagctc tggccctccc tcggctcaca ccttccccc    12420
tctccccta ggagatcctg ctgggccgtg gcttcacctt ttggcagtgg tttgatggtg    12480
tcctggacct caccaaacgc tgtctccgga gctactggtc tgaccggtga gtccccaccc    12540
tgggtagttt gagcagccat acaccagtca cctccatact cactgcccat gccccatcct    12600
ctccttcatc ccggccaggc tgatcattgg cttcatcagc aaacagtacg ttactagcct    12660
tcttctcaat gagcccgacg gaacctttct cctccgcttc agcgactcag agattggggg    12720
catcaccatt gcccatgtca tccggggcca ggatggtgag gccaccccag ccagtcctct    12780
gtctctgtgc ctgtgccctc tgggtttct tctgggaatg aaatgtcctg accttcctga    12840
tgccgatcct gatcttcagg aagttcttcc agcttctctt cttccttctg tggtctaaat    12900
gttcaccttc tcactgtgag ctctgtggga acggagacta gtgggtctct ctccctcagg    12960
```

```
agccccaccc taggtcctct ctcccttgcc ttggtggagt gagaacaggt cttatggtag   13020 ggggttgggga aggggaagaa atccggacag agggatctca gggtctcctt cctaccatag   13080
gctctccaca gatagagaac atccagccat tctctgccaa agacctgtcc attcgctcac   13140
tgggggaccg aatccgggat cttgctcagc tcaaaaatct ctatcccaag aagcccaagg   13200
atgaggcttt ccggagccac tacaagcgtg agctggaact ggcagctctg attccttcct   13260
gtcacccact tcctgccatg ctccccgctg ccatcctctc cccagcccgt gagttatcct   13320
gaggtcactc cgaatttcca tagctgtgct tttcttactt cccggatgat ccatgcccac   13380
cttttccacc tcccttcctc cctaacccga gagcaatcca tggcagtctt ttccatctca   13440
caacagctga acagctgaac agatgggtaa ggatggcagg ggttatgtcc cagctaccat   13500
caagatgacc gtggaaaggt gagtgtggtg gtatggacag tgggtaggtc aggggcttag   13560
tgcttatctg caggaaggag gggtggcatc aaccccttggt cagtcacatg tacctccttc   13620
cctcctccag ggaccaacca cttcctaccc cagagctcca gatgcctacc atggtgcctt   13680
cttatgacct tggaatggcc cctgattcct ccatgagcat gcagcttggc ccagatatgg   13740
tgtaaggagc tggaaagaca ggaatgggag tggtctgtgc agatgggcta atcttagcat   13800
gggcagctgg gagagctggc actgggggct gaacagggaa tcttcctttc catgagaggg   13860
acacctgttc aaaagcaggg tgtggtggtg tccaggagaa gggctggcat caggggggtct   13920 gttttctttc cccaggcccc aagtgtaccc accacactct cactccatcc ccccgtatca   13980
aggcctctcc ccagaagaat cagtcaacgt gttgtcagcc ttccaggagt aagtgaaaaa   14040
cctcatgggg ataccatccc actctaaggg ggtgggcatt tgaattgtta gaagaggctc   14100
ttctgtgaga aaggagcagc aaatgctaac agcctgtctt cttctcttct gtccactcta   14160 atgaggggggt agtagttaag atctggactg cctaggtttg aattctagct ccaccactta   14220
ctggtttggg gcaaattact tagcctttgg tgccttatct gcacaatggg ggataataat   14280
gctaataata ataacctacc tcactgcatt attgtggaga ttaaatgagt tcataacact   14340
taaaaagctc gagcatagtg catggctcat agcaaaagct gtgtaagtcc agtcgtggat   14400
cacttaatga aggagcattt tctgtctttg gcagtttcat aattatgcgg ataccattg    14460 agtataatta cacaaaccta gatggtatag actactatac actgaggcta tattgtgtag   14520
cctattgatc ctagctttaa acccgagcag catgatactg ttctgaatag tataaggaaa   14580
tagtaacata atgtaaata tttgtgtgat aggaattttc agcttgatta taatttttt    14640 tttttgagac agggtctcac tcactggagt gcagtggtgc gatcttagct cccctgcaac   14700
ctccgcctct tgggctcgag caatcctcct gctgtagtgc accacgacac tcggctaatt   14760 ctttttttaag atttttctgc agacaaggtc tcacttactg cccaagctgg tctcaaactc   14820
ctgggcttaa gtgatcctcc cacctcggcc tcccaaagcg ttaggattac aggcgtgagt   14880
cactctgcct ggccttgatt ataatcttat gggaccactg tggtctgtag ttgacagaaa   14940
tgtcgttaat gtggtgcatg actgttatta ttattttctg tcctgcccct gagagccact   15000
gtcacttctc tgctgtattg gttttttgttt actcatctgt tttggccttg aaatggccta   15060
gacatttttc ttcccgaagt atgacactcg ggtgcttatt aacttagtca agacacaaca   15120
tctcccttcc cagaaagtga ggcgggagtg aggacttggg gacttaagaa ctaccaaagt   15180
tcagagtcca aaggaaacat tagaaattgg gtaatccacc cccataacac gcacatttta   15240
cagatgagaa gactgagctc agagcataga aatagcttgc ccaggccatg actaagtcag   15300
```

```
gataaggagc tggagcttgt ttcctcactc agtggtcctg actttgcacc actctgcatt   15360
tgcctagcct gccttcctct aactgtgctc tccctacttc caggcctcac ctgcagatgc   15420
cccccagcct gggccagatg aacctgccct tgaccagcc tcaccccag gtgaatgaca     15480 aaagcccctc ctgacccatg tgcctcttct ttcctgggcc ttgcccgctc tccttatttc   15540
cattgctggt tcctggcagg gcctgctgcc gtgccagcct caggagcatg ctgtgtccag   15600
ccctgacccc ctgctctgct cagatgtgac catggtggaa gacagctgcc tgagccagcc   15660
agtgacagcg tttcctcagg gcacttggtg agtggcagct tgggagtgga ggctgggtgg   15720
catctagggg agtgggcgcc atgcctactc cactgcttct cccatctcct tgcaggattg   15780
gtgaagacat attccctcct ctgctgcctc ccactgaaca ggacctcact aagcttctcc   15840
tggaggggca aggggagtcg gggggagggt ccttgggggc acagcccctc ctgcagccct   15900
cccactatgg gcaatctggg atctcaatgt cccacatgga cctaagggcc aaccccagtt   15960
ggtgatccca gctggaggga aacccaaag agacagctct tctactaccc ccacagacct    16020
gctctggaca cttgctcatg ccctgccaag cagcagatgg ggagggtgcc ctcctatccc   16080
cacctactcc tgggtcagga ggaaaagact aacaggagaa tgcacagtgg gtggagccaa   16140
tccactcctt cctttctatc attccctgc ccacctcctt ccagcactga ctggaaggga    16200
agttcaggct ctgagacacg ccccaacatg cctgcacctg cagcgcgcac acgcacgcac   16260
acacacatac agagctctct gagggtgatg gggctgagca ggaggggggc tgggtaagag   16320
cacaggttag ggcatggaag gcttctccgc ccattctgac ccagggccta ggacggatag   16380
gcaggaacat acagacacat ttacactaga ggccagggat agaggatatt gggtctcagc   16440
cctaggggaa tgggaagcag ctgaagggac cctgggtggg agcataggag gagtctggac   16500
atgtggttac tagtacaggt tttgccctga ttaaaaaatc tcccaaagcc ccaaattcct   16560
gttagccagg tggaggcttc tgatacgtgt atgagactat gcaaaagtac aagggctgag   16620
attcttcgtg tatagctgtg tgaacgtgta tgtacctagg atatgttaaa tatatagctg   16680
gcaccttagt tgcatgacca catagaacat gtgtctatct gcttttgcct acgtgacaac   16740
acaaatttgg gagggtgaga cactgcacag aagacagcag caagtgtgct ggcctctctg   16800
acatatgcta accccaaat actctgaatt tggagtctga ctgtgcccaa gtgggtccaa    16860
gtggctgtga catctacgta tggctccaca cctccaatgc tgcctgggag ccagggtgag   16920
agtctgggtc caggcctggc catgtggccc tccagtgtat gagagggccc tgcctgctgc   16980
atcttttctg ttgccccatc caccgccagc ttcccttcac tccctatcc cattctccct    17040 ctcaaggcag gggtcataga tcctaagcca taaaataaat tttattccaa ataacaaaa    17100 taaataatct actgtacaca atctgaaaag aaagacgctc taactgctca gataggtgct   17160
gcggtccagc cccagctgg aggagaccct gagtccaacc caggcctccc gagggggcca    17220
gtgaagggat cccacaccca ccgcccctat gtagggcagg aagaaattg caaaggactt    17280 gggggataga tgggaatggg agggcaaact gcagcacttg ttaaattaat taagaaaca    17340 aaccagaagc acaaaaacgg ggaaggagaa gggagaagga gcaggtccag tgttccaggc   17400
cccaattctg ggggcaaatg tgcca                                        17425
```

<210> SEQ ID NO 6
<211> LENGTH: 23
<212> TYPE: PRT
<213> ORGANISM: Artificial Sequence
<220> FEATURE:
<223> OTHER INFORMATION: Description of artificial Sequence:/Note - synthetic construct

<400> SEQUENCE: 6

Val Pro Gln Val Tyr Pro Pro His Ser His Ser Ile Pro Pro Tyr Gln
 1               5                  10                  15

Gly Leu Ser Pro Glu Glu Ser
             20

<210> SEQ ID NO 7
<211> LENGTH: 18
<212> TYPE: PRT
<213> ORGANISM: Artificial Sequence
<220> FEATURE:
<223> OTHER INFORMATION: Description of artificial Sequence:/Note -
      synthetic construct

<400> SEQUENCE: 7

Gly Glu Asp Ile Phe Pro Pro Leu Leu Pro Pro Thr Glu Gln Asp Leu
 1               5                  10                  15

Thr Lys

<210> SEQ ID NO 8
<211> LENGTH: 21
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 8
gatctaactt cccaagaaca g                                        21

<210> SEQ ID NO 9
<211> LENGTH: 20
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 9
gtatttccca gaaaaggaac                                          20

<210> SEQ ID NO 10
<211> LENGTH: 30
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 10
ctgggatcct atggggcctg gaagtgccgc                               30

<210> SEQ ID NO 11
<211> LENGTH: 31
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 11
atgaattcgt ggccaccagc ttcaggggt c                              31

```
<210> SEQ ID NO 12
<211> LENGTH: 24
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 12
ctgggatccg gagctactgg tctg                                              24

<210> SEQ ID NO 13
<211> LENGTH: 24
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 13
atgaattctt gggatagaga tttt                                              24

<210> SEQ ID NO 14
<211> LENGTH: 20
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 14
gtatttccca gaaaggaac                                                    20

<210> SEQ ID NO 15
<211> LENGTH: 21
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 15
ctgtccagcg agttcaaggc t                                                 21

<210> SEQ ID NO 16
<211> LENGTH: 229
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 16
agccactgct tacactgaag agggaggacg ggagaggagt gtgtgtgtgt gtgtgtgtgt        60
gtgtgtgtat gtatgtgtgt gctttatctt attttctttt ttggtggtgg tgttggaagg      120
ggggaggtgc tagcagggcc agccttgaac tcgctggaca gagctacaga cctatggggc      180
ctggaagtgc ccgctgagaa agggagaaga cagcagaggg gttgccgag                  229

<210> SEQ ID NO 17
<211> LENGTH: 961
<212> TYPE: DNA
<213> ORGANISM: Artificial Sequence
<220> FEATURE:
<223> OTHER INFORMATION: Description of artificial Sequence:/Note -
      synthetic construct
<221> NAME/KEY: misc_feature
```

```
<222> LOCATION: (1)...(961)
<223> OTHER INFORMATION: Note: n = a, t, c, or g

<400> SEQUENCE: 17 tgggggagc tctcgggatc ctccctggc tggtggatg gtccccaang agatggtttc        60
agctantgtt ggtggctggt ggcactgggt tttancagtt tcgaactcct ggaggaactg    120
ggagggtcca ggcctcanta ctcccctccc ccatgggtca cgttttcaca gcctcacccc    180
tgcaccccca agggcccatg gaaagtcagg gaaaggaggt gaaggagtgc ccctctgccc    240
tgagtcgggg gaagtggccg cccctccctg gaaggttgat cgcagagggc agtggatcct    300
tgttaaaccc ctatcctgcc ctccactaaa ggttcctgtt caagggtgtg gctggggcgt    360
gagcaagccc cagatgtaga cctcatggtg gcccagacga gggggaattt cccctcaaa     420 actgctccac gcttggctcg tgtagacgct gagatttccc agcggcggcg ccgaattaac    480
cctcctcgtg ctgaactggc tccacctccc cgccttgccc ccaccgccac attcacgcat    540
tgggcaactc agagaagatg ttttaactt cgatcctgtg gtccacaatg agaggactcg     600
ggcagatagg ggttgagata agcgagttta ggccaccaag cgggcggacg aggatcccag    660
accttgcgct tcccttctga gtttgggagg taacactggc ccgccctc acgccgtggc      720 tcctccctcc cttccccttc aaggggctga agacaaaagg tgccctgtc ctggtcaagc     780 caatcgaccc agccttgtta tgggttgggg tggggaaaaa tgagtcctcc tgatggctgg    840
ggaagaagag gggttggata tttctagcca gggccatgcc aggaggctgg tcactctgca    900
aggggatgca gaggaaagcg gagcccactc actccagagg accttcctct tcttgggcta    960
g                                                                    961

<210> SEQ ID NO 18
<211> LENGTH: 68
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 18
agaaaggcct attggaggaa cctgagcagg agggtaagg attctgcctt gaggagaaaa      60
gagctggg                                                              68

<210> SEQ ID NO 19
<211> LENGTH: 1744
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 19 gtaagtggc actggaggaa agagggcat gaaggtcttg gagcagaaac gtccagagaa       60
gggacctctc cattttccat ccctctgaga ggcctgggag aggtgagagg ctgaacgtgc    120
aacaggagga cttggggtta ctgggtttgg ggagacctgg ggagttgtca tcccatcctc    180
tccctcatct ctgggagagg gatattatga gaaacgtgaa ctgagaggcc cctgggaaac    240
cactggttac ccagtcctcc ctgaacctgg aaatggggat gcaaccccct cttctacttc    300 cctgtccct cctctccttt ctacctgttt tcgtctctca tctttgcctt ctagccctcc     360
agcttcctct ctcttctagg ctctttcctc ctagcttact aaacccgcct tttttccagt    420
```

```
ctcttccatc ctcttcctta gttctctcta ctttccttt ccacctctcc tccttcaagt      480
ctcctcccac cttccccac ttcttaggat gatcagattt gccctggaa gggatcctaa      540 caacacagtg cgatggttaa tccccactca gattcaaagc ctgctttcca aactcactta      600
ctgagtggcc ttgggcagag tagagaaact ccttaagcct cagtttcttc atctataaaa      660
tgggatatta tatattttaa aaagtgtcgt gaggcctgaa ggagataata cactgagtgt      720
aatgcctcat acacagtaag tgcttaacaa atagtagctg ttattactct cccatcctct      780
tcatcatcta gccttgtggt tttcatttt attttatttc atttatttat ttatttattt      840
tgagcagagt ctctctctgt cgcccaggct ggagtgcagt ggctcgatct ctgctcactg      900
caagctccgc cccccaggtt cacgccattc tgtcacctca gcctcccag tagctgggag      960 tacaggcgct cgccaccacg ccctgctaat tttgtttttg tatttttagt agagatgggg     1020
tttcactgtg ttagccagga tggtcttgat ctcctgacct cgtgatctgc ccgcctcggc     1080
ctcccaaagc gctgggatta caggcatgag ccactgcgcc tggccgagcc ttgtggtttt     1140
caaattatct catggagtcc tagaattttg agaggtttgt ctaggatgc ctttggcgtc     1200 aggaggtggg gagagggaag tagaagcagt cgagtttcag gctttccatg cttgctttca     1260
acagggcatc ttcggtttcg tacctttat gtaattgaga ttccacagat taaaagctga     1320
cattgcctac cgctttaaaa agtttggaaa gttttccact catctaacac tcatatttta     1380
tagatgagaa gatcgaagcc cacaaaggga aggctctttg cccacagaac cagagccagg     1440
tctagagctg caactaaatc ctctgccact ctaagagagc tctcgctcta ctgccctgtc     1500
tccctttgcc tccccatccc tctggctaca gctcagctct tcccacccct gtgtctatca     1560
ctgaaggagt taccccatc tcaggcattg actcaggatg cccctggttt aaggtggtct     1620
ggccatgagt ggtggtgggg acggtcccta ggagggctat ctatgggagg tccctggct     1680 gccccaggag ataggccaag tttctttggg caccctcag agtggcctta tttttttcct     1740
ccag                                                                 1744

<210> SEQ ID NO 20
<211> LENGTH: 137
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 20
gcaacctcca agtcccagat catgtctctg tggggtctgg tctccaagat gccccagaa       60 aaagtgcagc ggctctatgt cgactttccc caacacctgc ggcatcttct gggtgactgg     120
ctggagagcc agccctg                                                    137

<210> SEQ ID NO 21
<211> LENGTH: 414
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 21
gtgagtcctg gctgctccct gctggtcccc caagtcttcc ctaactcatc ttccttctcc       60
ttagattttt ctcccctcac ccatggattc agaacttgag acctgttatt ccatgtgtag     120
tgacctagat ttagcaggga gtctgtgccc catcaagacc aggctatgaa tgttgacaga     180
```

```
tggagacccc catctcttag gaggctgagc cgaagaggag gggggtttgg gctgggacaa      240
aggcacttct cataacagct agaagactgg gaaacaaggc gcatgggtga aagctacaga      300
gggcctagat ggagaataag gagcgagaaa ggaatgctga cttttggctg tggggtaaag      360
gtcaggaaac tgaagaagcc tggcctgaag tacctctcct gatcttcctg caag           414
```

<210> SEQ ID NO 22
<211> LENGTH: 139
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 22

```
ggagttcctg gtcggctccg acgccttctg ctgcaacttg gctagtgccc tactttcaga       60
cactgtccag caccttcagg cctcggtggg agagcagggg gagggagca ccatcttgca      120 acacatcagc acccttgag                                                   139
```

<210> SEQ ID NO 23
<211> LENGTH: 139
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 23

```
ggagttcctg gtcggctccg acgccttctg ctgcaacttg gctagtgccc tactttcaga       60
cactgtccag caccttcagg cctcggtggg agagcagggg gagggagca ccatcttgca      120 acacatcagc acccttgag                                                   139
```

<210> SEQ ID NO 24
<211> LENGTH: 84
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 24

```
agcatatatc agagggaccc cctgaagctg gtggccactt tcagacaaat acttcaagga       60
gagaaaaaag ctgttatgga acag                                              84
```

<210> SEQ ID NO 25
<211> LENGTH: 399
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 25

```
gtattgtgat attccacctc ccaccccaac tcaatcccct gagactttgg cctgagccat       60
gacaaactag aaagaatttg atcctcagaa aaggctcagt gttctaggcc caggaatgac      120
caaaggaggt tcctagggtc agagtgaacc ccaagtcaag ctcagggaat ctttctatga      180
gggactgaag gtaagaggcc ggggagaaca gagcaaggga taaggagctg attctgctag      240
gagcaaggtc ttatctccac gatattccaa aaggtcagga agaactgcca aagggagag      300
```
gggaacaaga aaacgctata tgcagagcag agagtggagg ccaggtatag agggatgagc    360
agagtgtttg agttcttggc atctgtcctt cctgtgtag                           399

<210> SEQ ID NO 26
<211> LENGTH: 139
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 26
ttccgccact tgccaatgcc tttccactgg aagcaggaag aactcaagtt taagacaggc    60
ttgcggaggc tgcagcaccg agtaggggag atccaccttc tccgacaagc cctgcagaag   120
ggggctgagg ctggccaag                                                139

<210> SEQ ID NO 27
<211> LENGTH: 112
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 27
gtgggggcca gggtggttct ggggagtgtg taagagtggt tgcctcttgg atctcaacct    60
tatctgaacc tctaatctgt ctgcacccct gatttctgcc cccaaccctc ag           112

<210> SEQ ID NO 28
<211> LENGTH: 53
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 28
tgtctctgca cagcttgata gaaactcctg ctaatgggac tgggccaagt gag            53

<210> SEQ ID NO 29
<211> LENGTH: 187
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 29
gtgagtaatg ggctgacagg tggagacctt ggtcaaagtg cagctggagg gatggaagct    60
agacctcaga aagacacagg ctgaagtagg gcaagggaat gccagaggag tgagaaaaag   120
accgtatccc aggagctggg tgtggaggca gcgtgaggcc ctggctcagg cccctctctg   180
cccatag                                                             187

<210> SEQ ID NO 30
<211> LENGTH: 149
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 30

-continued

```
gccctggcca tgctactgca ggagaccact ggagagctag aggcagccaa agccctagtg     60
ctgaagagga tccagatttg gaaacggcag cagcagctgg cagggaatgg cgcaccgttt    120
gaggagagcc tggccccact ccaggagag                                      149
```

<210> SEQ ID NO 31
<211> LENGTH: 592
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 31

```
gttgggctag ggctgatggg gaagaggggg caagctgggg gtgggcagct gaccctgctg     60
aaggccctac aggtgagaga aagaagccag gcgggagggc cttggcagtg gaccaagatg    120
cataaaagcc agtccagcg  gggctgtgca cactgtcgtt caggtcgcat cctgtacaag    180
tgggcctagt ggaggggcac aagcgggac  tcatccaacc caggcttctc tcctcaagcc    240
ccatgcctag aggaatagga gggcttttcc atttggttta ttgggtggga acacttccca    300
atttgccaca aagcactgta agtggtggca gttgttcttg ggtgcaagaa ccgtcgggga    360
gaggcagctg ggtttccaca gggggtgtag gcaactgata atgaacctcc cacccacacc    420
ctaggccaac agatcacaga accccttcag cccaggtgcc ttgcagccac acccactacc    480
caccccactt ctccacacat gatagccttt ctccctgggt ataggggaag ggggtctggg    540
ccggagcaag cagccttaat cctgtgcccc ctgaccactg tcctggcccc ag            592
```

<210> SEQ ID NO 32
<211> LENGTH: 132
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 32

```
gtgtgaaagc ctggtggaca tttattccca gctacagcag gaggtagggg cggctggtgg     60
ggagcttgag cccaagaccc gggcatcgct gactggccgg ctggatgaag tcctgagaac    120
cctcgtcacc ag                                                        132
```

<210> SEQ ID NO 33
<211> LENGTH: 128
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 33

```
gtattccccg ggagctccca gtctggccta gaacagacct cgggaagaaa agaaggggc      60 tagagctgtg gggagggcac cagcagggac ctagccccca actccccttg tgtcctcctc    120
actcccag                                                             128
```

<210> SEQ ID NO 34
<211> LENGTH: 189
<212> TYPE: DNA
<213> ORGANISM: Artificial Sequence
<220> FEATURE:
<223> OTHER INFORMATION: Description of artificial Sequence:/Note -
      synthetic construct

```
<400> SEQUENCE: 34
ttgcttcctg gtggagaagc agccccccca ggtactgaag actcagacca agttccaggc    60
tggagttcga ttcctgttgg gcttgaggtt cctgggggcc ccagccaagc ctccgctggt   120
cagggccgac atggtgacag agaagcaggc gcgggagctg agtgtgcctc agggtcctgg   180
ggctggagc                                                          189

<210> SEQ ID NO 35
<211> LENGTH: 338
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 35
gtaagctggg attggacctg gggttggaga agggctgtta gggtgatgga ggcagcctgg    60
agggctggca ctgaaaagag caagggatgg ggagggaggg ccatgggatg tggagaccct   120
gaatggtcaa ggcagaggaa agggagggac ccatttaggg ctggaatggg gtgggggcat   180
catgatttgg ccaagatggg gactcctccc ttaagaaccc aaacagagac atggagattt   240
agggctggtg acagtgggta gtctacactc acccatgcac tcgccacacc tgacgacagt   300
gagatgagct cgttcacact ctgacctccc ctgggcag                          338

<210> SEQ ID NO 36
<211> LENGTH: 88
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 36
agaaagcact ggagaaatca tcaacaacac tgtgcccttg agaacagca ttcctgggaa     60 ctgctgctct gccctgttca agaacctg                                      88

<210> SEQ ID NO 37
<211> LENGTH: 139
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 37
gtgaggggct ttggggtgca gtgaggggg caccactagg agactgtggg actctccttg     60
gagaggatgt caggaagccc aggaggagcg gtctctgtcc tcatgacctc gcccttgctc   120
tccctcaccc cacccacag                                                139

<210> SEQ ID NO 38
<211> LENGTH: 123
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 38
cttctcaaga agatcaagcg gtgtgagcgg aagggcactg agtctgtcac agaggagaag    60
```

```
tgcgctgtgc tcttctctgc cagcttcaca cttggccccg gcaaactccc catccagctc    120
cag                                                                  123
```

```
<210> SEQ ID NO 39
<211> LENGTH: 545
<212> TYPE: DNA
<213> ORGANISM: Artificial Sequence
<220> FEATURE:
<223> OTHER INFORMATION: Description of artificial Sequence:/Note -
      synthetic construct
<221> NAME/KEY: misc_feature
<222> LOCATION: (1)...(545)
<223> OTHER INFORMATION: Note: n = a, t, c, or g

<400> SEQUENCE: 39
gtgaaccgtg gcccagccct gccccaatct gggaccccga gtcctcctcc aatgccacgc     60
acaagggccc tggaccctca cctcttgtga ctgccccata ccccatgtgt ctgggattca    120
tgcacactgg ggcccgggtg agtggggtg agcaagagca tggagtgcac agggcaggga    180
atggtagtgg atagcagcaa acacttcgga agcacttcct atagaccagg ggcactctat    240
taaatgatac atactgcaca tgcgtgccag cacacacacg tctggttttc acaataacat    300
tatgaggtag gcagtattat cagcctcatt ttatagcatg aggacattga dacagagagt    360
ttaagtagtt tgtcccagtc acccagctaa gtgttggagc tggtatctga aacctggaag    420
tctggttcca tagcgattat agtaaccact tctctacggt gaggccctga ttgagcttca    480
aaacgcattt aataacatgg nggaaagaaa gaaagaaaag aaaccctgtc ctcaccctac    540
ttcag                                                                545
```

```
<210> SEQ ID NO 40
<211> LENGTH: 93
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 40
gccctgtctc tgccctggt ggtcatcgtc catggcaacc aagacaacaa tgccaaagcc     60
actatcctgt gggacaatgc cttctctgag atg                                 93
```

```
<210> SEQ ID NO 41
<211> LENGTH: 334
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 41
gtgaggaaag tccttggtag ttggagggaa cagggtgcag ggtgggttct aacatgggca     60
gtggtgcagg cctgctgatg gggtggtggg catgtcggat gggtgtgacc ttaacacttc    120
ttcatgggcc tgctttcgtg cttctgacct cttttcaccc cagtcttaac aactatcagg    180
ccacagcact gtaacctaga aaaacagca tgtttgtgag cgatatcagg ggctgtggag     240
gggtaggcca caggcatgtg ggacggatga aggccggccc gaggaataac aagacggtag    300
cctgcagtgc tctcttcttc ccccttctcc ccag                                334
```

```
<210> SEQ ID NO 42
<211> LENGTH: 207
```

<210> SEQ ID NO 42
<211> LENGTH: 207
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 42

```
gaccgcgtgc cctttgtggt ggctgagcgg gtgccctggg agaagatgtg tgaaactctg      60
aacctgaagt tcatggctga ggtggggacc aaccgggggc tgctcccaga gcacttcctc     120
ttcctggccc agaagatctt caatgacaac agcctcagta tggaggcctt ccagcaccgt     180
tctgtgtcct ggtcgcagtt caacaag                                         207
```

<210> SEQ ID NO 43
<211> LENGTH: 1110
<212> TYPE: DNA
<213> ORGANISM: Artificial Sequence
<220> FEATURE:
<223> OTHER INFORMATION: Description of artificial Sequence:/Note - synthetic construct
<221> NAME/KEY: misc_feature
<222> LOCATION: (1)...(1110)
<223> OTHER INFORMATION: Note: n = a, t, c, or g

<400> SEQUENCE: 43

```
gttcagttct ccngcggccg cgagctctaa tacgactcac tatagggcgt cgactcgatc      60
ataccactgc actcaagcct gggtgacaga gcaagactct gtctcaaaaa aaaaaaaaaa     120
aaaaggccag gcatggtggt tcatgcctgt aatcccagca ctttgggagg ccgagacgga     180
tagatcacct gaggtcagga gttcgagacc agcctggcca acatggcaaa accccgtctc     240
tactaaaaac aaaaaaatag ccaggatggt cgtttgcgtc tgtaatccca gctactcggc     300
tgaggcagga ggtgaaccca ggaggtaaag gctgcagggg aagatgaaac cattgcactc     360
cagcctgggc aagactctgt atcaaaaaaa aaaaaaaaaa ggctaggtgt ggtggctcac     420
acctgtaatc ccagcacttt gggaggctga ggcgggcgga tcacaaggtc aagaaatcga     480
gaccatcctg accaacatgg tgaaacccog tctctactaa aaatacaaaa attacctggg     540
catggtggcg catgcctgta ttcccaacta ctcgggaggc tgaggcatga aaatcacttg     600
aacctgggag gcagaggttg caggcgagcc aagattgtgc cactgcactc cagcctgcca     660
acaaaaatga gattctgtcn ggttaccttc cctttgggcg tcaacttctg ccacacctcc     720
ttagggagag ggtgtagcat agtagttaag aggggtccag ggccagaatg cctgggttta     780
aatcctagct ctgcctctta ccagctatgt agacctgggc aagtcattcg acgttttttgg     840
acttccatt cttcatctgt aagatggaat tattataatc cctacttcca tagcctggta     900
aagagcaaat aaatatatgg aaaggcttga aatagtggct ggcacgtgta agcattagga     960
ttggtcgttg tcattgatgg agtctcaggt tcggtctgat cctcagcccc tgtgattctg    1020
tcgtgagggc actcacagct cactgcctgc cctaaacagg ctccagctct ggccctccct    1080
cggctcacac ctttccccct ctccccctag                                     1110
```

<210> SEQ ID NO 44
<211> LENGTH: 95
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 44

```
gagatcctgc tgggccgtgg cttcaccttt tggcagtggt ttgatggtgt cctggacctc      60
accaaacgct gtctccggag ctactggtct gaccg                                 95
```

<210> SEQ ID NO 45
<211> LENGTH: 92
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 45

```
gtgagtcccc accctgggta gtttgagcag ccatacacca gtcacctcca tactcactgc      60
ccatgcccca tcctctcctt catcccggcc ag                                    92
```

<210> SEQ ID NO 46
<211> LENGTH: 137
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 46

```
gctgatcatt ggcttcatca gcaaacagta cgttactagc cttcttctca atgagcccga      60
cggaaccttt ctcctccgct tcagcgactc agagattggg ggcatcacca ttgcccatgt     120
catccggggc caggatg                                                    137
```

<210> SEQ ID NO 47
<211> LENGTH: 325
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 47

```
gtgaggccac cccagccagt cctctgtctc tgtgcctgtg ccctctgggg tttcttctgg      60
gaatgaaatg tcctgacctt cctgatgccg atcctgatct tcaggaagtt cttccagctt    120
ctcttcttcc ttctgtggtc taaatgttca ccttctcact gtgagctctg tgggaacgga    180
gactagtggg tctctctccc tcaggagccc caccctaggt cctctctccc ttgccttggt    240
ggagtgagaa caggtcttat ggtagggtt ggggaagggg aagaaatccg gacagaggga     300
tctcagggtc tccttcctac catag                                          325
```

<210> SEQ ID NO 48
<211> LENGTH: 147
<212> TYPE: DNA
<213> ORGANISM: Artificial Sequence
<220> FEATURE:
<223> OTHER INFORMATION: Description of artificial Sequence:/Note - synthetic construct

<400> SEQUENCE: 48

```
gctctccaca gatagagaac atccagccat tctctgccaa agacctgtcc attcgctcac      60
tgggggaccg aatccgggat cttgctcagc tcaaaaatct ctatcccaag aagcccaagg    120
atgaggcttt ccggagccac tacaagc                                        147
```

<210> SEQ ID NO 49
<211> LENGTH: 227

<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 49
gtgagctgga actggcagct ctgattcctt cctgtcaccc acttcctgcc atgctccccg    60
ctgccatcct ctccccagcc cgtgagttat cctgaggtca ctccgaattt ccatagctgt   120
gcttttctta cttcccggat gatccatgcc cacctttttcc acctcccttc ctccctaacc   180
cgagagcaat ccatggcagt cttttccatc tcacaacagc tgaacag                227

<210> SEQ ID NO 50
<211> LENGTH: 64
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 50
ctgaacagat gggtaaggat ggcaggggtt atgtcccagc taccatcaag atgaccgtgg    60
aaag                                                                64

<210> SEQ ID NO 51
<211> LENGTH: 112
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 51
gtgagtgtgg tggtatggac agtgggtagg tcaggggctt agtgcttatc tgcaggaagg    60
aggggtggca tcaacccttg gtcagtcaca tgtacctcct tccctcctcc ag           112

<210> SEQ ID NO 52
<211> LENGTH: 111
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 52
ggaccaacca cttcctaccc cagagctcca gatgcctacc atggtgcctt cttatgacct    60
tggaatggcc cctgattcct ccatgagcat gcagcttggc ccagatatgg t            111

<210> SEQ ID NO 53
<211> LENGTH: 194
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 53
gtaaggagct ggaaagacag gaatgggagt ggtctgtgca gatgggctaa tcttagcatg    60
ggcagctggg agagctggca ctggggctg aacaggaat cttcctttcc atgagaggga    120
cacctgttca aaagcagggt gtggtggtgt ccaggagaag ggctggcatc aggggtctg    180 ttttctttcc ccag                                                     194

<210> SEQ ID NO 54
<211> LENGTH: 93
<212> TYPE: DNA
<213> ORGANISM: Artificial Sequence
<220> FEATURE:
<223> OTHER INFORMATION: Description of artificial Sequence:/Note -
       synthetic construct

<400> SEQUENCE: 54

```
gccccaggtg tacccaccac actctcactc catcccccg tatcaaggcc tctccccaga      60
agaatcagtc aacgtgttgt cagccttcca gga                                  93
```

<210> SEQ ID NO 55
<211> LENGTH: 1375
<212> TYPE: DNA
<213> ORGANISM: Artificial Sequence
<220> FEATURE:
<223> OTHER INFORMATION: Description of artificial Sequence:/Note -
       synthetic construct

<400> SEQUENCE: 55

```
gtaagtgaaa aacctcatgg ggataccatc ccactctaag ggggtgggca tttgaattgt      60
tagaagaggc tcttctgtga gaaggagca gcaaatgcta acagcctgtc ttcttctctt     120
ctgtccactc taatgagggg gtagtagtta agatctggac tgcctaggtt tgaattctag    180
ctccaccact tactggtttg gggcaaatta cttagccttt ggtgccttat ctgcacaatg    240
ggggataata atgctaataa taataaccta cctcactgca ttattgtgga gattaaatga    300
gttcataaca cttaaaaagc tcgagcatag tgcatggctc atagcaaaag ctgtgtaagt    360
ccagtcgtgg atcacttaat gaaggagcat tttctgtctt tggcagtttc ataattatgc    420
ggaataccat tgagtataat tacacaaacc tagatggtat agactactat acactgaggc    480
tatattgtgt agcctattga tcctagcttt aaacccgagc agcatgatac tgttctgaat    540
agtataagga aatagtaaca taatggtaaa tatttgtgtg ataggaattt tcagcttgat    600
tataattttt tttttttgag acagggtctc actcactgga gtgcagtggt gcgatcttag    660
ctcccctgca acctccgcct cttgggctcg agcaatcctc ctgctgtagt gcaccacgac    720
actcggctaa ttctttttta agatttttct gcagacaagg tctcacttac tgcccaagct    780
ggtctcaaac tcctgggctt aagtgatcct cccacctcgg cctcccaaag cgttaggatt    840
acaggcgtga gtcactctgc ctggccttga ttataatctt atgggaccac tgtggtctgt    900
agttgacaga aatgtcgtta atgtggtgca tgactgttat tattattttc tgtcctgccc    960
ctgagagcca ctgtcacttc tctgctgtat tggttttgt ttactcatct gttttggcct    1020
tgaaatggcc tagacatttt tcttcccgaa gtatgacact cgggtgctta ttaacttagt   1080
caagacacaa catctcccctt cccagaaagt gaggcgggag tgaggacttg gggacttaag   1140
aactaccaaa gttcagagtc caaggaaac attagaaatt gggtaatcca ccccataac     1200 acgcacattt tacagatgag aagactgagc tcagagcata gaaatagctt gcccaggcca   1260
tgactaagtc aggataagga gctggagctt gtttcctcac tcagtggtcc tgactttgca   1320
ccactctgca tttgcctagc ctgccttcct ctaactgtgc tctccctact tccag        1375
```

<210> SEQ ID NO 56
<211> LENGTH: 66
<212> TYPE: DNA
<213> ORGANISM: Artificial Sequence
<220> FEATURE:

```
<223> OTHER INFORMATION: Description of artificial Sequence:/Note -
      synthetic construct

<400> SEQUENCE: 56
gcctcacctg cagatgcccc ccagcctggg ccagatgaac ctgccctttg accagcctca    60
ccccca                                                                66

<210> SEQ ID NO 57
<211> LENGTH: 89
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 57
gtgaatgaca aaagcccctc ctgacccatg tgcctcttct ttcctgggcc ttgcccgctc    60
tccttatttc cattgctggt tcctggcag                                       89

<210> SEQ ID NO 58
<211> LENGTH: 128
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 58
ggcctgctgc cgtgccagcc tcaggagcat gctgtgtcca gccctgaccc cctgctctgc    60
tcagatgtga ccatggtgga agacagctgc ctgagccagc cagtgacagc gtttcctcag    120
ggcacttg                                                              128

<210> SEQ ID NO 59
<211> LENGTH: 88
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 59
gtgagtggca gcttgggagt ggaggctggg tggcatctag gggagtgggc gccatgccta    60
ctccactgct ctcccatct ccttgcag                                         88

<210> SEQ ID NO 60
<211> LENGTH: 1350
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 60
gattggtgaa gacatattcc ctcctctgct gcctcccact gaacaggacc tcactaagct    60
tctcctggag gggcaagggg agtcgggggg agggtccttg ggggcacagc ccctcctgca    120
gccctcccac tatgggcaat ctgggatctc aatgtccac atggacctaa ggccaaccc     180 cagttggtga tcccagctgg agggagaacc caaagagaca gctcttctac tacccccaca    240
gacctgctct ggacacttgc tcatgccctg ccaagcagca gatggggagg gtgccctcct    300
atccccacct actcctgggt caggaggaaa agactaacag gagaatgcac agtgggtgga    360
```

```
gccaatccac tccttcctttt ctatcattcc cctgcccacc tccttccagc actgactgga      420
agggaagttc aggctctgag acacgcccca acatgcctgc acctgcagcg cgcacacgca      480
cgcacacaca catacagagc tctctgaggg tgatggggct gagcaggagg ggggctgggt      540
aagagcacag gttagggcat ggaaggcttc tccgcccatt ctgacccagg gcctaggacg      600
gataggcagg aacatacaga cacatttaca ctagaggcca gggatagagg atattgggtc      660
tcagccctag gggaatggga agcagctgaa gggaccctgg gtgggagcat aggaggagtc      720
tggacatgtg gttactagta caggttttgc cctgattaaa aaatctccca aagcccccaa      780
ttcctgttag ccaggtggag gcttctgata cgtgtatgag actatgcaaa agtacaaggg      840
ctgagattct tcgtgtatag ctgtgtgaac gtgtatgtac ctaggatatg ttaaatatat      900
agctggcacc ttagttgcat gaccacatag aacatgtgtc tatctgcttt tgcctacgtg      960
acaacacaaa tttgggaggg tgagacactg cacagaagac agcagcaagt gtgctggcct     1020
ctctgacata tgctaacccc caaatactct gaatttggag tctgactgtg cccaagtggg     1080
tccaagtggc tgtgacatct acgtatggct ccacacctcc aatgctgcct gggagccagg     1140
gtgagagtct gggtccaggc ctggccatgt ggccctccag tgtatgagag ggccctgcct     1200
gctgcatctt ttctgttgcc ccatccaccg ccagcttccc ttcactcccc tatcccattc     1260
tccctctcaa ggcagggggtc atagatccta agccataaaa taaattttat tccaaaataa     1320
caaaataaat aatctactgt acacaatctg                                      1350

<210> SEQ ID NO 61
<211> LENGTH: 300
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 61
aaaagaaaga cgctctaact gctcagatag gtgctgcggt ccagccccca gctggaggag       60
accctgagtc caacccaggc ctcccgaggg ggccagtgaa gggatcccac acccaccgcc      120
cctatgtagg gcagggaaga aattgcaaag gacttggggg atagatggga atgggagggc      180
aaactgcagc acttgttaaa ttaattaaag aaacaaacca gaagcacaaa aacggggaag      240
gagaagggag aaggagcagg tccagtgttc caggccccaa ttctgggggc aaatgtgcca      300

<210> SEQ ID NO 62
<211> LENGTH: 28
<212> TYPE: PRT
<213> ORGANISM: Artificial Sequence
<220> FEATURE:
<223> OTHER INFORMATION: Description of artificial Sequence:/Note -
      synthetic construct

<400> SEQUENCE: 62

Leu Ile Ile Gly Phe Ile Ser Lys Gln Tyr Val Thr Ser Leu Leu Leu
 1               5                  10                  15

Asn Glu Pro Asp Gly Thr Phe Leu Leu Arg Phe Ser
            20                  25

<210> SEQ ID NO 63
<211> LENGTH: 18
<212> TYPE: PRT
<213> ORGANISM: Artificial Sequence
<220> FEATURE:
<223> OTHER INFORMATION: Description of artificial Sequence:/Note -
``` synthetic construct

<400> SEQUENCE: 63

Phe Ile Ser Lys Gln Tyr Val Thr Ser Leu Leu Leu Asn Glu Pro Asp
 1               5                  10                  15

Gly Thr

<210> SEQ ID NO 64
<211> LENGTH: 16
<212> TYPE: PRT
<213> ORGANISM: Artificial Sequence
<220> FEATURE:
<223> OTHER INFORMATION: Description of artificial Sequence:/Note -
      synthetic construct

<400> SEQUENCE: 64

Met Pro Pro Glu Lys Val Gln Arg Leu Tyr Val Asp Phe Pro Gln His
 1               5                  10                  15

<210> SEQ ID NO 65
<211> LENGTH: 19
<212> TYPE: PRT
<213> ORGANISM: Artificial Sequence
<220> FEATURE:
<223> OTHER INFORMATION: Description of artificial Sequence:/Note -
      synthetic construct

<400> SEQUENCE: 65

Ser Asp Thr Val Gln His Leu Gln Ala Ser Val Gly Glu Gln Gly Glu
 1               5                  10                  15

Gly Ser Thr

<210> SEQ ID NO 66
<211> LENGTH: 16
<212> TYPE: PRT
<213> ORGANISM: Artificial Sequence
<220> FEATURE:
<223> OTHER INFORMATION: Description of artificial Sequence:/Note -
      synthetic construct

<400> SEQUENCE: 66

Leu Arg Ser Tyr Trp Ser Asp Arg Asp Ser Glu Ile Gly Gly Ile Thr
 1               5                  10                  15

<210> SEQ ID NO 67
<211> LENGTH: 3375
<212> TYPE: DNA
<213> ORGANISM: Artificial Sequence
<220> FEATURE:
<223> OTHER INFORMATION: Description of artificial Sequence:/Note -
      synthetic construct
<221> NAME/KEY: CDS
<222> LOCATION: (115)...(2655)

<400> SEQUENCE: 67
ggccagcctt gaactcgctg gacagagcta cagacctatg gggcctggaa gtgcccgctg      60
agaaagggag aagacagcag aggggttgcc gaggcaacct ccaagtccca gatc atg     117
                                                            Met
                                                             1 tct ctg tgg ggt ctg gtc tcc aag atg ccc cca gaa aaa gtg cag cgg     165
Ser Leu Trp Gly Leu Val Ser Lys Met Pro Pro Glu Lys Val Gln Arg
         5                  10                  15 ctc tat gtc gac ttt ccc caa cac ctg cgg cat ctt ctg ggt gac tgg     213
Leu Tyr Val Asp Phe Pro Gln His Leu Arg His Leu Leu Gly Asp Trp
     20                  25                  30

```
ctg gag agc cag ccc tgg gag ttc ctg gtc ggc tcc gac gcc ttc tgc    261
Leu Glu Ser Gln Pro Trp Glu Phe Leu Val Gly Ser Asp Ala Phe Cys
     35                  40                  45 gcc tcg gtg gga gag cag ggg gag ggg agc acc atc ttg caa cac atc    309
Ala Ser Val Gly Glu Gln Gly Glu Gly Ser Thr Ile Leu Gln His Ile
 50                  55                  60                  65 agc acc ctt gag agc ata tat cag agg gac ccc ctg aag ctg gtg gcc    357
Ser Thr Leu Glu Ser Ile Tyr Gln Arg Asp Pro Leu Lys Leu Val Ala
                 70                  75                  80 act ttc aga caa ata ctt caa gga gag aaa aaa gct gtt atg gaa cag    405
Thr Phe Arg Gln Ile Leu Gln Gly Glu Lys Lys Ala Val Met Glu Gln
             85                  90                  95 ttc cgc cac ttg cca atg cct ttc cac tgg aag cag gaa gaa ctc aag    453
Phe Arg His Leu Pro Met Pro Phe His Trp Lys Gln Glu Glu Leu Lys
        100                 105                 110 ttt aag aca ggc ttg cgg agg ctg cag cac cga gta ggg gag atc cac    501
Phe Lys Thr Gly Leu Arg Arg Leu Gln His Arg Val Gly Glu Ile His
    115                 120                 125 ctt ctc cga gaa gcc ctg cag aag ggg gct gag gct ggc caa gtg tct    549
Leu Leu Arg Glu Ala Leu Gln Lys Gly Ala Glu Ala Gly Gln Val Ser
130                 135                 140                 145 ctg cac agc ttg ata gaa act cct gct aat ggg act ggg cca agt gag    597
Leu His Ser Leu Ile Glu Thr Pro Ala Asn Gly Thr Gly Pro Ser Glu
                150                 155                 160 gcc ctg gcc atg cta ctg cag gag acc act gga gag cta gag gca gcc    645
Ala Leu Ala Met Leu Leu Gln Glu Thr Thr Gly Glu Leu Glu Ala Ala
            165                 170                 175 aaa gcc cta gtg ctg aag agg atc cag att tgg aaa cgg cag cag cag    693
Lys Ala Leu Val Leu Lys Arg Ile Gln Ile Trp Lys Arg Gln Gln Gln
        180                 185                 190 ctg gca ggg aat ggc gca ccg ttt gag gag agc ctg gcc cca ctc cag    741
Leu Ala Gly Asn Gly Ala Pro Phe Glu Glu Ser Leu Ala Pro Leu Gln
    195                 200                 205 gag agg tgt gaa agc ctg gtg gac att tat tcc cag cta cag cag gag    789
Glu Arg Cys Glu Ser Leu Val Asp Ile Tyr Ser Gln Leu Gln Gln Glu
210                 215                 220                 225 gta ggg gcg gct ggt ggg gag ctt gag ccc aag acc cgg gca tcg ctg    837
Val Gly Ala Ala Gly Gly Glu Leu Glu Pro Lys Thr Arg Ala Ser Leu
                230                 235                 240 act ggc cgg ctg gat gaa gtc ctg aga acc ctc gtc acc agt tgc ttc    885
Thr Gly Arg Leu Asp Glu Val Leu Arg Thr Leu Val Thr Ser Cys Phe
            245                 250                 255 ctg gtg gag aag cag ccc ccc cag gta ctg aag act cag acc aag ttc    933
Leu Val Glu Lys Gln Pro Pro Gln Val Leu Lys Thr Gln Thr Lys Phe
        260                 265                 270 cag gct gga gtt cga ttc ctg ttg ggc ttg agg ttc ctg ggg gcc cca    981
Gln Ala Gly Val Arg Phe Leu Leu Gly Leu Arg Phe Leu Gly Ala Pro
    275                 280                 285 gcc aag cct ccg ctg gtc agg gcc gac atg gtg aca gag aag cag gcg   1029
Ala Lys Pro Pro Leu Val Arg Ala Asp Met Val Thr Glu Lys Gln Ala
290                 295                 300                 305 cgg gag ctg agt gtg cct cag ggt cct ggg gct gga gca gaa agc act   1077
Arg Glu Leu Ser Val Pro Gln Gly Pro Gly Ala Gly Ala Glu Ser Thr
                310                 315                 320 gga gaa atc atc aac aac act gtg ccc ttg gag aac agc att cct ggg   1125
Gly Glu Ile Ile Asn Asn Thr Val Pro Leu Glu Asn Ser Ile Pro Gly
            325                 330                 335 aac tgc tgc tct gcc ctg ttc aag aac ctg ctt ctc aag aag atc aag   1173
Asn Cys Cys Ser Ala Leu Phe Lys Asn Leu Leu Leu Lys Lys Ile Lys
```

```
              340                 345                 350
cgg tgt gag cgg aag ggc act gag tct gtc aca gag gag aag tgc gct    1221
Arg Cys Glu Arg Lys Gly Thr Glu Ser Val Thr Glu Glu Lys Cys Ala
355                 360                 365 gtg ctc ttc tct gcc agc ttc aca ctt ggc ccc ggc aaa ctc ccc atc    1269
Val Leu Phe Ser Ala Ser Phe Thr Leu Gly Pro Gly Lys Leu Pro Ile
370                 375                 380                 385 cag ctc cag gcc ctg tct ctg ccc ctg gtg gtc atc gtc cat ggc aac    1317
Gln Leu Gln Ala Leu Ser Leu Pro Leu Val Val Ile Val His Gly Asn
                390                 395                 400 caa gac aac aat gcc aaa gcc act atc ctg tgg gac aat gcc ttc tct    1365
Gln Asp Asn Asn Ala Lys Ala Thr Ile Leu Trp Asp Asn Ala Phe Ser
            405                 410                 415 gag atg gac cgc gtg ccc ttt gtg gtg gct gag cgg gtg ccc tgg gag    1413
Glu Met Asp Arg Val Pro Phe Val Val Ala Glu Arg Val Pro Trp Glu
        420                 425                 430 aag atg tgt gaa act ctg aac ctg aag ttc atg gct gag gtg ggg acc    1461
Lys Met Cys Glu Thr Leu Asn Leu Lys Phe Met Ala Glu Val Gly Thr
    435                 440                 445 aac cgg ggg ctg ctc cca gag cac ttc ctc ttc ctg gcc cag aag atc    1509
Asn Arg Gly Leu Leu Pro Glu His Phe Leu Phe Leu Ala Gln Lys Ile
450                 455                 460                 465 ttc aat gac aac agc ctc agt atg gag gcc ttc cag cac cgt tct gtg    1557
Phe Asn Asp Asn Ser Leu Ser Met Glu Ala Phe Gln His Arg Ser Val
                470                 475                 480 tcc tgg tcg cag ttc aac aag gag atc ctg ctg ggc cgt ggc ttc acc    1605
Ser Trp Ser Gln Phe Asn Lys Glu Ile Leu Leu Gly Arg Gly Phe Thr
            485                 490                 495 ttt tgg cag tgg ttt gat ggt gtc ctg gac ctc acc aaa cgc tgt ctc    1653
Phe Trp Gln Trp Phe Asp Gly Val Leu Asp Leu Thr Lys Arg Cys Leu
        500                 505                 510 cgg agc tac tgg tct gac cgg ctg atc att ggc ttc atc agc aaa cag    1701
Arg Ser Tyr Trp Ser Asp Arg Leu Ile Ile Gly Phe Ile Ser Lys Gln
    515                 520                 525 tac gtt act agc ctt ctt ctc aat gag ccc gac gga acc ttt ctc ctc    1749
Tyr Val Thr Ser Leu Leu Leu Asn Glu Pro Asp Gly Thr Phe Leu Leu
530                 535                 540                 545 cgc ttc agc gac tca gag att ggg ggc atc acc att gcc cat gtc atc    1797
Arg Phe Ser Asp Ser Glu Ile Gly Gly Ile Thr Ile Ala His Val Ile
                550                 555                 560 cgg ggc cag gat ggc tct cca cag ata gag aac atc cag cca ttc tct    1845
Arg Gly Gln Asp Gly Ser Pro Gln Ile Glu Asn Ile Gln Pro Phe Ser
            565                 570                 575 gcc aaa gac ctg tcc att cgc tca ctg ggg gac cga atc cgg gat ctt    1893
Ala Lys Asp Leu Ser Ile Arg Ser Leu Gly Asp Arg Ile Arg Asp Leu
        580                 585                 590 gct cag ctc aaa aat ctc tat ccc aag aag ccc aag gat gag gct ttc    1941
Ala Gln Leu Lys Asn Leu Tyr Pro Lys Lys Pro Lys Asp Glu Ala Phe
    595                 600                 605 cgg agc cac tac aag cct gaa cag atg ggt aag gat ggc agg ggt tat    1989
Arg Ser His Tyr Lys Pro Glu Gln Met Gly Lys Asp Gly Arg Gly Tyr
610                 615                 620                 625 gtc cca gct acc atc aag atg acc gtg gaa agg gac caa cca ctt cct    2037
Val Pro Ala Thr Ile Lys Met Thr Val Glu Arg Asp Gln Pro Leu Pro
                630                 635                 640 acc cca gag ctc cag atg cct acc atg gtg cct tct tat gac ctt gga    2085
Thr Pro Glu Leu Gln Met Pro Thr Met Val Pro Ser Tyr Asp Leu Gly
            645                 650                 655 atg gcc cct gat tcc tcc atg agc atg cag ctt ggc cca gat atg gtg    2133
```

```
Met Ala Pro Asp Ser Ser Met Ser Met Gln Leu Gly Pro Asp Met Val
            660                 665                 670 ccc cag gtg tac cca cca cac tct cac tcc atc ccc ccg tat caa ggc      2181
Pro Gln Val Tyr Pro Pro His Ser His Ser Ile Pro Pro Tyr Gln Gly
675                 680                 685 ctc tcc cca gaa gaa tca gtc aac gtg ttg tca gcc ttc cag gag cct      2229
Leu Ser Pro Glu Glu Ser Val Asn Val Leu Ser Ala Phe Gln Glu Pro
690                 695                 700                 705 cac ctg cag atg ccc ccc agc ctg ggc cag atg agc ctg ccc ttt gac      2277
His Leu Gln Met Pro Pro Ser Leu Gly Gln Met Ser Leu Pro Phe Asp
                710                 715                 720 cag cct cac ccc cag ggc ctg ctg ccg tgc cag cct cag gag cat gct      2325
Gln Pro His Pro Gln Gly Leu Leu Pro Cys Gln Pro Gln Glu His Ala
            725                 730                 735 gtg tcc agc cct gac ccc ctg ctc tgc tca gat gtg acc atg gtg gaa      2373
Val Ser Ser Pro Asp Pro Leu Leu Cys Ser Asp Val Thr Met Val Glu
        740                 745                 750 gac agc tgc ctg agc cag cca gtg aca gcg ttt cct cag ggc act tgg      2421
Asp Ser Cys Leu Ser Gln Pro Val Thr Ala Phe Pro Gln Gly Thr Trp
    755                 760                 765 att ggt gaa gac ata ttc cct cct ctg ctg cct ccc act gaa cag gac      2469
Ile Gly Glu Asp Ile Phe Pro Pro Leu Leu Pro Pro Thr Glu Gln Asp
770                 775                 780                 785 ctc act aag ctt ctc ctg gag ggg caa ggg gag tcg ggg gga ggg tcc      2517
Leu Thr Lys Leu Leu Leu Glu Gly Gln Gly Glu Ser Gly Gly Gly Ser
                790                 795                 800 ttg ggg gca cag ccc ctc ctg cag ccc tcc cac tat ggg caa tct ggg      2565
Leu Gly Ala Gln Pro Leu Leu Gln Pro Ser His Tyr Gly Gln Ser Gly
            805                 810                 815 ttg ggg gca cag ccc ctc ctg cag ccc tcc cac tat ggg caa tct ggg      2613
Leu Gly Ala Gln Pro Leu Leu Gln Pro Ser His Tyr Gly Gln Ser Gly
        820                 825                 830 atc tca atg tcc cac atg gac cta agg gcc aac ccc agt tgg              2655
Ile Ser Met Ser His Met Asp Leu Arg Ala Asn Pro Ser Trp
    835                 840                 845 tgatcccagc tggagggaga acccaaagag acagctcttc tactaccccc acagacctgc    2715
tctggacact tgctcatgcc ctgccaagca gcagatgggg aggtgccct cctatcccca     2775 cctactcctg ggtcaggagg aaaagactaa caggagaatg cacagtgggt ggagccaatc    2835
cactccttcc tttctatcat tcccctgccc acctccttcc agcactgact ggaagggaag    2895
ttcaggctct gagacacgcc ccaacatgcc tgcacctgca gcgcgcacac gcacgcacac    2955
acacatacag agctctctga gggtgatggg gctgagcagg agggggctg gtaagagca      3015 caggttaggg catggaaggc ttctccgccc attctgaccc agggcctagg acggataggc    3075
aggaacatac agacacattt acactagagg ccagggatag aggatattgg gtctcagccc    3135
taggggaatg ggaagcagct caagggaccc tgggtgggag cataggagga gtctggacat    3195
gtggttacta gtacaggttt tgccctgatt aaaaaatctc ccaaagcccc aaattcctgt    3255
tagccaggtg gaggcttctg atacgtgtat gagactatgc aaaagtacaa gggctgagat    3315
tcttcgtgta aaaaaaaaaa aaaaaaaaaa aaaaaaaaaa aaaaaaaaaa aaaaaaaaaa    3375
```

<210> SEQ ID NO 68
<211> LENGTH: 847
<212> TYPE: PRT
<213> ORGANISM: Artificial Sequence
<220> FEATURE:
<223> OTHER INFORMATION: Description of artificial Sequence:/Note - synthetic construct -continued

```
<400> SEQUENCE: 68

Met Ser Leu Trp Gly Leu Val Ser Lys Met Pro Pro Glu Lys Val Gln
  1               5                  10                  15

Arg Leu Tyr Val Asp Phe Pro Gln His Leu Arg His Leu Leu Gly Asp
             20                  25                  30

Trp Leu Glu Ser Gln Pro Trp Glu Phe Leu Val Gly Ser Asp Ala Phe
         35                  40                  45

Cys Ala Ser Val Gly Glu Gln Gly Glu Gly Ser Thr Ile Leu Gln His
     50                  55                  60

Ile Ser Thr Leu Glu Ser Ile Tyr Gln Arg Asp Pro Leu Lys Leu Val
 65                  70                  75                  80

Ala Thr Phe Arg Gln Ile Leu Gln Gly Glu Lys Lys Ala Val Met Glu
                 85                  90                  95

Gln Phe Arg His Leu Pro Met Pro Phe His Trp Lys Gln Glu Glu Leu
            100                 105                 110

Lys Phe Lys Thr Gly Leu Arg Arg Leu Gln His Arg Val Gly Glu Ile
        115                 120                 125

His Leu Leu Arg Glu Ala Leu Gln Lys Gly Ala Glu Ala Gly Gln Val
    130                 135                 140

Ser Leu His Ser Leu Ile Glu Thr Pro Ala Asn Gly Thr Gly Pro Ser
145                 150                 155                 160

Glu Ala Leu Ala Met Leu Leu Gln Glu Thr Thr Gly Glu Leu Glu Ala
                165                 170                 175

Ala Lys Ala Leu Val Leu Lys Arg Ile Gln Ile Trp Lys Arg Gln Gln
            180                 185                 190

Gln Leu Ala Gly Asn Gly Ala Pro Phe Glu Glu Ser Leu Ala Pro Leu
        195                 200                 205

Gln Glu Arg Cys Glu Ser Leu Val Asp Ile Tyr Ser Gln Leu Gln Gln
    210                 215                 220

Glu Val Gly Ala Ala Gly Gly Glu Leu Glu Pro Lys Thr Arg Ala Ser
225                 230                 235                 240

Leu Thr Gly Arg Leu Asp Glu Val Leu Arg Thr Leu Val Thr Ser Cys
                245                 250                 255

Phe Leu Val Glu Lys Gln Pro Pro Gln Val Leu Lys Thr Gln Thr Lys
            260                 265                 270

Phe Gln Ala Gly Val Arg Phe Leu Leu Gly Leu Arg Phe Leu Gly Ala
        275                 280                 285

Pro Ala Lys Pro Pro Leu Val Arg Ala Asp Met Val Thr Glu Lys Gln
    290                 295                 300

Ala Arg Glu Leu Ser Val Pro Gln Gly Pro Gly Ala Gly Ala Glu Ser
305                 310                 315                 320

Thr Gly Glu Ile Ile Asn Asn Thr Val Pro Leu Glu Asn Ser Ile Pro
                325                 330                 335

Gly Asn Cys Cys Ser Ala Leu Phe Lys Asn Leu Leu Leu Lys Lys Ile
            340                 345                 350

Lys Arg Cys Glu Arg Lys Gly Thr Glu Ser Val Thr Glu Glu Lys Cys
        355                 360                 365

Ala Val Leu Phe Ser Ala Ser Phe Thr Leu Gly Pro Gly Lys Leu Pro
    370                 375                 380

Ile Gln Leu Gln Ala Leu Ser Leu Pro Leu Val Val Ile Val His Gly
385                 390                 395                 400

Asn Gln Asp Asn Asn Ala Lys Ala Thr Ile Leu Trp Asp Asn Ala Phe
```

-continued

```
                405                 410                 415
Ser Glu Met Asp Arg Val Pro Phe Val Val Ala Glu Arg Val Pro Trp
                420                 425                 430

Glu Lys Met Cys Glu Thr Leu Asn Leu Lys Phe Met Ala Glu Val Gly
            435                 440                 445

Thr Asn Arg Gly Leu Leu Pro Glu His Phe Leu Phe Leu Ala Gln Lys
        450                 455                 460

Ile Phe Asn Asp Asn Ser Leu Ser Met Glu Ala Phe Gln His Arg Ser
465                 470                 475                 480

Val Ser Trp Ser Gln Phe Asn Lys Glu Ile Leu Leu Gly Arg Gly Phe
                485                 490                 495

Thr Phe Trp Gln Trp Phe Asp Gly Val Leu Asp Leu Thr Lys Arg Cys
            500                 505                 510

Leu Arg Ser Tyr Trp Ser Asp Arg Leu Ile Ile Gly Phe Ile Ser Lys
        515                 520                 525

Gln Tyr Val Thr Ser Leu Leu Leu Asn Glu Pro Asp Gly Thr Phe Leu
    530                 535                 540

Leu Arg Phe Ser Asp Ser Glu Ile Gly Gly Ile Thr Ile Ala His Val
545                 550                 555                 560

Ile Arg Gly Gln Asp Gly Ser Pro Gln Ile Glu Asn Ile Gln Pro Phe
                565                 570                 575

Ser Ala Lys Asp Leu Ser Ile Arg Ser Leu Gly Asp Arg Ile Arg Asp
            580                 585                 590

Leu Ala Gln Leu Lys Asn Leu Tyr Pro Lys Pro Lys Asp Glu Ala
        595                 600                 605

Phe Arg Ser His Tyr Lys Pro Glu Gln Met Gly Lys Asp Gly Arg Gly
    610                 615                 620

Tyr Val Pro Ala Thr Ile Lys Met Thr Val Glu Arg Asp Gln Pro Leu
625                 630                 635                 640

Pro Thr Pro Glu Leu Gln Met Pro Thr Met Val Pro Ser Tyr Asp Leu
                645                 650                 655

Gly Met Ala Pro Asp Ser Ser Met Ser Met Gln Leu Gly Pro Asp Met
            660                 665                 670

Val Pro Gln Val Tyr Pro Pro His Ser His Ser Ile Pro Pro Tyr Gln
        675                 680                 685

Gly Leu Ser Pro Glu Glu Ser Val Asn Val Leu Ser Ala Phe Gln Glu
    690                 695                 700

Pro His Leu Gln Met Pro Pro Ser Leu Gly Gln Met Ser Leu Pro Phe
705                 710                 715                 720

Asp Gln Pro His Pro Gln Gly Leu Leu Pro Cys Gln Pro Gln Glu His
                725                 730                 735

Ala Val Ser Ser Pro Asp Pro Leu Leu Cys Ser Asp Val Thr Met Val
            740                 745                 750

Glu Asp Ser Cys Leu Ser Gln Pro Val Thr Ala Phe Pro Gln Gly Thr
        755                 760                 765

Trp Ile Gly Glu Asp Ile Phe Pro Pro Leu Leu Pro Thr Glu Gln
    770                 775                 780

Asp Leu Thr Lys Leu Leu Leu Glu Gly Gln Gly Glu Ser Gly Gly Gly
785                 790                 795                 800

Ser Leu Gly Ala Gln Pro Leu Leu Gln Pro Ser His Tyr Gly Gln Ser
                805                 810                 815

Gly Leu Gly Ala Gln Pro Leu Leu Gln Pro Ser His Tyr Gly Gln Ser
            820                 825                 830
```

```
Gly Ile Ser Met Ser His Met Asp Leu Arg Ala Asn Pro Ser Trp
        835                 840                 845

<210> SEQ ID NO 69
<211> LENGTH: 4
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 69 tata                                                                      4

<210> SEQ ID NO 70
<211> LENGTH: 5
<212> TYPE: DNA
<213> ORGANISM: Artificial Sequence
<220> FEATURE:
<223> OTHER INFORMATION: Description of artificial Sequence:/Note -
      synthetic construct

<400> SEQUENCE: 70 ccaat                                                                     5
```